(12) United States Patent
Ma et al.

(10) Patent No.: US 11,134,853 B2
(45) Date of Patent: Oct. 5, 2021

(54) SYSTEM AND METHOD FOR BLOOD PRESSURE MONITORING

(71) Applicant: VITA-COURSE TECHNOLOGIES CO., LTD., Guangdong (CN)

(72) Inventors: Ting Ma, Guangdong (CN); Jiao Yu, Guangdong (CN); Jiwei Zhao, Guangdong (CN); Zhiyong Wang, Guangdong (CN)

(73) Assignee: VITA-COURSE TECHNOLOGIES CO., LTD., Shenzhen (CN)

( * ) Notice: Subject to any disclaimer, the term of this patent is extended or adjusted under 35 U.S.C. 154(b) by 608 days.

(21) Appl. No.: 15/563,568

(22) PCT Filed: Jul. 3, 2015

(86) PCT No.: PCT/CN2015/083334
§ 371 (c)(1),
(2) Date: Sep. 30, 2017

(87) PCT Pub. No.: WO2016/155138
PCT Pub. Date: Oct. 6, 2016

(65) Prior Publication Data
US 2018/0085011 A1    Mar. 29, 2018

(30) Foreign Application Priority Data

Mar. 31, 2015   (CN) .......................... 201520188152.9

(51) Int. Cl.
*A61B 5/024*    (2006.01)
*A61B 5/00*    (2006.01)
(Continued)

(52) U.S. Cl.
CPC ........ *A61B 5/02416* (2013.01); *A61B 5/0225* (2013.01); *A61B 5/0245* (2013.01);
(Continued)

(58) Field of Classification Search
CPC .............. A61B 5/02416; A61B 5/0225; A61B 5/02255; A61B 5/0245; A61B 5/1102;
(Continued)

(56) References Cited

U.S. PATENT DOCUMENTS

| 5,316,008 A | 5/1994 | Suga et al. |
| 5,626,135 A | 5/1997 | Sanfilippo |

(Continued)

FOREIGN PATENT DOCUMENTS

| CN | 1698535 A | 11/2005 |
| CN | 1849998 A | 10/2006 |

(Continued)

OTHER PUBLICATIONS

Extended European Search Report in European Application No. 17773043.9 dated Mar. 21, 2019, 8 pages.

(Continued)

*Primary Examiner* — Eric F Winakur
*Assistant Examiner* — Abid A Mustansir
(74) *Attorney, Agent, or Firm* — Metis IP LLC

(57) ABSTRACT

A device (110), method and system (100) for calculating, estimating, or monitoring the blood pressure of a subject. At least one processor, when executing instructions, may perform one or more of the following operations. A first signal representing heart activity of the subject may be received. A second signal representing time-varying information on at least one pulse wave of the subject may be received. A first feature in the first signal may be identified. A second feature in the second signal may be identified. A pulse transit time based on a difference between the first feature and the second feature may be computed. The blood pressure of the subject may be calculated according to a first model based (Continued)

on the computed pulse transit time and a first set of calibration values, the first set of calibration values relating to the subject.

20 Claims, 23 Drawing Sheets

(51) Int. Cl.
```
A61B 5/021      (2006.01)
A61B 5/318      (2021.01)
A61B 5/0225     (2006.01)
A61B 5/0245     (2006.01)
A61B 5/11       (2006.01)
A61B 5/145      (2006.01)
A61B 5/1455     (2006.01)
G06F 21/31      (2013.01)
A61B 5/352      (2021.01)
A61B 5/026      (2006.01)
A61B 5/0205     (2006.01)
A61B 5/01       (2006.01)
```
(52) U.S. Cl.
CPC ...... *A61B 5/02125* (2013.01); *A61B 5/02141* (2013.01); *A61B 5/02255* (2013.01); *A61B 5/1102* (2013.01); *A61B 5/14542* (2013.01); *A61B 5/14551* (2013.01); *A61B 5/318* (2021.01); *A61B 5/7203* (2013.01); *A61B 5/7235* (2013.01); *A61B 5/746* (2013.01); *G06F 21/31* (2013.01); *A61B 5/01* (2013.01); *A61B 5/021* (2013.01); *A61B 5/0205* (2013.01); *A61B 5/026* (2013.01); *A61B 5/352* (2021.01); *A61B 2560/0228* (2013.01)

(58) Field of Classification Search
CPC .......... A61B 5/14542; A61B 5/14551; A61B 5/746; A61B 5/7203; A61B 5/7235; A61B 5/02125; A61B 5/01; A61B 5/0456; A61B 2560/0228; A61B 5/026; A61B 5/0205; A61B 5/021; G06F 21/31
See application file for complete search history.

(56) References Cited

U.S. PATENT DOCUMENTS

| | | | |
|---|---|---|---|
| 5,649,513 A | 7/1997 | Kanda | |
| 5,873,834 A | 2/1999 | Yanagi et al. | |
| 6,355,000 B1 | 3/2002 | Ogura | |
| 7,544,168 B2 | 6/2009 | Nitzan | |
| 7,674,231 B2 | 3/2010 | McCombie et al. | |
| 7,887,491 B2 | 2/2011 | Marks et al. | |
| 8,313,439 B2 | 11/2012 | McCombie et al. | |
| 8,740,802 B2 | 6/2014 | Banet et al. | |
| 9,439,599 B2 | 9/2016 | Thompson et al. | |
| 9,865,176 B2 | 1/2018 | Tran | |
| 2002/0147402 A1 | 10/2002 | Nitzan et al. | |
| 2003/0167012 A1 | 9/2003 | Friedman et al. | |
| 2005/0208969 A1 | 9/2005 | Kwoen | |
| 2005/0261574 A1 | 11/2005 | Li et al. | |
| 2005/0261593 A1* | 11/2005 | Zhang ................ A61B 5/02125 600/485 |
| 2007/0100247 A1 | 5/2007 | Platt et al. | |
| 2008/0039731 A1 | 2/2008 | McCombie et al. | |
| 2008/0221461 A1 | 9/2008 | Zhou et al. | |
| 2009/0018422 A1 | 1/2009 | Banet et al. | |
| 2009/0105605 A1 | 4/2009 | Abreu | |
| 2010/0049006 A1 | 2/2010 | Magar et al. | |
| 2010/0087743 A1 | 4/2010 | Hatib et al. | |
| 2010/0160798 A1* | 6/2010 | Banet ................ A61B 5/02133 600/490 |
| 2010/0249617 A1 | 9/2010 | Leung et al. | |
| 2011/0009718 A1 | 1/2011 | Gavish | |
| 2011/0066045 A1 | 3/2011 | Moon | |
| 2011/0231152 A1 | 9/2011 | Kawabe | |
| 2012/0101350 A1 | 4/2012 | Bychkov | |
| 2012/0136261 A1* | 5/2012 | Sethi ................ A61B 5/02125 600/485 |
| 2012/0316448 A1 | 12/2012 | Gu et al. | |
| 2013/0012823 A1 | 1/2013 | Ripoll et al. | |
| 2013/0053655 A1 | 2/2013 | Castellanos | |
| 2013/0197369 A1 | 8/2013 | Xiang | |
| 2014/0066788 A1 | 3/2014 | Mukkamala et al. | |
| 2014/0206976 A1 | 7/2014 | Thompson et al. | |
| 2015/0018637 A1 | 1/2015 | Chen et al. | |
| 2015/0125832 A1 | 5/2015 | Tran | |
| 2015/0313486 A1 | 11/2015 | Mestha et al. | |
| 2015/0320359 A1 | 11/2015 | Luo | |
| 2015/0374244 A1 | 12/2015 | Yoo et al. | |
| 2015/0377909 A1 | 12/2015 | Cavet et al. | |
| 2016/0270708 A1 | 9/2016 | Tateda et al. | |
| 2017/0109495 A1 | 4/2017 | Xin | |
| 2018/0116597 A1 | 5/2018 | Yu et al. | |
| 2018/0132744 A1 | 5/2018 | Yu et al. | |
| 2018/0160905 A1 | 6/2018 | Wang et al. | |

FOREIGN PATENT DOCUMENTS

| | | |
|---|---|---|
| CN | 100331625 C | 1/2008 |
| CN | 101327121 A | 12/2008 |
| CN | 100512750 C | 7/2009 |
| CN | 100560019 C | 11/2009 |
| CN | 101732040 A | 6/2010 |
| CN | 101810470 A | 8/2010 |
| CN | 102008296 A | 4/2011 |
| CN | 101248989 B | 10/2011 |
| CN | 101773387 B | 12/2011 |
| CN | 102397064 A | 4/2012 |
| CN | 102429649 A | 5/2012 |
| CN | 102488503 A | 6/2012 |
| CN | 101708121 B | 7/2012 |
| CN | 202505340 U | 10/2012 |
| CN | 103190891 A | 7/2013 |
| CN | 103385702 A | 11/2013 |
| CN | 103598876 A | 2/2014 |
| CN | 103637787 A | 3/2014 |
| CN | 103637788 A | 3/2014 |
| CN | 104720773 A | 3/2014 |
| CN | 102499669 B | 12/2014 |
| CN | 104173036 A | 12/2014 |
| CN | 204044771 U | 12/2014 |
| CN | 104257371 A | 1/2015 |
| CN | 104323764 A | 2/2015 |
| CN | 20407743 U | 3/2015 |
| CN | 104382571 A | 3/2015 |
| CN | 104398358 A | 3/2015 |
| CN | 104411150 A | 3/2015 |
| CN | 104414626 A | 3/2015 |
| CN | 104706348 A | 3/2015 |
| CN | 104523252 A | 4/2015 |
| CN | 204232699 U | 4/2015 |
| CN | 104635768 A | 6/2015 |
| CN | 204499693 U | 7/2015 |
| CN | 204506976 U | 7/2015 |
| CN | 104814729 A | 8/2015 |
| CN | 204674751 U | 9/2015 |
| WO | 2007110158 A1 | 10/2007 |
| WO | 2010135516 A2 | 11/2010 |
| WO | 2011008383 A1 | 1/2011 |
| WO | 2012040931 A1 | 4/2012 |
| WO | 2012128407 A1 | 9/2012 |
| WO | 2013171599 A1 | 11/2013 |
| WO | 2014195578 A1 | 12/2014 |
| WO | 2017005016 A1 | 1/2017 |

OTHER PUBLICATIONS

International Search Report and Written Opinion in PCT/CN2015/083334 dated Dec. 18, 2015, 16 pages.

(56) References Cited

OTHER PUBLICATIONS

International Search Report in PCT/CN2016/077469 dated Jun. 8, 2016, 5 pages.
Written Opinion in PCT/CN2016/077469 dated Jun. 8, 2016, 4 pages.
International Search Report in PCT/CN2017/076702 dated Jun. 7, 2010, 5 pages.
Written Opinion in PCT/CN2017/076702 dated Jun. 7, 2016, 5 pages.
International Search Report PCT/CN2016/070017 dated Apr. 13, 2016, 6 pages.
Written Opinion in PCT/CN2016/070017 dated Apr. 13, 2016, 8 pages.
Extended Search Report in European Application No. 17773043.9 dated Mar. 21, 2019, 6 pages.
Jordi Calabia et al., Doppler Ultrasound in the Measurement of Pulse Wave Velocity: Agreement with the Complior Method, Cardiovascular Ultrasound, 2011, 6 Pages.
Dlpreet Buxi et al., A Survey on Signals and Systems in Ambulatory Blood Pressure Monitoring Using Pulse Transit Time, Physiological Measurement, 36: R1-R26, 2015, 26 Pages.
Sung-Noon Kim et al., Beat-to-Beat Tracking of Systolic Blood Pressure Using Noninvasive Pulse Transit Time During Anesthesia Induction in Hypertensive Patients, Society for Technology in Anesthesia, 116(1): 94-100, 2012.
Andreas Patzak et al., Continuous Blood Pressure Measurement Using the Pulse Transit Time: Comparison to Intro-arterial Measurement, Blood Pressure, 2015, 5 Pages.
Guo Lihua, The Research of Cuffless and Continuous Blood Pressure Measurement Based on PPG, 2011, 74 Pages.
Liu Xiuhua, The Research of Continuous Blood Pressure Measuring Based on the Reflective Pulse Wave, 2012, 63 Pages.
Li Dingli, Research on Non-invasive Continuous Blood Pressure Measurement Based on Pulse Wave, 2008, 117 Pages.
Li Tongxin, Study of Continuous Blood Pressure Measurement Based on Pulse Wave, 2013, 61 Pages.
Wang Jicun, Research on Non-invasive Continuous Blood Pressure Measurement Based on Pulse Wave, 2009, 67 Pages.
Li Zhiyin, Design and Study on Prototype of Non-invasive Blood Pressure Monitoring System Based on Pulse Wave, 2009, 81 Pages.
Yu Sicong, Development and Clinical Verification of Blood Pressure Measuring Instrument Based on Pulse Wave, 2011, 55 Pages.
Liu Na, Research of Pulse-wave-based Algorithm in the Blood Pressure and Cardiovascular State Monitoring, 2004, 65 Pages.
Yu Xiao, A Non-invasive Continuous Blood Pressure Measurement System Based on Pulse Wave Velocity, 2013, 68 Pages.
Yan Guodong, Research on Non-invasive Blood Pressure Measurement Based on Pulse Wave, 2013, 53 Pages.
Li Xiaoxi, Research on Blood Pressure Measurement Method Based on Pulse Transit Time, 2012, 72 Pages.
Heidi Schmalgemeier et al., Pulse Transit Time: Validation of Blood Pressure Measurement under Positive Airway Pressure Ventilation, Sleep Breath, 16: 1105-1112, 2012.
Ji Lee et al., Noise Reduction and Adaptive Contrast Enhancement for Local Tone Mapping, IEEE Transactions on Consumer Electronics, 58(2): 578-586, 2012.
Ming Xin et al., 24-hour Non-invasive Continuous Blood Pressure Monitoring Based on Pulse, 17 Pages.
Jiao Xuejun et al., Research on Contnuous Measunment of Blood Pressure via Characterist, Parameters of Pulse Wave, Journal of Biomedical Engineering, 19(2): 217-220, 200.
First Office Action in Chinese Application No. 201780020746.0 dated Sep. 15, 2020, 19 pages.

\* cited by examiner

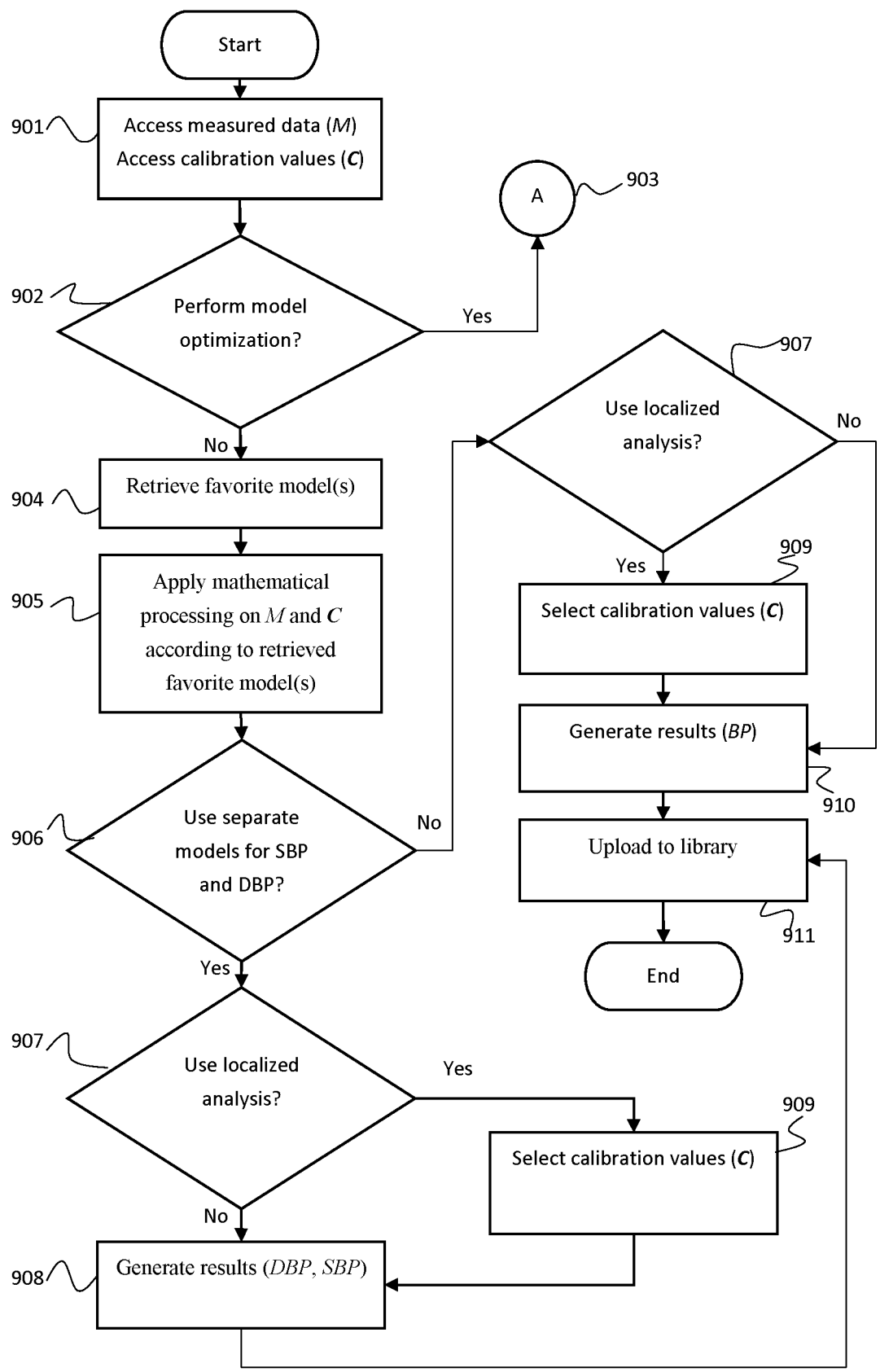
FIG. 9-A

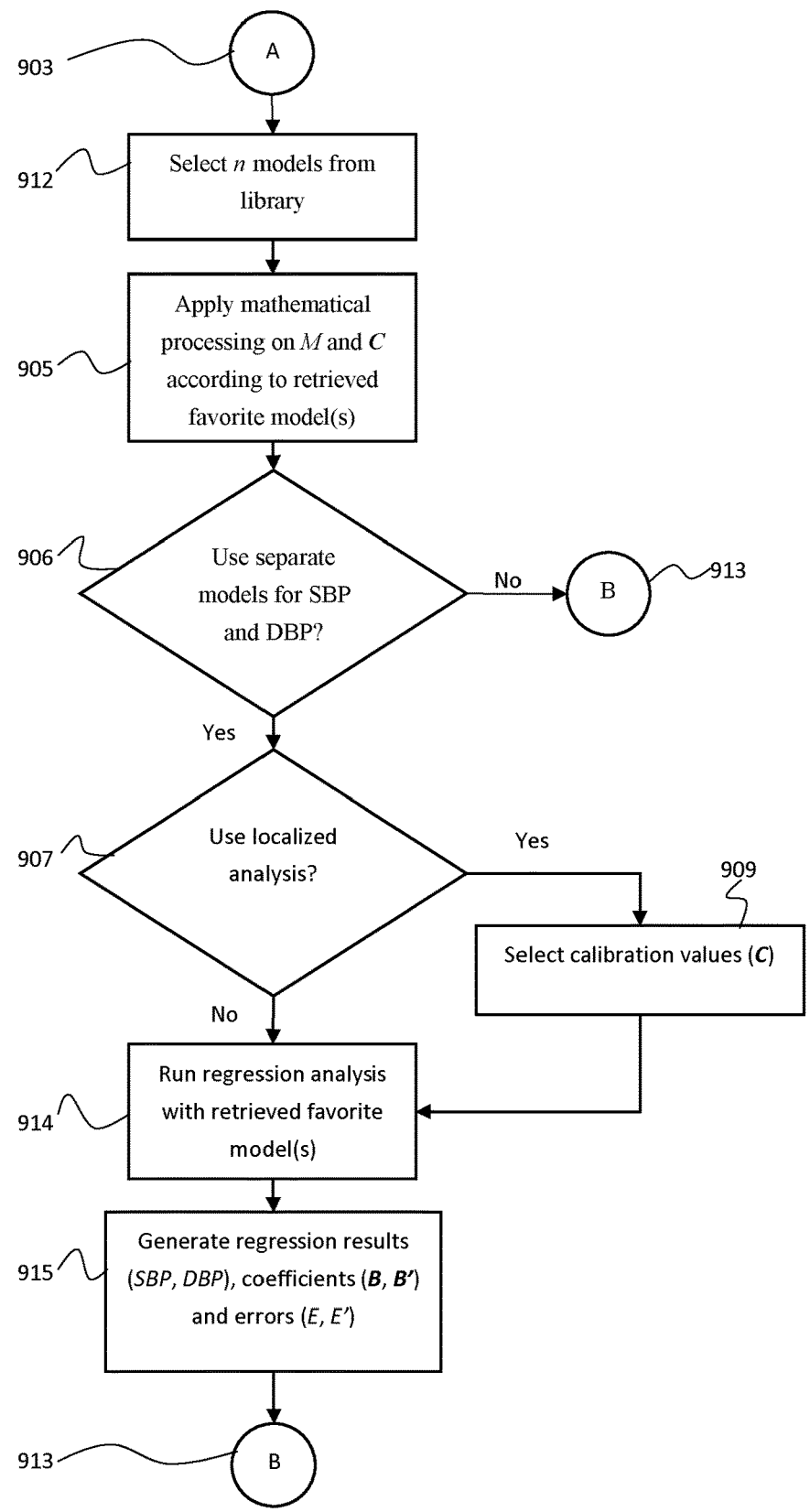
FIG. 9-B

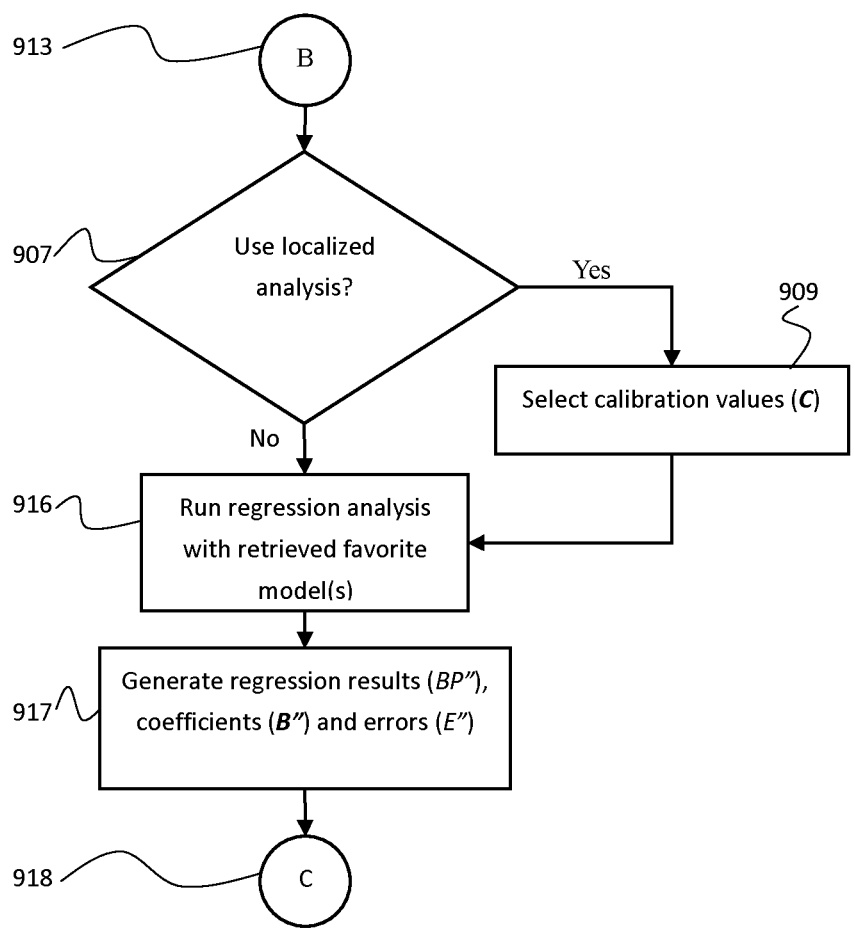
FIG.9-C

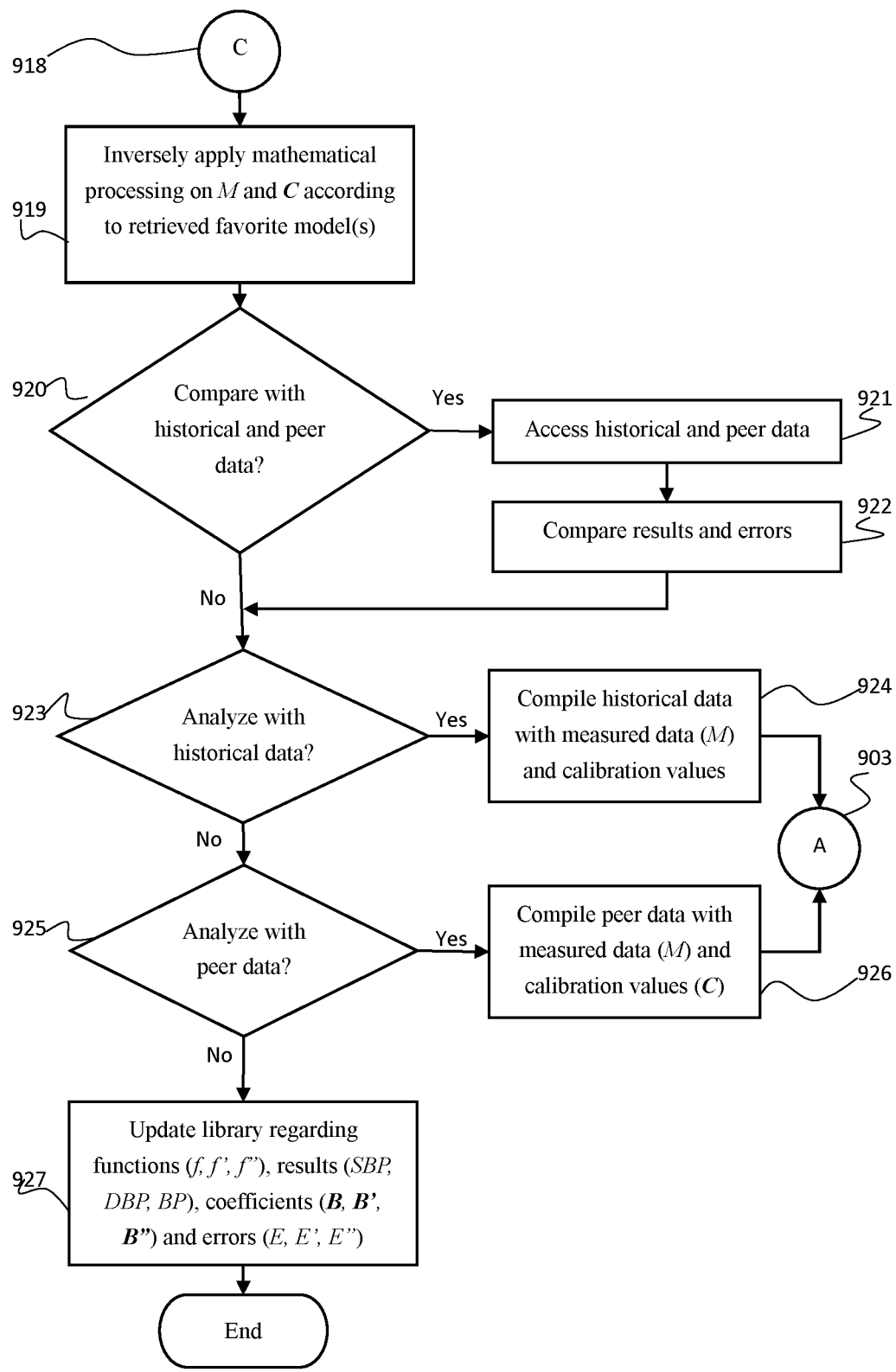
FIG. 9-D

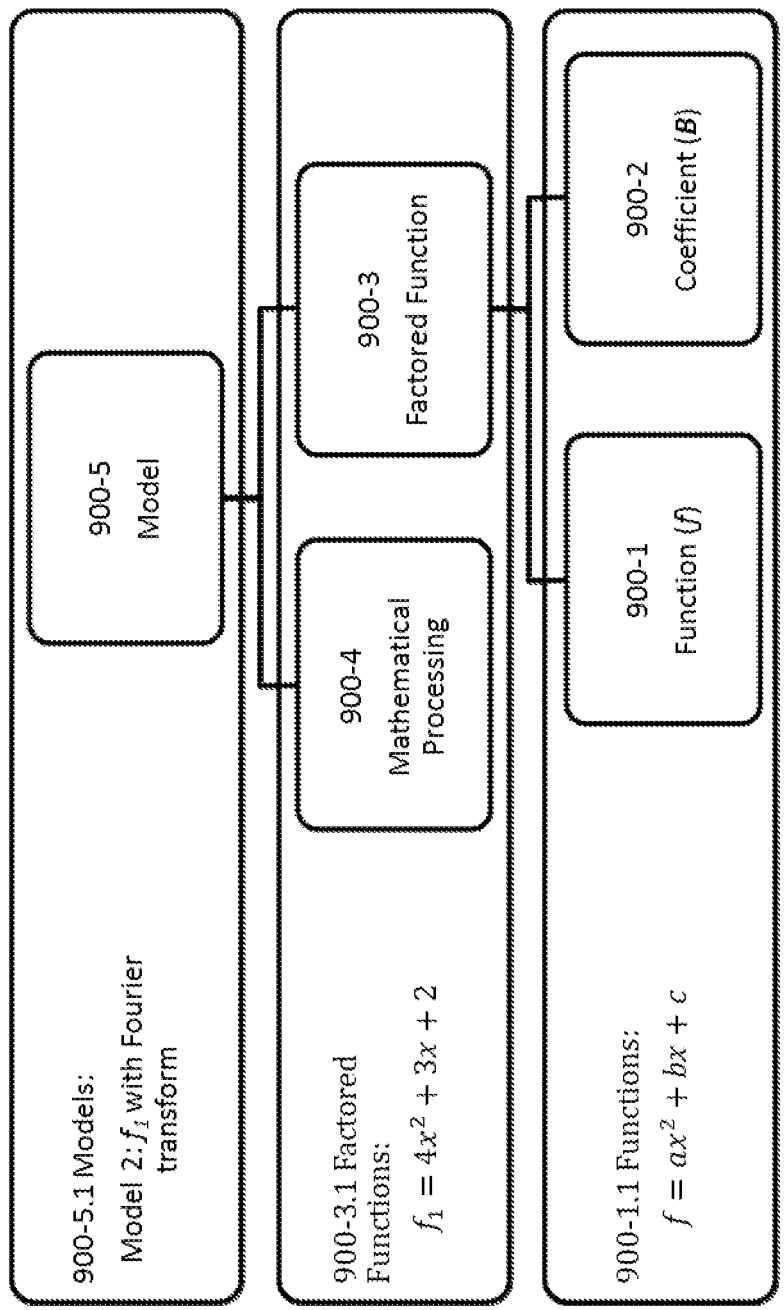
Fig. 9-E

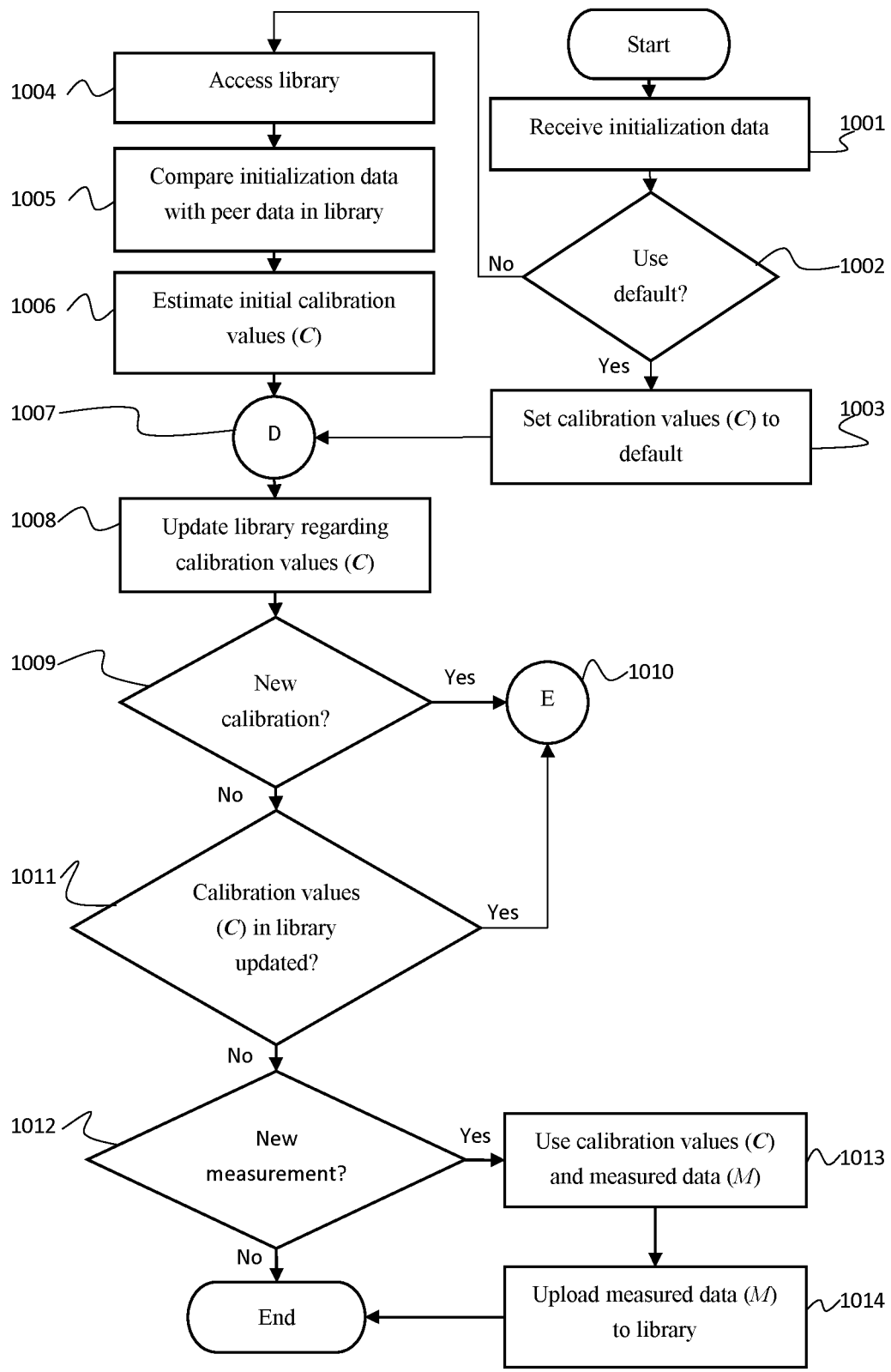
FIG. 10-A

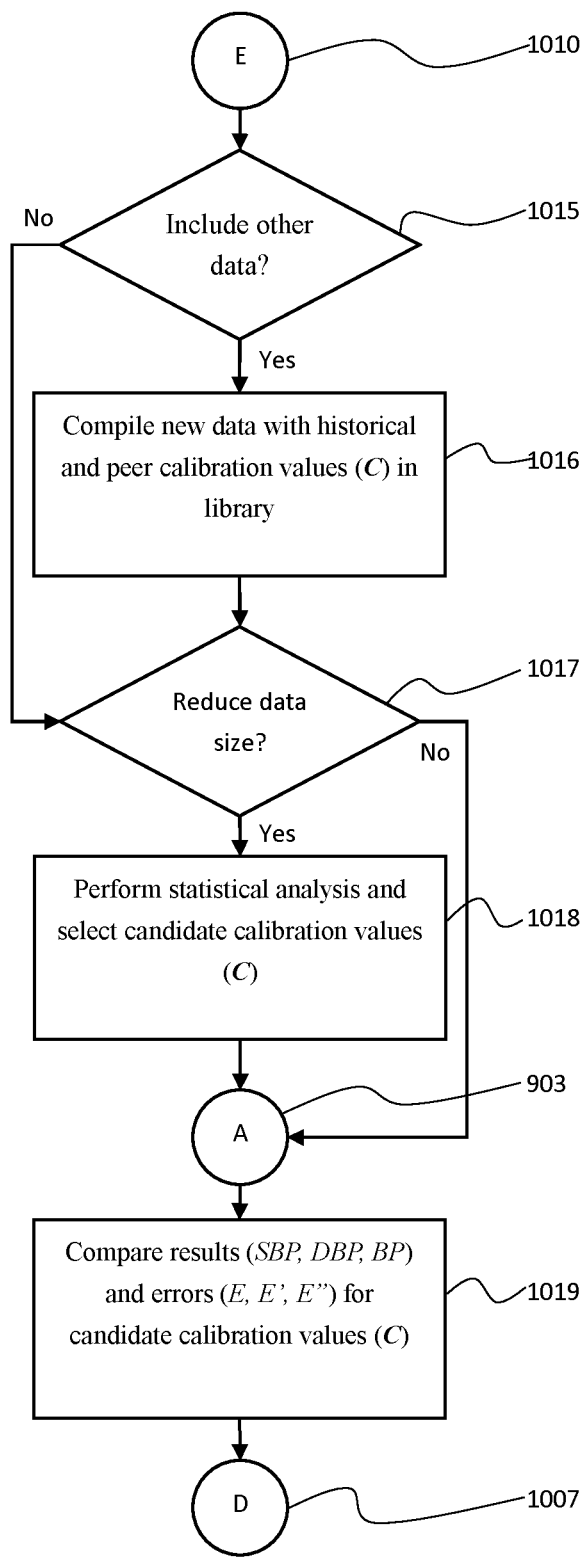
FIG. 10-B

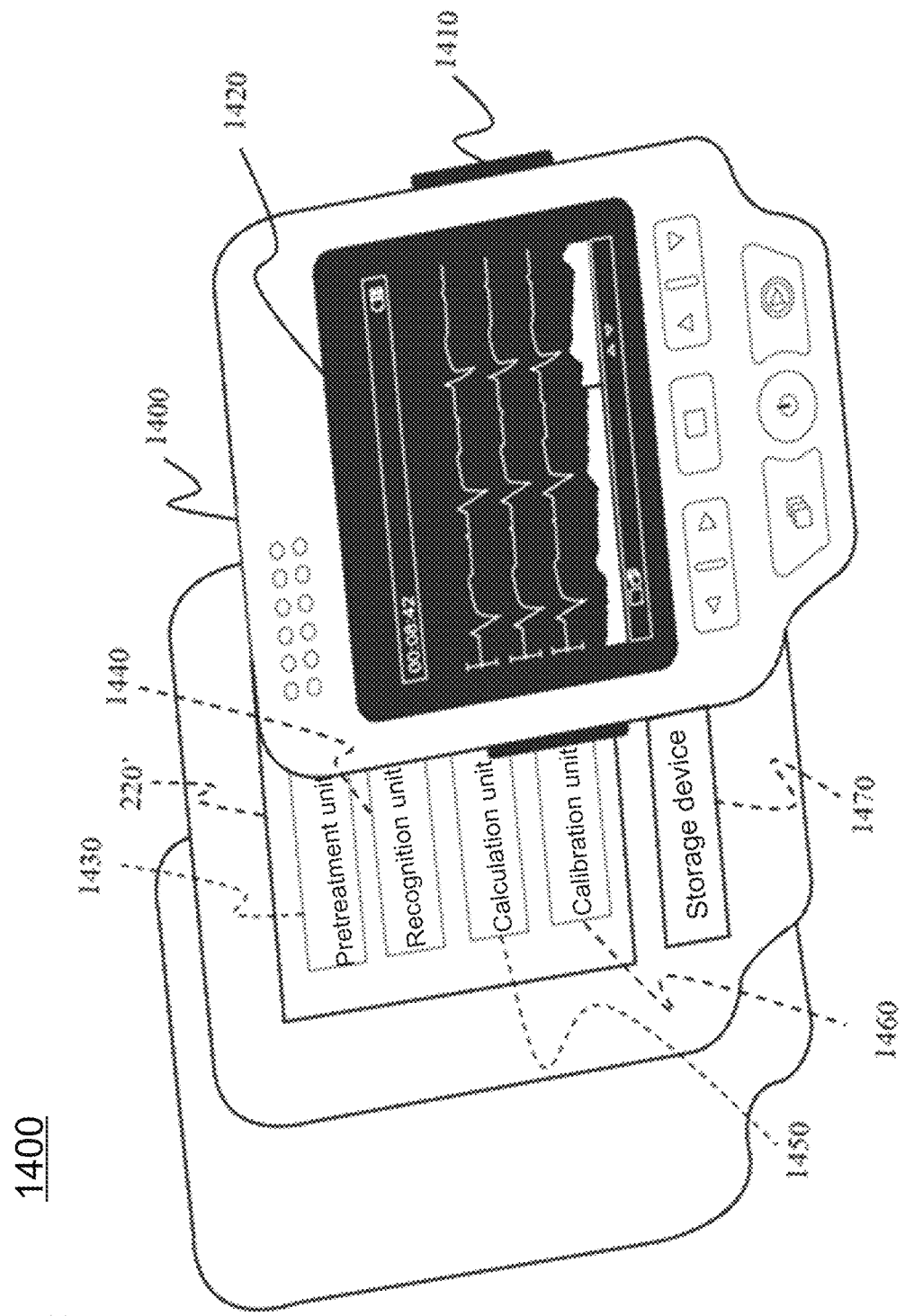
FIG. 14-A

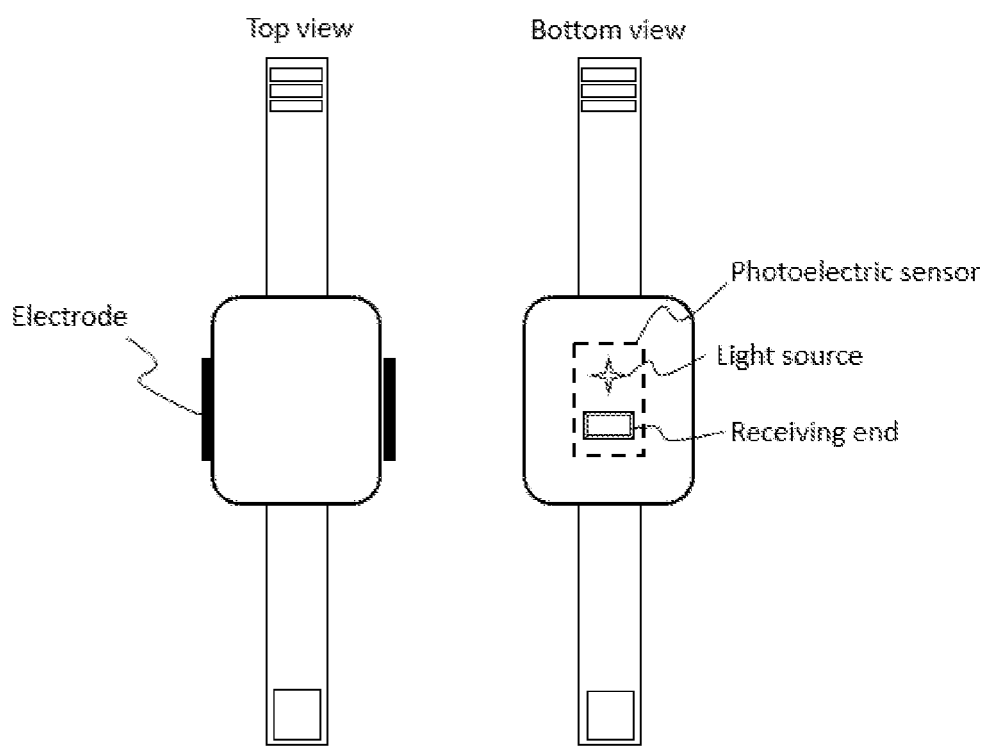
FIG. 14-B

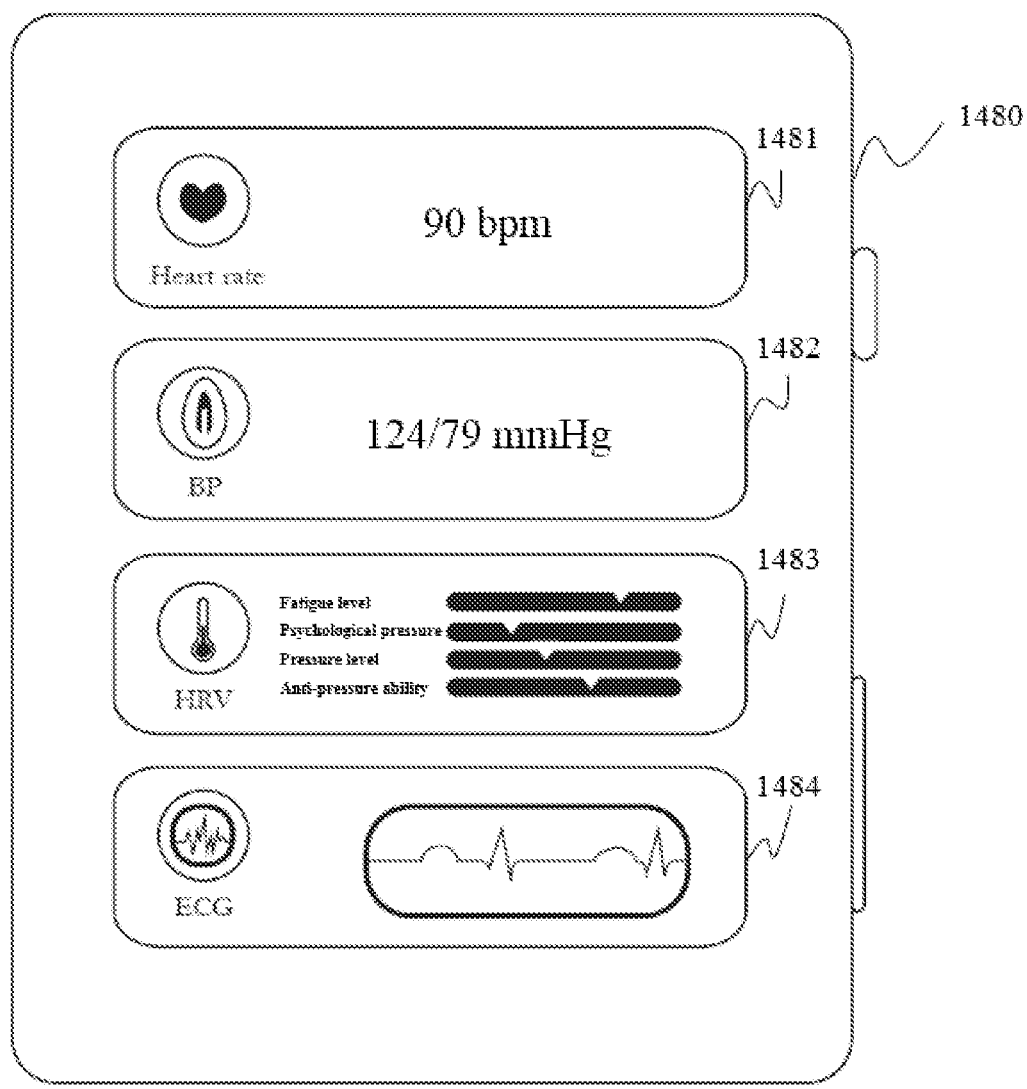
FIG. 14-C

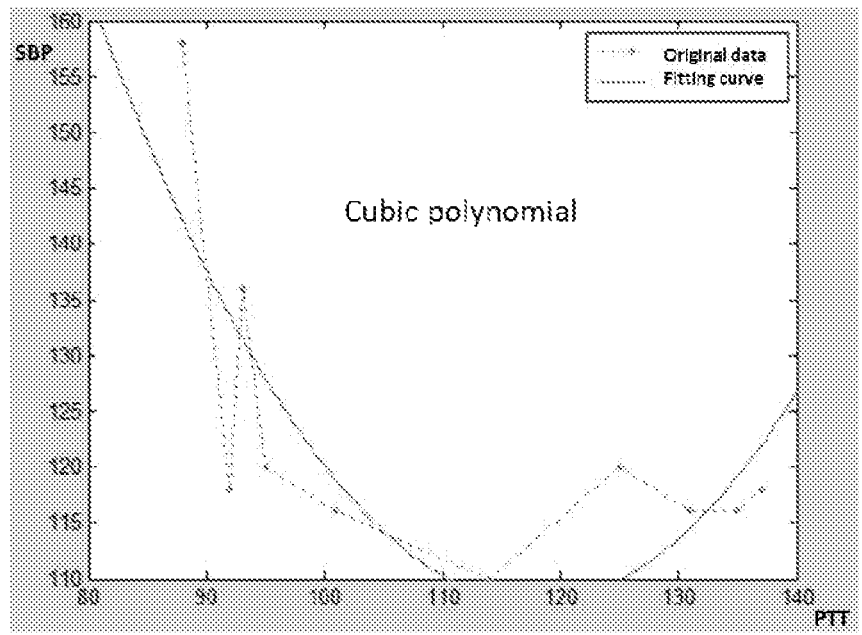
(a)
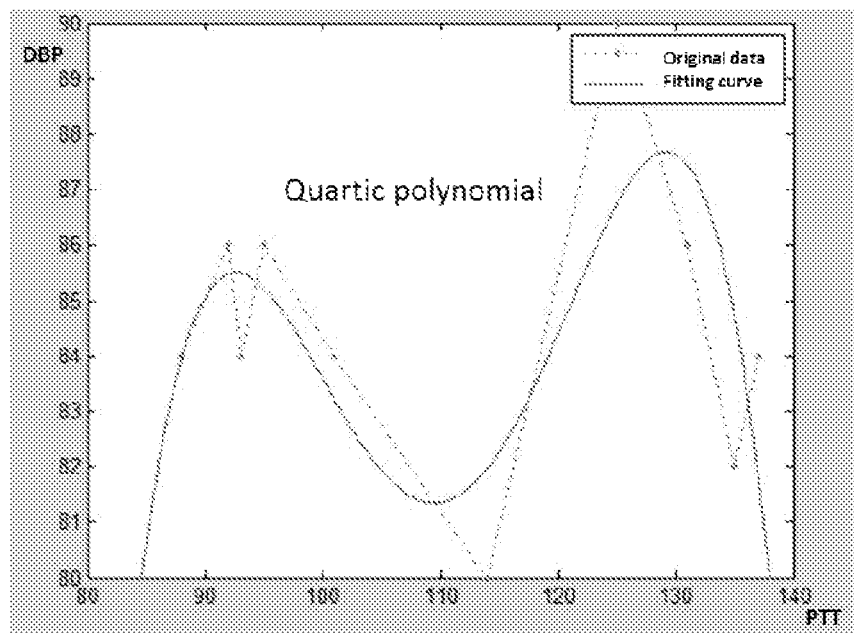
(b)
FIG. 15-A

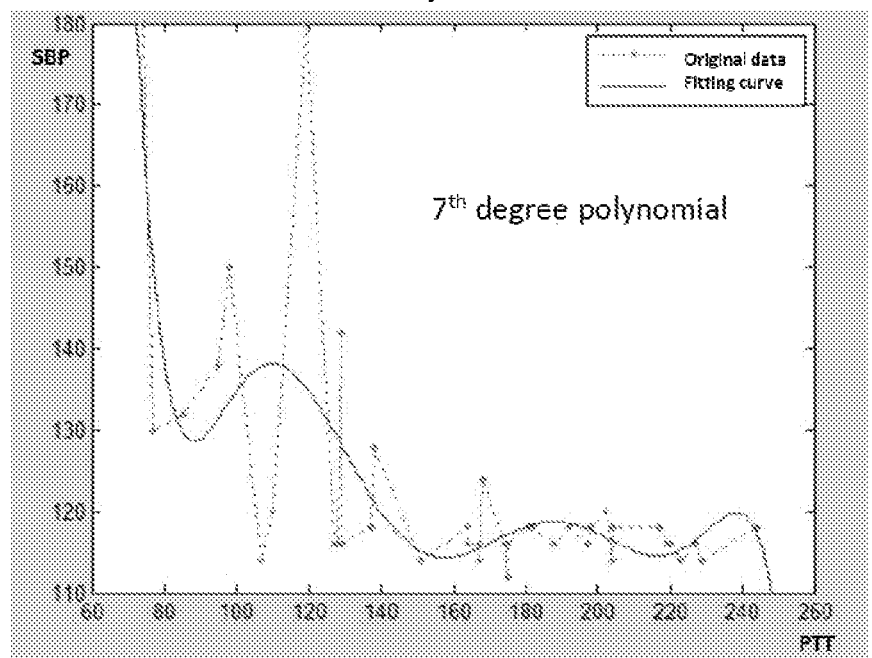
(a)
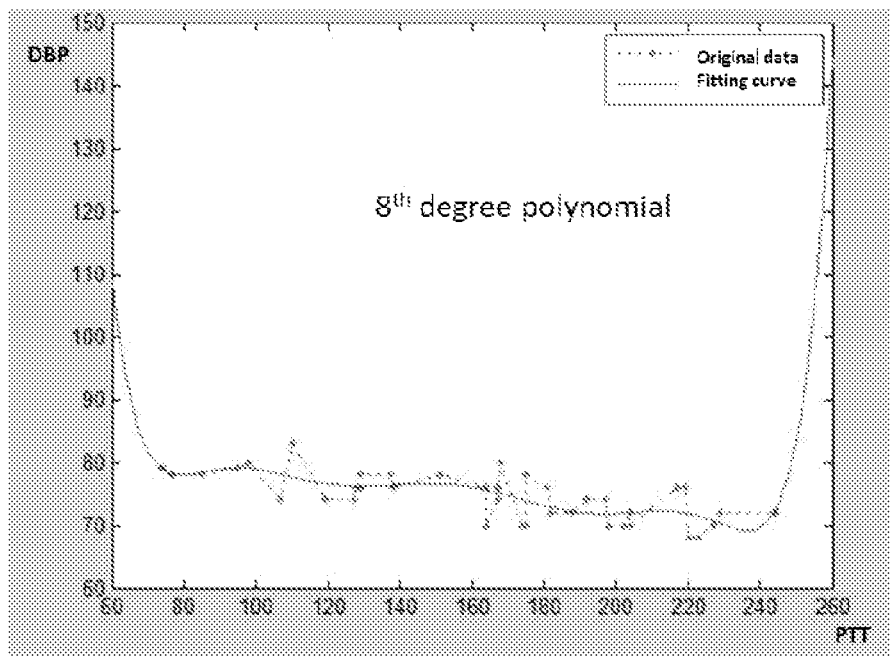
(b)
FIG. 15-B

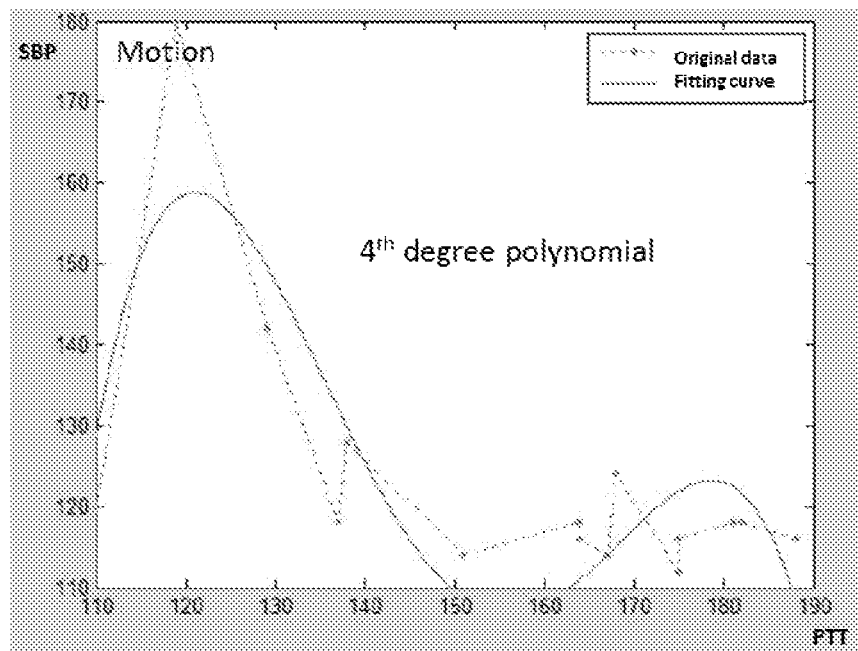
(a)
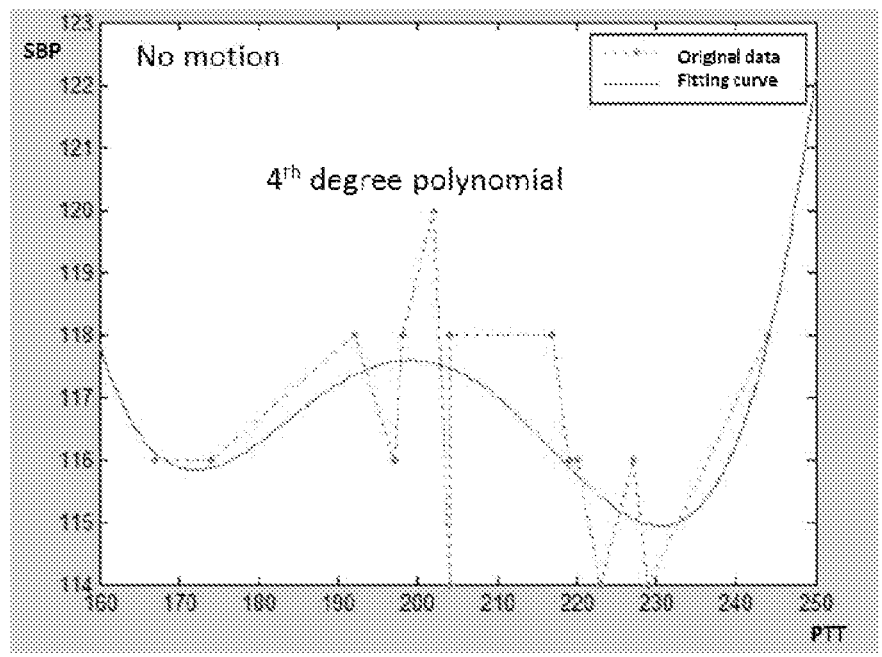
(b)
FIG. 15-C

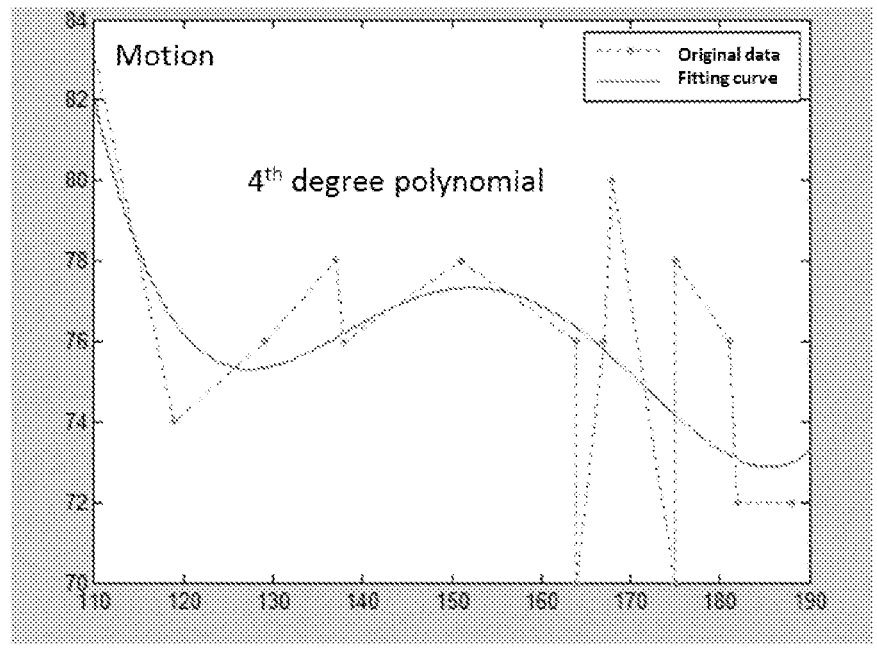
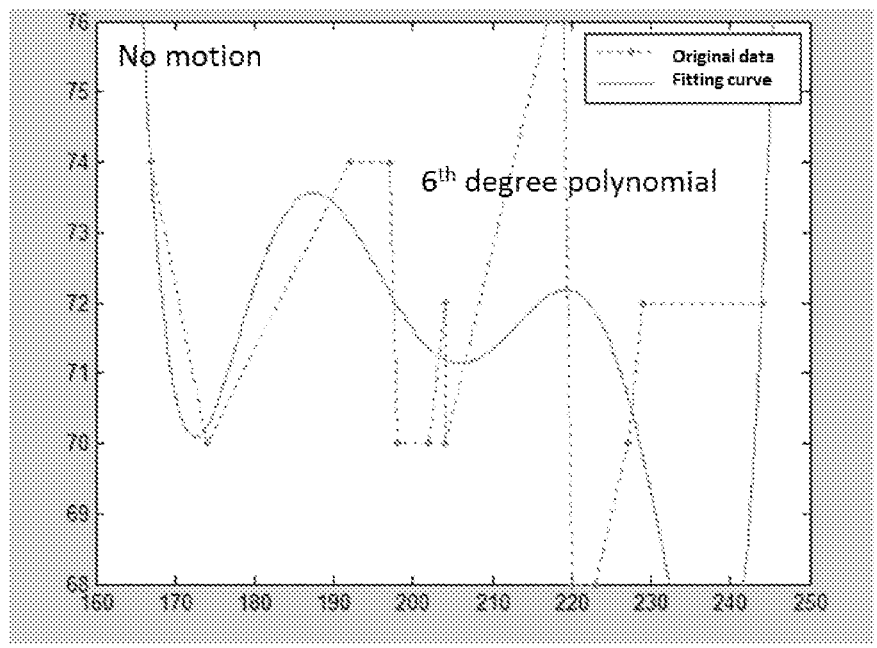
FIG. 15-D

SYSTEM AND METHOD FOR BLOOD PRESSURE MONITORING

CROSS-REFERENCE TO RELATED APPLICATIONS

This application is a U.S. national phase entry of International Application No. PCT/CN2015/083334, filed on Jul. 3, 2015, which claims priority of Chinese Application No. 201520188152.9, filed on Mar. 31, 2015, the entire contents of each of which are hereby incorporated by reference.

TECHNICAL FIELD

The present disclosure generally relates to a system and method applicable in health-care related areas. More particularly, the present disclosure relates to a system and method for blood pressure monitoring.

BACKGROUND

A traditional blood pressure measurement system, also called sphygmomanometers, employs Korotkoff sounds or an oscillometric method to determine blood pressure based on the relationship of the external pressure and magnitude of arterial volume pulsations. Such a traditional blood pressure measurement system involves an inflatable cuff to restrict blood flow. Various cuff-based methods work discontinuously with an interval of some minutes or longer between consecutive measurements. Currently, ambulatory blood pressure measurement and home blood pressure measurement are recommended by professional societies for hypertension management and cardiovascular risk prediction. However, such intermittent blood pressure measurements cannot capture the dynamic state of cardiovascular system throughout a day or even longer time period. Continuous and non-invasive blood pressure monitoring may allow the investigation of transient changes in blood pressure and thus may give insights into mechanisms of blood pressure control. There is a need for a system and method to monitor blood pressure continuously in a non-invasive and cuffless way with certain accuracy.

SUMMARY

Some embodiments of the present disclosure relates to a device including memory storing instructions, and at least one processor. The device may be used to calculate, estimate, or monitor the blood pressure of a subject. When the at least one processor executing the instructions, the at least one process may perform one or more of the following operations. A first signal representing heart activity the subject, or first information relating to or representing the first signal, may be received. A second signal representing time-varying information on at least one pulse wave of the subject, or second information relating to or representing the second signal, may be received. A first feature in the first signal may be identified. The identification of the first feature in the first signal may be achieved by analyzing the first information or the first signal. A second feature in the second signal may be identified. The identification of the second feature in the second signal may be achieved by analyzing the second information or the second signal. A pulse transit time based on a difference between the first feature and the second feature may be computed. The blood pressure of the subject may be calculated according to a first model based on the computed pulse transit time and a first set of calibration values, the first set of calibration values relating to the subject.

Some embodiments of the present disclosure relates to a method implemented on at least one processor for calculating, estimating, or monitoring the blood pressure of a subject. The method may include one or more of the following operations. A first signal representing heart activity of the subject, or first information relating to or representing the first signal, may be received. A second signal representing time-varying information on at least one pulse wave of the subject, or second information relating to or representing the second signal, may be received. A first feature in the first signal may be identified. The identification of the first feature in the first signal may be achieved by analyzing the first information or the first signal. A second feature in the second signal may be identified. The identification of the second feature in the second signal may be achieved by analyzing the second information or the second signal. A pulse transit time based on a difference between the first feature and the second feature may be computed. A blood pressure of the subject may be calculated according to a first model based on the computed pulse transit time and a first set of calibration values, the first set of calibration values relating to the subject.

Some embodiments of the present disclosure relates to a system implemented on memory and at least one processor. The system may be used to calculate, estimate, or monitoring the blood pressure of a subject. The system may include an acquisition module an analysis module. The acquisition module may be configured to receive a first signal representing heart activity of a subject (or first information relating to or representing the first signal), and a second signal representing time-varying information on at least one pulse wave of the subject (or second information relating to or representing the second signal). The analysis module may be configured to identify a first feature in the first signal; identify a second feature in the second signal; compute a pulse transit time based on a difference between the first feature and the second feature; and calculate a blood pressure of the subject according to a model based on the computed pulse transit time and a first set of calibration values, the first set of calibration values relating to the subject. The identification of the first feature in the first signal may be achieved by analyzing the first information or the first signal. The identification of the second feature in the second signal may be achieved by analyzing the second information or the second signal. The system may further include an output module configured to provide the calculated blood pressure for output.

In some embodiments, receiving the first signal may include communicating with a first sensor configured to acquire the first signal at a first location on the body of the subject. Receiving the first signal may include measuring or acquiring the first signal using a first sensor configured to acquire the first signal at a first location on the body of the subject. The first sensor may be part of the device. The receiving the second signal may include communicating with a first sensor configured to acquire the first signal at a first location on the body of the subject. The receiving the second signal may include communicating with a first sensor configured to acquire the first signal at a first location on the body of the subject. The second sensor may be part of the device. The first location and the second location may be substantially the same. The first location and the second location may be on an arm of the subject. The first location and the second location may be on the wrist of a same arm of the subject. The first location and the second location may be on different parts of the subject. The device may include a structure that allows the device to be worn by the subject.

In some embodiments, the first signal may include an optical signal or an electrical signal. The second signal may include an optical signal or an electrical signal. The first signal or the second signal may include a photoplethysmography (PPG) waveform, an electrocardiography (ECG) waveform, or a ballistocardiogram (BCG) waveform.

In some embodiments, the first feature of the first signal may correspond to a first time point. The identifying the second feature may include selecting a segment of the second signal, the segment occurring within a time window from the first time point; and locating the second feature corresponding to a second time point in the segment. The computing the pulse transit time may include determining a time interval between the first time point and the second time point. The time window may be constant independent of a specific measurement. For instant, the time window may be equal to or less than 2 seconds. The time window may be determined based on, a condition of the subject, e.g., the heart rate of the subject at or around the acquisition time (as defined elsewhere in the present disclosure). For instance, the at least one processor may perform the operations including determining a heart rate of the subject.

In some embodiments, if the pulse transit time is determined based on an ECG waveform and a PPG waveform, and the at least one processor may determine the time window based on the heart rate. If the pulse transit time is determined based on an ECG waveform and a PPG waveform, the segment on the PPG waveform that correspond to the time between two consecutive QRS waves (e.g., two consecutive peak points) on the ECG waveform may be analyzed to identify a feature to be used in determining the pulse transit time.

In some embodiments, the first set of calibration values may include a first calibration pulse transit time. The at least one processor may perform the operations including determining a first variation between the first pulse transit time and the computed pulse transit time; and determining that the first variation is equal to or lower than a first threshold. The at least one processor may cause the device or a portion thereof to communicate with a library storing a plurality of sets of calibration values. The at least one processor may retrieve from a plurality of sets of calibration values (from, e.g., the library), a second set of calibration values. The second set of calibration values may include a second calibration pulse transit time. The at least one processor may derive the first model used to calculate the blood pressure of the subject based on the first set of calibration values and the second set of calibration values. The second variation is equal to or lower than a second threshold. Retrieving the second set of calibration values may include determining a second variation between the second calibration pulse transit time and the computed pulse transit time; and determining that the second variation is equal to or lower than the second threshold. The second threshold may be the same or different from the first threshold. The value of the first threshold may depend on the pulse transit time of a specific measurement. For instance, the value of the first threshold may be 2%, or 5%, or 10%, or 15%, or 20% of the pulse transit time of a specific measurement. In a specific measurement, the first set of calibration data, among a plurality of sets of calibration data available for the subject, may be one whose calibration pulse transit time is closest to the pulse transit time of the specific measurement.

For a same subject, the systolic blood pressure (SBP) and diastolic blood pressure (DBP) may be calculated based on a same model or different models. A same model may be used to calculate SBP of two or more subjects. Different models may be used to calculate SBP of two or more subjects. A same model may be used to calculate DBP of two or more subjects. Different models may be used to calculate DBP of two or more subjects. A model may be specific to an individual subject.

In some embodiments, the at least one processor may further receive information relating to the subject or a condition when the first signal or the second signal is acquired. Exemplary information may include, e.g., age, body weight, the time (during the day) or the date the first signal or the second signal is acquired, the room temperature, the mood of the subject at the time, whether the subject has recently exercised, or the like, or a combination thereof. Such information may be taken into consideration when the blood pressure of the subject is calculated using the device.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein:

FIG. 9-A through FIG. 9-D provide exemplary mathematical models and optimization processes according to some embodiments of the present disclosure;

FIG. 9-E illustrates the relationship between a function, a factored function, and a model;

FIG. 10-A and FIG. 10-B provide exemplary calibration processes according to some embodiments of the present disclosure;

FIG. 14-A illustrates an exemplary device according to some embodiments of the present disclosure;

FIG. 14-B illustrates an exemplary device according to some embodiments of the present disclosure;

FIG. 14-C illustrates an exemplary interface of a device according to some embodiments of the present disclosure; and FIG. 15-A through FIG. 15-D illustrates estimations of exemplary mathematical models according to some embodiments of the present disclosure.

DETAILED DESCRIPTION

Figure 1:
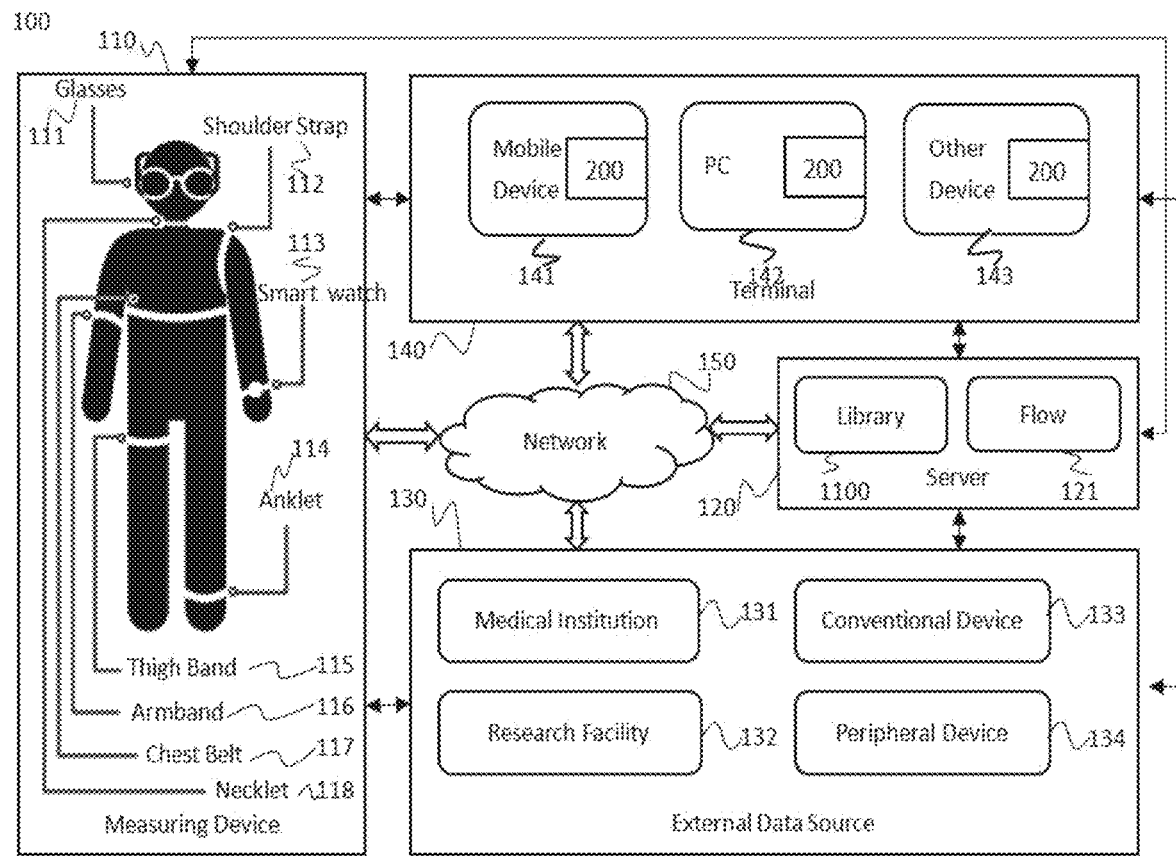
FIG. 1 illustrates an exemplary system configuration in which a system for monitoring a physiological signal may be deployed in accordance with various embodiments of the present disclosure.

In the following detailed description, numerous specific details are set forth by way of examples in order to provide a thorough understanding of the relevant disclosure. However, it should be apparent to those skilled in the art that the present disclosure may be practiced without such details. In other instances, well known methods, procedures, systems, components, and/or circuitry have been described at a relatively high-level, without detail, in order to avoid unnecessarily obscuring aspects of the present disclosure.

The present disclosure relates to system, method, and programming aspects of blood pressure monitoring. The blood pressure monitoring may involve a cuffless system and method. In some embodiments, blood pressure is estimated based on pulse wave related information, e.g., pulse transit time (PTT), pulse arrival time (PAT), or the like, or a combination thereof. The system and method involve improved sensor design and signal processing. The system and method as disclosed herein may perform blood pressure monitoring continuously in a non-invasive way, with improved accuracy. The following description is provided with reference to PTT in connection with the blood pressure monitoring for illustration purposes, and is not intended to limit the scope of the present disclosure. Merely by way of example, the system and method as disclosed herein may utilize one or more other pulse wave related information or signals, e.g., PAT, for blood pressure monitoring.

These and other features, and characteristics of the present disclosure, as well as the methods of operation and functions of the related elements of structure and the combination of parts and economies of manufacture, may become more apparent upon consideration of the following description with reference to the accompanying drawing(s), all of which form a part of this specification. It is to be expressly understood, however, that the drawing(s) are for the purpose of illustration and description only and are not intended to limit the scope of the present disclosure. As used in the specification and in the claims, the singular form of "a", "an", and "the" include plural referents unless the context clearly dictates otherwise.

FIG. 1 illustrates an exemplary system configuration in which a system 100 may be deployed in accordance with some embodiments of the present disclosure. The system 100 may be configured to monitor a physiological parameter of interest. The system 100 may include a measuring device 110, a database (e.g., a server 120), an external data source 130, and a terminal 140. Various components of the system 100 may be connected to each other directly or indirectly via a network 150.

The measuring device 110 may be configured to measure a signal. The signal may be a cardiovascular signal. The signal may relate to or be used to calculate or estimate a physiological parameter of interest. The measuring device 110 may include, for example, a clinical device, a household device, a portable device, a wearable device, or the like, or a combination thereof. As used herein, a clinical device may be one that meets applicable requirements and specifications to be used in a clinical setting including, e.g., a hospital, a doctor's office, a nursing home, or the like. A clinical device may be used by or with the assistance of a healthcare provider. As used herein, a household device may be one that meets applicable requirements and specifications to be used at home or a nonclinical setting. A household device may be used by someone who is or is not a professional provider. A clinical device or a household device, or a portion thereof, may be portable or wearable. Exemplary clinical devices include an auscultatory device, an oscillometric device, an ECG monitor, a PPG monitor, or the like, or a combination thereof. Exemplary household devices include an oscillometric device, a household ECG monitor, a sphygmometer, or the like, or a combination thereof. Exemplary portal devices include an oscillometric device, a portable ECG monitor, a portable PPG monitor, or the like, or a combination thereof. Exemplary wearable devices include a pair of glasses 111, a shoulder strap 112, a smart watch 113, an anklet 114, a thigh band 115, an armband 116, a chest belt 117, a necklet 118, or the like, or a combination thereof. The above mentioned examples of measuring devices 110 are provided for illustration purposes, and not intended to limit the scope of the present disclosure. A measuring device 110 may be in other forms, such as a fingerstall, a wristband, a brassiere, an underwear, a chest band, or the like, or a combination thereof.

Merely by way of example, the measuring device 110 is a wearable or portable device configured to measure one or more cardiovascular signals. In some embodiments, the wearable or portable device may process at least some of the measured signals, estimate a physiological parameter of interest based on the measured signals, display a result including the physiological parameter of interest in the form of, e.g., an image, an audio alert, perform wired or wireless communication with another device or server (e.g., the server 120), or the like, or a combination thereof. In some embodiments, the wearable or portable device may communicate with another device (e.g., the terminal 140) or a server (e.g., a cloud server). The device or server may process at least some of the measured signals, estimate a physiological parameter of interest based on the measured signals, display a result including the physiological parameter of interest in the form of, e.g., an image, an audio alert, or the like, or a combination thereof.

In some embodiments, the operations of processing the measured signals, estimating a physiological parameter, displaying a result, or performing wired or wireless communication may be performed by an integrated device or by separate devices connected to or communicating with each other. Such an integrated device may be portable or wearable. In some embodiments, at least some of the separate devices may be portable or wearable, or located in the vicinity of a subject whose signal is measured or a physiological parameter of interest is estimated or monitored.

Merely by way of example, the subject wears the measuring device 110 that is configured to measure one or more cardiovascular signals; the measured one or more cardiovascular signals are transmitted to a smart phone that is configured to calculate or estimate a physiological parameter of interest based on the measured signals. In some embodiments, at least some of the separate devices are located in a location remote from the subject. Merely by way of example, the subject wears the measuring device 110 that is configured to measure one or more cardiovascular signals; the measured one or more cardiovascular signals are transmitted to a server that is configured to calculate or estimate a physiological parameter of interest based on the measured signals; the calculated or estimated physiological parameter of interest may be transmitted back to the subject, or a user other than the subject (e.g., a doctor, a care provider, a family member relating to the subject, or the like, or a combination thereof).

In some embodiments, the measuring devices 110 may incorporate various types of sensors, e.g., an electrode sensor, an optical sensor, a photoelectric sensor, a pressure sensor, an accelerometer, a gravity sensor, a temperature sensor, a moisture sensor, or the like, or a combination thereof. The measuring device may be configured to monitor and/or detect one or more types of variables including, for example, temperature, humidity, user or subject input, or the like, or a combination thereof. The measuring devices 110 may also incorporate a positioning system, e.g., a GPS receiver, or a location sensor, and the position information may be transmitted to the server 120, the external data source 130, the terminal 140, or the like, or a combination thereof, through the network 150. The position information and measured signals may be transmitted simultaneously or successively.

The system may include or communicate with a server or a database configured for storing a library 1100 and algorithms 121. The server or database may be the server 120. The server 120 may be a cloud server. Merely by way of example, the server 120 may be implemented in a cloud server that may provide storage capacity, computation capacity, or the like, or a combination thereof. The library 1100 may be configured to collect or store data. The data may include personal data, non-personal data, or both. The data may include static data, dynamic data, or both. Exemplary static data may include various information regarding a subject including identity, contact information, birthday, a health history (e.g., whether a subject has a history of smoking, information regarding a prior surgery, a food allergy, a drug allergy, a medical treatment history, a history of genetic disease, a family health history, or the like, or a combination thereof), the gender, the nationality, the height, the weight, the occupation, a habit (e.g., a health-related habit such as an exercise habit), the education background, a hobby, the marital status, religious belief, or the like, or a combination thereof. Exemplary dynamic data may include a current health condition of a subject, medications the subject is taking, a medical treatment the subject is undertaking, diet, physiological signals or parameters (e.g., pulse transit time (PTT), systolic blood pressure (SBP), diastolic blood pressure (DBP), or the like) relating to the subject for multiple time points or over a period of time, or the like, or a combination thereof.

As used herein, a subject may refer to a person or animal whose signal or information is acquired and whose physiological parameter is acquired, estimated, or monitored. Merely by way of example, a subject may be a patient whose cardiovascular signals are acquired, and blood pressure estimated or monitored based on the acquired cardiovascular signals.

Figure 11:
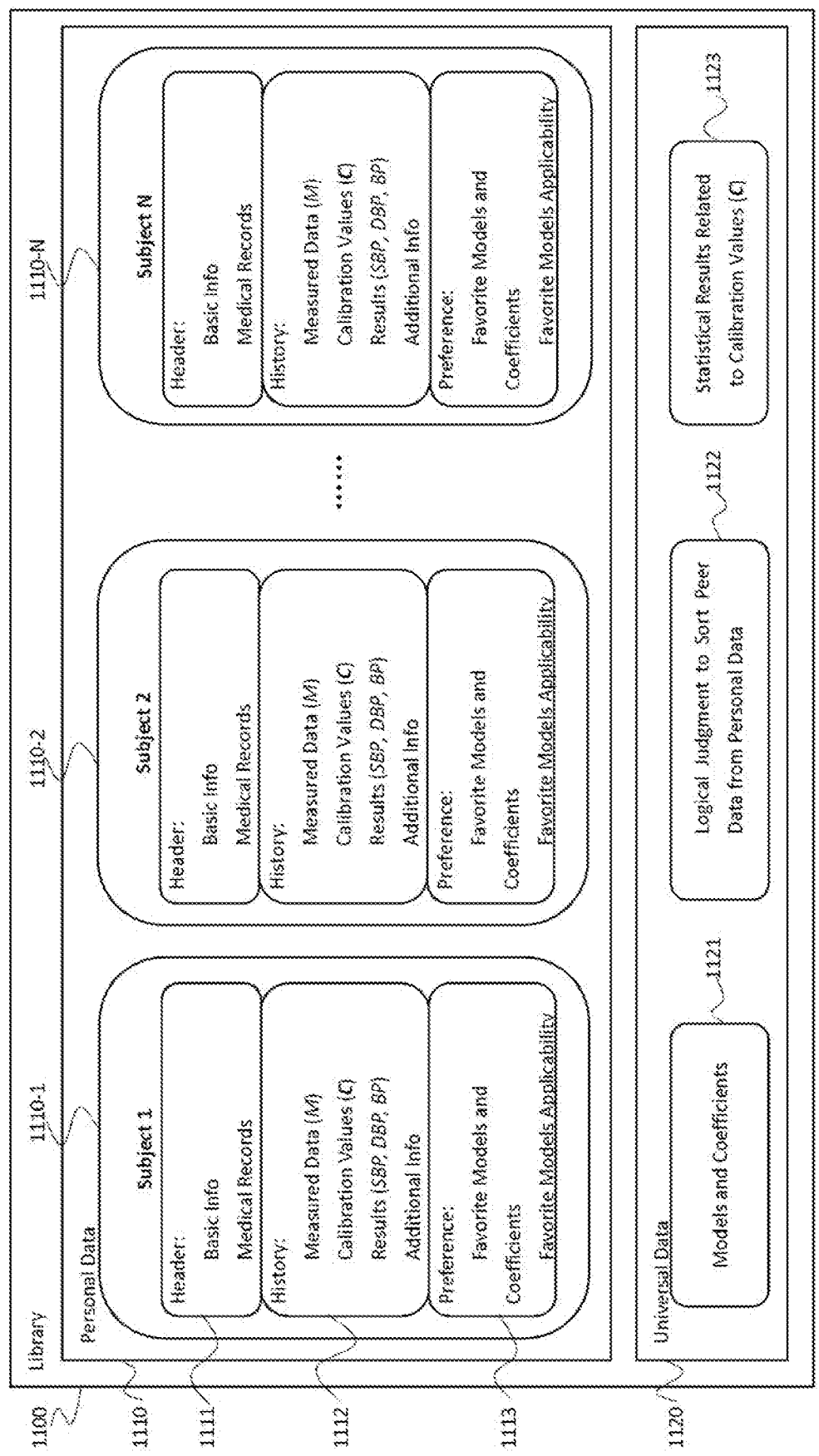
FIG. 11 illustrates an exemplary library according to some embodiments of the present disclosure.

Detailed descriptions regarding a library 1100 are provided in connection with FIG. 11. One or more algorithms 121 in the server 120 may be applied in data processing or analysis, as described elsewhere in the present disclosure. The description of the server 120 above is provided for illustration purposes, and not intended to limit the scope of the present disclosure. The server 120 may have a different structure or configuration. For example, algorithms 121 are not stored in the server 120; instead, algorithms 121 may be stored locally at the terminal 140. Furthermore, a library 1100 may also be stored at the terminal 140.

The external data sources 130 may include a variety of organizations, systems, and devices, or the like, or a combination thereof. Exemplary data sources 130 may include a medical institution 131, a research facility 132, a conventional device 133, and a peripheral device 134, or the like, or a combination thereof. The medical institution 131 or the research facility 132 may provide, for example, personal medical records, clinical test results, experimental research results, theoretical or mathematical research results, algorithms suitable for processing data, or the like, or a combination thereof. The conventional device 133 may include a cardiovascular signal measuring device, such as a mercury sphygmomanometer. A peripheral device 134 may be configured to monitor and/or detect one or more types of variables including, for example, temperature, humidity, user or subject input, or the like, or a combination thereof. The above mentioned examples of the external data sources 130 and data types are provided for illustration purposes, and not intended to limit the scope of the present disclosure. For instance, the external data sources 130 may include other sources and other types of data, such as genetic information relating to a subject or his family.

The terminal 140 in the system 100 may be configured for processing at least some of the measured signals, estimating a physiological parameter of interest based on the measured cardiovascular signals, displaying a result including the physiological parameter of interest in the form of, e.g., an image, storing data, controlling access to the system 100 or a portion thereof (e.g., access to the personal data stored in the system 100 or accessible from the system 100), managing input-output from or relating to a subject, or the like, or a combination thereof. The terminal 140 may include, for example, a mobile device 141 (e.g., a smart phone, a tablet, a laptop computer, or the like), a personal computer 142, other devices 143, or the like, or a combination thereof. Other devices 143 may include a device that may work independently, or a processing unit or processing module assembled in another device (e.g., an intelligent home terminal). Merely by way of example, the terminal 140 includes a CPU or a processor in a measuring device 110. In some embodiments, the terminal 140 may include an engine 200 as described in FIG. 2, and the terminal 140 may also include a measuring device 110.

The network 150 may be a single network or a combination of different networks. For example, the network 150 may be a local area network (LAN), a wide area network (WAN), a public network, a private network, a proprietary network, a Public Telephone Switched Network (PSTN), the Internet, a wireless network, a virtual network, or any combination thereof. The network 150 may also include various network access points, e.g., wired or wireless access points such as base stations or Internet exchange points (not shown in FIG. 1), through which a data source or any component of the system 100 described above may connect to the network 150 in order to transmit information via the network 150.

Various components of or accessible from the system 100 may include a memory or electronic storage media. Such components may include, for example, the measuring device 110, the server 120, the external data sources 130, the terminal 140, peripheral equipment 240 discussed in connection with FIG. 2, or the like, or a combination thereof. The memory or electronic storage media of any component of the system 100 may include one or both of a system storage (e.g., a disk) that is provided integrally (i.e. substantially non-removable) with the component, and a removable storage that is removably connectable to the component via, for example, a port (e.g., a USB port, a firewire port, etc.) or a drive (e.g., a disk drive, etc.). The memory or electronic storage media of any component of the system 100 may include or be connectively operational with one or more virtual storage resources (e.g., cloud storage, a virtual private network, and/or other virtual storage resources).

The memory or electronic storage media of the system 100 may include a dynamic storage device configured to store information and instructions to be executed by the processor of a system-on-chip (SoC, e.g., a chipset including a processor), other processors (or computing units), or the like, or a combination thereof. The memory or electronic storage media may also be used to store temporary variables or other intermediate information during execution of instructions by the processor(s). Part of or the entire memory or electronic storage media may be implemented as Dual In-line Memory Modules (DIMMs), and may be one or more of the following types of memory: static random access memory (SRAM), Burst SRAM or SynchBurst SRAM (BSRAM), dynamic random access memory (DRAM), Fast Page Mode DRAM (FPM DRAM), Enhanced DRAM (EDRAM), Extended Data Output RAM (EDO RAM), Extended Data Output DRAM (EDO DRAM), Burst Extended Data Output DRAM (BEDO DRAM), Enhanced DRAM (EDRAM), synchronous DRAM (SDRAM), JEDECSRAM, PCIOO SDRAM, Double Data Rate SDRAM (DDR SDRAM), Enhanced SDRAM (ESDRAM), SyncLink DRAM (SLDRAM), Direct Rambus DRAM (DRDRAM), Ferroelectric RAM (FRAM), or any other type of memory device. The memory or electronic storage media may also include read-only memory (ROM) and/or another static storage device configured to store static information and instructions for the processor of the SoC and/or other processors (or computing units). Further, the memory or electronic storage media may include a magnetic disk, optical disc or flash memory devices to store information and instructions.

In some embodiments, the SoC may be part of a core processing or computing unit of a component of or accessible from the system 100. The SoC may be configured to receive and process input data and instructions, provide output and/or control other components of the system. In some embodiments, the SoC may include a microprocessor, a memory controller, a memory, and a peripheral component. The microprocessor may further include a cache memory (e.g., SRAM), which along with the memory of the SoC may be part of a memory hierarchy to store instructions and data. The microprocessor may also include one or more logic modules such as a field programmable gate array (FPGA) or other logic array. Communication between the microprocessor in the SoC and memory may be facilitated by the memory controller (or chipset), which may also facilitate in communicating with the peripheral component, such as a counter-timer, a real-time timer, a power-on reset generator, or the like, or a combination thereof. The SoC may also include other components including, but not limited to, a timing source (e.g., an oscillator, a phase-locked loop, or the like), a voltage regulator, a power management circuit, or the like, or a combination thereof.

Merely by way of example, the system 100 may include a wearable or portable device. The wearable or portable device may include a SoC and a plurality of sensors. Exemplary sensors may include a photoelectric sensor, a conductance sensor, or the like, or a combination thereof. The SoC may process signals acquired through at least some of the plurality of sensors. The acquired signals may be various physiological signals, including, for example, photoplethysmograph (PPG), electrocardiograph (ECG), or the like, or a combination thereof. The SoC may calculate a physiological parameter of interest based on the acquired signals. Exemplary physiological parameters of interest may be blood pressure, or the like, or a combination thereof.

In some embodiments, the external data source 130 may receive data from the measuring device 110, the sever 120, the terminal 140, or the like, or any combination by the network 150. Merely by way of example, the external data source 130 (e.g., a medical institution, or a smart home system, or the like) may receive information relating to a subject (e.g., location information, data from the cloud sever or a terminal, or the like, or a combination thereof) based on the data received from the measuring devices 110 or the terminals 140. In some other embodiments, the measuring device 110 may receive data from the sever 120, the external data source 130, or the like, or any combination, via the network 150. Merely by way of example, the measuring device 110 may receive the information relating to a subject (e.g., a current/historical health condition of a subject, medications the subject is taking, medical treatment the subject is undertaking, current/historical diets, current emotion status, historical physiological parameters (e.g., PTT, SBP, DBP) relating to the subject, or the like, or a combination thereof). Furthermore, the terminal 140 may receive data from the measuring device 110, the server 120, the external data source 130, or the like, or a combination thereof.

FIG. 1 is a specific example of the system 100, and the configuration of the system 100 is not limited to that illustrated in FIG. 1. For example, a server 120 may be omitted, migrating all of its functions to a terminal 140. In another example, a server 120 and a terminal 140 may both be omitted, migrating all of their functions to a measuring device 110. The system may include various devices or combinations of devices in different embodiments.

In an example, the system may include a wearable or portable device and a mobile device (e.g., a smart phone, a tablet, a laptop computer, or the like). The wearable or portable device may be used to acquire physiological signals, environmental information, or the like, or a combination thereof. The mobile device may be used to receive the signals or information acquired by the wearable or portable device. The mobile device may calculate one or more physiological parameters of interest based on the acquired signals or information, as well as relevant data retrieved from another source (e.g., from a server). The retrieved relevant data may include, e.g., current/historical information stored on the server. Exemplary current/historical information may include a current/historical health condition of a subject, current/historical medications the subject is/was taking, current/historical medical treatment the subject is/was undertaking, current/historical diets, current/historical emotion status, current/historical physiological parameters (e.g., PTT, SBP, DBP) relating to the subject, or the like, or a combination thereof. The wearable or portable device, or the mobile device may display or report, or store at least some of the acquired signals, information, the retrieved relevant data, the calculated one or more physiological parameters of interest, or the like, or a combination thereof. The display or report may be provided to a subject, a user other than the subject, the server, or another device.

In another example, the system may include a wearable or portable device that may be configured to perform functions including: acquiring physiological signals or environmental information, retrieving relevant data from another source (e.g., from a server), calculating one or more physiological parameters of interest based on the acquired signals, information, or the retrieved relevant data, and displaying, reporting, or storing at least some of the acquired signals, information, the retrieved relevant data, the calculated one or more physiological parameters of interest, or the like, or a combination thereof. The display or report may be provided to a subject, a user other than the subject, the server, or another device.

In a further example, the system may include a wearable or portable device that may be configured to perform functions including: acquiring physiological signals and environmental information, communicating with a server to transmit at least some of the acquired signals or information to the server such that the server may calculate one or more physiological parameters of interest, receiving the calculated one or more physiological parameters of interest from the server, displaying, reporting or storing at least some of the acquired signals, information, the calculated one or more physiological parameters of interest, or the like, or a combination thereof. The display or report may be provided to a subject, a user other than the subject, the server, or another device. In some embodiments, the communication between the wearable or portable device and the server may be achieved by way of the wearable or portable device being connected to a network (e.g., the network 150). In some embodiments, the communication between the wearable or portable device and the server may be achieved via a communication device (e.g., a mobile device such as a smart phone, a tablet, a laptop computer, or the like) that communicates with both the wearable or portable device and the server.

In still a further example, the system may include a wearable or portable device, a mobile device (e.g., a smart phone, a tablet, a laptop computer, or the like), and a server. The wearable or portable device may be used to acquire physiological signals, environmental information, or the like, or a combination thereof. The mobile device may be used to receive the signals or information acquired by the wearable or portable device, and may calculate one or more physiological parameters of interest based on the received signals and/or information retrieved from the wearable or portable device as well as relevant data retrieved from another source (e.g., a server).

In some embodiments, the system may be configured to provide a user interface to allow a subject, a user other than the subject, or an entity to exchange information (including input into or output from the system) with the system as disclosed herein. The user interface may be implemented on a terminal device including, e.g., a mobile device, a computer, or the like, or a combination thereof. The access to the system may be allowed to one who has an appropriate access privilege. An access privilege may include, for example, a privilege to read some or all information relating to a subject, update some or all information relating to a subject, or the like, or a combination thereof. The access privilege may be associated with or linked to a set of login credentials. Merely by way of example, the system may provide three tiers of access privileges. A first tier may include a full access privilege regarding information relating to a subject, allowing both receiving and updating information relating to a subject. A second tier may include a partial access privilege regarding information relating to a subject, allowing receiving and updating part of information relating to a subject. A third tier may include a minimal access privilege regarding information relating to a subject, allowing receiving or updating part of information relating to a subject Different login credentials may be associated with different access privilege to the information relating to a subject in the system. As used herein, updating may include providing information that does not exist in the system, or modifying pre-existing information with new information.

Merely by way of example, the system may receive information relating to a subject provided via the user interface. The information relating to a subject may include basic information and optional information. Exemplary basic information may include the height, the weight, the age (or the date of birth), the gender, the arm length, the nationality, the occupation, a habit (e.g., a health-related habit such as an exercise habit), the education background, a hobby, the marital status, religious belief, a health-related history (e.g., whether a subject has a history of smoking, a food allergy, a drug allergy, a medical treatment history, a family health history, a history of genetic disease, information regarding a prior surgery, or the like, or a combination thereof), contact information, emergency contact, or the like, or a combination thereof. Exemplary optional information may include, current health condition of the subject, medications the subject is taking, a medical treatment the subject is undertaking, diet. The system may receive, via the user interface, information relating to a specific measurement of, e.g., a physiological parameter of interest. Examples of such information may include the motion state of the subject at or around the acquisition time (defined elsewhere in the present disclosure), the emotional state at or around the acquisition time, the stress level at or around the acquisition time, or the like, or a combination thereof. The system may receive, via the user interface, one or more options or instructions. In some embodiments, the options or instructions may be provided by a subject or a user other than the subject answering questions or making selections in response to questions or prompts by the system. In one example, the options or instructions may include a measurement frequency (e.g., once a week, once a month, twice a week, twice a month, once a day, twice a day, or the like), a preferred format of the presentation of information to the subject or a user other than the subject (e.g., email, a voice message, a text message, an audio alert, haptic feedback, or the like, or a combination thereof). In another example, the options or instructions may include information relating to calculating parameters of interest, e.g., rules regarding how to select a model, a function, calibration data, or the like, or a combination thereof.

In some embodiments, the system may provide, via the user interface, information to a subject, or a user other than the subject. Exemplary information may include an alert, a recommendation, a reminder, or the like, or a combination thereof. In one example, an alert may be provided or displayed to the subject or a user other than the subject if a triggering event occurs. Exemplary triggering events may be that at least some of the acquired information or a physiological parameter of interest exceeds a threshold. Merely by way of example, a triggering event may be that the acquired heart rate exceeds a threshold (e.g., higher than 150 beats per minute, lower than 40 beats per minute, or the like). As another example, a triggering event may be that the physiological parameter of interest, e.g., an estimated blood pressure, exceeds a threshold. In another example, a recommendation may be provided or displayed to the subject or a user other than the subject. Exemplary recommendations may be a request to input specific data (e.g., basic information, optional information, updated parameters of interest, updated models, updated functions, updated options and instructions, or the like, or a combination thereof). A reminder may be provided or displayed to the subject or a user other than the subject. Exemplary reminders may include a reminder to take a prescription medication, take a rest, take a measurement of a physiological parameter of interest, or the like, or a combination thereof.

In some embodiments, the system may communicate with the subject or a user other than the subject (also referred to as a third party) through the user interface. Exemplary third parties may be a doctor, a healthcare worker, a medical institution, a research facility, a peripheral device of the subject or a user well-connected to the subject, or the like. Exemplary communications may be related with health conditions of the subject, a dietary habit, an exercise habit, a prescription medication, instructions or steps to conduct a measurement, or the like, or a combination thereof. In some embodiments, a user interface accessible to or by a third party may be the same as, or different from a user interface accessible to or by a subject. In one example, an output or data may be transmitted to a third party (e.g., a computer, a terminal at a doctor's office, a hospital where a health care provider is located and the health condition of the subject is being monitored, or the like, or a combination thereof). The third party may input feedback information or instructions related to the output information via the user interface. Merely by way of example, a third party may receive information regarding one or more physiological parameters of interest relating to a subject, and accordingly provide a recommendation of actions to be taken by the subject (e.g., to take a prescription medication, to take a rest, to contact or visit the third party, or the like, or a combination thereof); the system may relay the recommendation to the subject.

Figure 2:
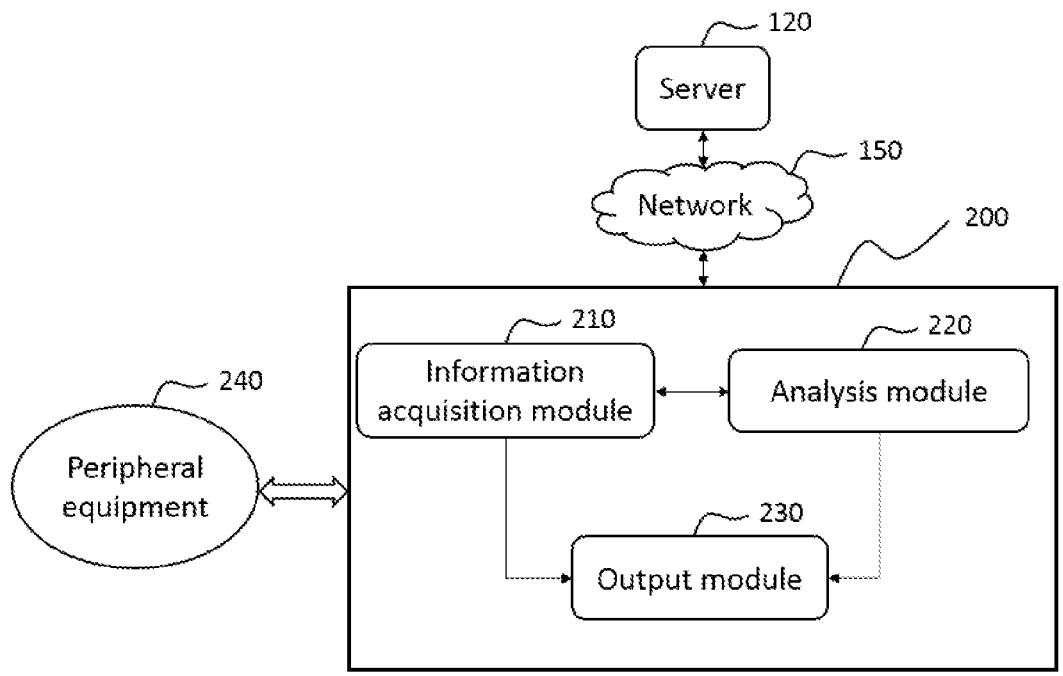
FIG. 2 depicts an exemplary diagram of an engine of the system illustrated in FIG. 1, according to some embodiments of the present disclosure.

FIG. 2 shows an exemplary diagram including the engine 200. The engine 200 may be configured for acquiring one or more signals and calculating or estimating one or more physiological parameters of interest based on the acquired signals. As illustrated, the engine 200 may be connected to or otherwise communicate with, e.g., peripheral equipment 240, and the server 120. The engine 200 may include an information acquisition module 210, an analysis module 220, and an output module 230. The information acquisition module 210 may be configured for acquiring a signal or information relating to a subject, e.g., a physiological signal, information relating to the health condition of the subject, or the like, or a combination thereof. The analysis module 220 may be configured for analyzing the acquired signal or information, or determining or estimating a physiological parameter of interest, or both. The output module 230 may be configured for outputting the acquired signal or information, the physiological parameter of interest, or the like, or a combination thereof. As used herein, a module may have an independent processor, or use system shared processor(s). The processor(s) may perform functions according to instructions related to various modules. For example, the analysis module 220, according to relevant instructions, may retrieve acquired signals and perform calculations to obtain one or more physiological parameter of interest.

The information acquisition module 210 may be configured for acquiring a signal or information from or relating to one or more subjects. As used herein, acquiring may be achieved by way of receiving a signal or information sensed, detected, or measured by, e.g., a sensor, or by way of receiving an input from a subject or from a user other than the subject (e.g., a doctor, a care provider, a family member relating to the subject, or the like, or a combination thereof). For brevity, an acquired signal or information may be referred to as acquired information. As used herein, information may include a signal relating to a subject that is acquired by a device including, e.g., a sensor, environmental information that is acquired by a device including, e.g., a sensor, information that is acquired otherwise including, e.g., from an input by a subject or a user other than the subject, a processed or pre-treated information that is acquired as described, or the like, or a combination thereof. Exemplary sensors may include an electrode sensor, an optical sensor, a photoelectric sensor, a pressure sensor, an accelerometer, a gravity sensor, a temperature sensor, a moisture sensor, or the like, or a combination thereof.

Exemplary acquired information may include physiological information. In the exemplary context of determining blood pressure, the physiological information may include a cardiovascular signal. Exemplary cardiovascular signals may include a photoplethysmogram (PPG) signal, an electrocardiogram (ECG) signal, a ballistocardiogram (BCG) signal, a blood pressure (BP), a systolic blood pressure (SBP), a diastolic blood pressure (DBP), a pulse rate (PR), a heart rate (HR), a heart rate variation (HRV), cardiac murmur, blood oxygen saturation, a density of blood, a pH value of the blood, a bowel sound, a brainwave, a fat content, a blood flow rate, or the like, or a combination thereof. Exemplary acquired information may include information regarding a subject, e.g., the height, the weight, the age, the gender, the body temperature, the arm length, an illness history, or the like, or a combination thereof. Exemplary acquired information may include information from or relating to the ambient surrounding a subject (referred to as environmental information) at or around the acquisition time. Exemplary environmental information may include temperature, humidity, air pressure, an air flow rate, an ambient light intensity, or the like, or a combination thereof. As used herein, the acquisition time may refer to a time point or a time period when information relating to the subject, e.g., physiological information of the subject, is acquired.

The information acquisition module 210 may include a signal acquisition unit (not shown in FIG. 2) configured for acquiring information relating to a subject, a signal acquisition unit (not shown in FIG. 2) configured for acquiring information provided by the subject or a user other than the subject, a signal acquisition unit (not shown in FIG. 2) configured for acquiring environmental information from the ambient surrounding the subject at or around the acquisition time, or the like, or a combination thereof.

A signal acquisition unit (not shown in FIG. 2) may be configured for receiving the subject's ECG signals acquired by way of an electrode sensing method. A signal acquisition unit (not shown in FIG. 2) may be configured for receive the subject's PPG signals acquired by way of a photoelectric sensing method. A signal acquisition unit (not shown in FIG. 2) may be configured for receiving the information regarding an illness history or illness data provided by the subject or a user other than the subject. A signal acquisition unit (not shown in FIG. 2) may be configured for acquiring the room temperature (where the subject is located at or around the acquisition time) by way of a temperature sensing method. A signal acquisition unit (not shown in FIG. 2) may communicate with one or more sensors to acquire information sensed, detected or measured by the one or more sensors. Exemplary sensors include an electrode sensor, an optical sensor, a photoelectric sensor, a conductance sensor, a pressure sensor, an accelerometer, a gravity sensor, a temperature sensor, a moisture sensor, or the like, or a combination thereof.

Merely by way of example, an optical sensor may include an integrated photodetector, amplifier, and a light source. The light source may emit radiation of wavelengths of, e.g., the visible spectrum, the infrared region, or the like, or a combination thereof. The photodetector may detect the reflected radiation. In another example, two wearable PPG sensors may be placed at two different locations on a subject. The two different places may be separated from each other by a known distance. In some embodiments, at least two of the sensors may be assembled into one device. The device may be a wearable or portable device including, e.g., a T-shirt, a smart watch, a wristband, or the like, or a combination thereof. The device may further include one or more processors or processing units. Signals or data may be transmitted between sensors placed at different locations. The transmission may be via a wireless connection, a wired connection, or the like, or a combination thereof. For example, signals received by the sensors may be transmitted through a wireless body sensor network (BSN) or an intrabody communication (IBC).

The information acquisition module 210 may be configured to receive or load information from the peripheral equipment 240, the server 120, or another device including, e.g., an ECG monitor, a PPG monitor, a respiratory monitor, a brainwave monitor, a blood glucose monitor, and a device having similar functions. Examples of such a device may include a smart watch, an earphone, a pair of glasses, a bracelet, a necklace, or the like. The peripheral equipment 240, the server 120, or such another device may be local or remote. For example, the server 120 and the engine 200 may be connected through a local area network, or Internet. The peripheral equipment 240 and the engine 200 may be connected through a local area network, or Internet. Another device and the engine 200 may be connected through a local area network, or Internet. The information transmission between the information acquisition module 210 and the peripheral equipment 240, the server 120, or such another device may be via a wired connection, a wireless connection, or the like, or a combination thereof.

The information acquisition module 210 may be configured to receive information provided by a subject or a user other than the subject via, e.g., an input device. An input device may include alphanumeric and other keys that may be inputted via a keyboard, touch screen (e.g., with haptics or tactile feedback), speech input, eye tracking input, a brain monitoring system, or other comparable input mechanism. The input information received through the input device may be transmitted to a processor of the SoC, e.g., via a bus, for further processing. Other types of the input device may include a cursor control device, such as a mouse, a trackball, or cursor direction keys to communicate direction information and command selections, e.g., to the SoC and to control cursor movement on a display device.

The description of the information acquisition module 210 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, a storage unit (not shown in FIG. 2) may be added to the information acquisition module 210 for storing the acquired information.

The analysis module 220 may be configured for analyzing acquired information. The analysis module 220 may be connected to or otherwise communicate with one or more information acquisition modules 210-1, 210-2, . . . , 210-N to receive at least part of the acquired information. The analysis module 220 may be configured for performing one or more operations including, e.g., a pre-treatment, a calculation, a calibration, a statistical analysis, or the like, or a combination thereof. Any one of the operations may be performed based on at least some of the acquired information, or an intermediate result from another operation (e.g., an operation performed by the analysis module 220, or another component of the system 100). For instance, the analysis may include one or more operations including pre-treating at least part of the acquired information, identifying a characteristic point or feature of the acquired information or the pre-treated information, calculating an intermediate result based on the identified characteristic point or feature, performing a calibration, analyzing the information regarding the subject provided by the subject or a user other than the subject, analyzing the information regarding the ambient surrounding the subject at or around the acquisition time, estimating a physiological parameter of interest, or the like, or a combination thereof.

Some operations of the analysis may be performed in parallel or in series. As used herein, a parallel performance may indicate that some operations of the analysis may be performed at or around the same time; a serial performance may indicate that some operations of the analysis may commence or be performed after other operations of the analysis have commenced or completed. In some embodiments, at least two operations of an analysis may be performed in parallel. In some embodiments, at least two operations of an analysis may be performed in series. In some embodiments, some of the operations of an analysis may be performed in parallel, and some of the operations may be performed in series.

The analysis, or some operations of the analysis, may be performed real time, i.e. at or around the acquisition time. The analysis, or some operations of the analysis, may be performed after a delay since the information is acquired. In some embodiments, the acquired information is stored for analysis after a delay. In some embodiments, the acquired information is pre-treated and stored for further analysis after a delay. The delay may be in the order of seconds, or minutes, or hours, or days, or longer. After the delay, the analysis may be triggered by an instruction from a subject or a user other than the subject (e.g., a doctor, a care provider, a family member relating to the subject, or the like, or a combination thereof), an instruction stored in the system 100, or the like, or a combination thereof. Merely by way of example, the instruction stored in the system 100 may specify the duration of the delay, the time the analysis is to be performed, the frequency the analysis is to be performed, a triggering event that triggers the performance of the analysis, or the like, or a combination thereof. The instruction stored in the system 100 may be provided by a subject or a user other than the subject. An exemplary triggering event may be that at least some of the acquired information or a physiological parameter of interest exceeds a threshold. Merely by way of example, a triggering event may be that the acquired heart rate exceeds a threshold (e.g., higher than 150 beats per minute, lower than 40 beats per minute, or the like). As used herein, "exceed" may be larger than or lower than a threshold. As another example, a triggering event may be that the physiological parameter of interest, e.g., an estimated blood pressure, exceeds a threshold.

The analysis module 220 may be centralized or distributed. A centralized analysis module 220 may include a processor (not shown in FIG. 2). The processor may be configured for performing the operations. A distributed analysis module 220 may include a plurality of operation units (not shown in FIG. 2). The operation units may be configured for collectively performing the operations of a same analysis. In the distributed configuration, the performance of the plurality of operation units may be controlled or coordinated by, e.g., the server 120.

The acquired information, an intermediate result of the analysis, or a result of the analysis (e.g., a physiological parameter of interest) may be analog or digital. In an exemplary context of blood pressure monitoring, the acquired information, an intermediate result of the analysis, or a result of the analysis (e.g., a physiological parameter of interest) may include, for example, a PPG signal, an ECG signal, a BCG signal, a BP, a SBP, a DBP, a PR, a HR, a HRV (heart rate variation), cardiac murmur, blood oxygen saturation, a blood density, a pH value of the blood, a bowel sound, a brainwave, a fat content, a blood flow rate, or the like, or a combination thereof.

A result of the analysis, e.g., a physiological parameter of interest regarding a subject, may be influenced by various factors or conditions including, e.g., an environmental factor, a factor due to a physiological condition of a subject, a factor due to a psychological condition of a subject, or the like, or a combination thereof. One or more of such factors may influence the accuracy of the acquired information, the accuracy of an intermediate result of the analysis, the accuracy of a result of the analysis, or the like, or a combination thereof. For instance, a physiological parameter of interest may be estimated based on a correlation with the acquired information; a factor due to a physiological condition may cause a deviation from the correlation; the factor may influence the accuracy of the physiological parameter of interest that is estimated based on the correlation. Merely by way of example, a cardiovascular signal relating to a subject may vary with, for example, time, the psychological condition of the subject, the psychological condition of the subject, or the like, or a combination thereof. The correlation between a cardiovascular signal with a physiological parameter of a subject may vary with, for example, the psychological condition of the subject, the psychological condition of the subject, the ambient surrounding the subject, or the like, or a combination thereof. Such an influence may be counterbalanced in the analysis.

In an analysis, information relating to an influencing condition (e.g., environmental information, a physiological condition, a psychological condition, or the like) may be acquired, and a correction or adjustment may be made accordingly in the analysis. Merely by way of example, the correction or adjustment may be by way of a correction factor. For instance, an environmental correction factor may be introduced into the analysis based on acquired environmental information from or relating to the ambient surrounding a subject at or around the acquisition time. Exemplary environmental information may include one or more of temperature, humidity, air pressure, an air flow rate, an ambient light intensity, or the like. Exemplary environmental correction factors may include one or more of a temperature correction factor, a humidity correction factor, an air pressure correction factor, an air flow rate correction factor, an ambient light intensity correction factor, or the like. As another example, the correction or adjustment may be by way of performing a calibration of the correlation (e.g., a calibrated model, a calibrated function, or the like) used to estimate the physiological parameter of interest. As a further example, the correction or adjustment may be by way of choosing, based on information relating to an influencing condition, a correlation from a plurality of correlations used to estimate the physiological parameter of interest.

This description of the analysis module 220 is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, a cache unit (not shown in FIG. 2) may be added to the analysis module 220 used for storing an intermediate result or real time signal or information during the processes above mentioned.

The output module 230 may be configured for providing an output. The output may include a physiological parameter of interest, at least some of the acquired information (e.g., the acquired information that is used in estimating the physiological parameter of interest), or the like, or a combination thereof. The transmission of the output may be via a wired connection, a wireless connection, or the like, or a combination thereof. The output may be transmitted real-time once the output is available for transmission. The output may be transmitted after a delay since the output is available for transmission. The delay may be in the order of seconds, or minutes, or hours, or days, or longer. After the delay, the output may be triggered by an instruction from a subject or a user other than the subject (e.g., a doctor, a care provider, a family member relating to the subject, or the like, or a combination thereof), an instruction stored in the system 100, or the like, or a combination thereof. Merely by way of example, the instruction stored in the system 100 may specify the duration of the delay, the time the output is to be transmitted, the frequency output is to be transmitted, a triggering event, or the like, or a combination thereof. The instruction stored in the system 100 may be provided by a subject or a user other than the subject. An exemplary triggering event may be that the physiological parameter of interest or that at least some of the acquired information exceeds a threshold. Merely by way of example, a triggering event may be that the acquired heart rate exceeds a threshold (e.g., higher than 150 beats per minute, lower than 40 beats per minute, or the like). As another example, a triggering event may be that the physiological parameter of interest, e.g., an estimated blood pressure, exceeds a threshold.

The output for transmission may be of, for example, an analog form, a digital form, or the like, or a combination thereof. The output may be in the format of, for example, a graph, a code, a voice message, text, video, an audio alert, a haptic effect, or the like, or a combination thereof. The output may be displayed on a local terminal, or transmitted to a remote terminal, or both. A terminal may include, for example, a personal computer (PC), a desktop computer, a laptop computer, a smart phone, a smart watch, or the like, or a combination thereof. Merely by way of example, an output may be displayed on a wearable or portable device a subject wears, and also transmitted to a computer or terminal at a doctor's office or a hospital where a health care provider is located and monitors the health condition of the subject.

The output module 230 may include or communicate with a display device configured to display output or other information to a subject or a user other than the subject. The display device may include a liquid crystal display (LCD), a light emitting diode (LED)-based display, or any other flat panel display, or may use a cathode ray tube (CRT), a touch screen, or the like. A touch screen may include, e.g., a resistance touch screen, a capacity touch screen, a plasma touch screen, a vector pressure sensing touch screen, an infrared touch screen, or the like, or a combination thereof.

The peripheral equipment 240 may include any kind of local or remote apparatuses or devices relating to or communicating with the system 100, or a portion thereof. For example, the peripheral equipment 240 may include a storage device, display equipment, a measuring device, an input device, or the like, or a combination thereof.

In some embodiments, a storage module (not shown in FIG. 2) or a storage unit (not shown in FIG. 2) may be integrated in the engine 200. In some embodiments, a storage unit (not shown in FIG. 2) may be integrated in any one of the information acquisition module 210, the analysis module 220, or the output module 230. The storage module (not shown in FIG. 2) or the storage unit (not shown in FIG. 2) may be used for storing an intermediate result, or a result of an analysis. The storage module (not shown in FIG. 2) or the storage unit (not shown in FIG. 2) may be used as a data cache. The storage module (not shown in FIG. 2) or the storage unit (not shown in FIG. 2) may include a hard disk, a floppy disk, selectron storage, RAM, DRAM, SRAM bubble memory, thin film memory, magnetic plated wire memory, phase change memory, flash memory, cloud disk, or the like, or a combination thereof. The storage module (not shown in FIG. 2) or the storage unit (not shown in FIG. 2) may include memory or electronic storage media described in connection with FIG. 1 and elsewhere in the present disclosure.

In some embodiments, the engine 200 does not include a storage module or a storage unit, and the peripheral equipment 240 or the server 120 may be used as a storage device accessible by the engine 200. The server 120 may be a cloud server providing cloud storage. As used herein, cloud storage is a model of data storage where digital data are stored in logical pools, physical storage spanning multiple servers (and often located at multiple locations). The physical environment including, e.g., the logical pools, the physical storage spanning multiple servers may be owned and managed by a hosting company. The hosting company may be responsible for keeping the data available and accessible, and the physical environment protected and running. Such cloud storage may be accessed through a cloud service, a web service application programming interface (API), or by applications that utilize the API. Exemplary applications include cloud desktop storage, a cloud storage gateway, a Web-based content management system, or the like, or a combination thereof. The server 120 may include a public cloud, a personal cloud, or both. For example, the acquired information may be stored in a personal cloud that may be accessed after authorization by way of authenticating, e.g., a username, a password, a secret code, or the like, or a combination thereof. Non personalized information including, for example, methods or calculation models, may be stored in a public cloud. No authorization or authentication is needed to access the public cloud. The information acquisition module 210, the analysis module 220 and the output module 230 may retrieve or load information or data from the public cloud or the personal clouds. Any one of these modules may be configured to transmit signals and data to the public cloud or personal cloud.

Connection or transmission between any two of the information acquisition module 210, the analysis module 220, and the output module 230 may be via a wired connection, a wireless connection, or the like, or a combination thereof. At least two of these modules may be connected with different peripheral equipment. At least two of these modules may be connected with the same peripheral equipment. The peripheral equipment 240 may be connected with one or more modules via a wired connection, a wireless connection, or the like, or a combination thereof. Those skilled in the art should understand that the above embodiments are only utilized to describe the invention in the present disclosure. There are many modifications and variations to the present disclosure without departing the spirit of the invention disclosed in the present disclosure. For example, the information acquisition module 210 and the output module 230 may be integrated in an independent module configured for acquiring and outputting signals or results. The independent module may be connected with the analysis module 220 via a wired connection, a wireless connection, or the like, or a combination thereof. The three modules in the engine 200 may be partially integrated in one or more independent modules or share one or more units.

The connection or transmission between the modules in the system 100, or between the modules and the peripheral equipment 240, or between the system and the server 120 should not be limited to the descriptions above. All the connections or transmissions may be used in combination or may be used independently. The modules may be integrated in an independent module, i.e. functions of the modules may be implemented by the independent module. Similarly, one or more modules may be integrated on a single piece of peripheral equipment 240. Any one of the connections or transmissions mentioned above may be via a wired connection, a wireless connection, or the like, or a combination thereof. For example, the wired connection or wireless connection may include, e.g., a wire, a cable, satellite, microwave, bluetooth, radio, infrared, or the like, or a combination thereof.

The engine 200 may be implemented on one or more processors. The modules or units of the engine 200 may be integrated in one or more processors. For example, the information acquisition module 210, the analysis module 220, and the output module 230 may be implemented on one or more processors. The one or more processors may transmit signals or data with a storage device (not shown in FIG. 2), the peripheral equipment 240, and the server 120. The one or more processors may retrieve or load signals, information, or instructions from the storage device (not shown in FIG. 2), the peripheral equipment 240, or the server 120, and process the signals, information, data, or instructions, or a combination thereof, to calculate one or more physiological parameters of interest. The one or more processors may also be connected or communicate with other devices relating to the system 100, and transmit or share signals, information, instructions, the physiological parameters of interest, or the like with such other devices via, e.g., a mobile phone APP, a local or remote terminal, or the like, or a combination thereof.

Figure 3:
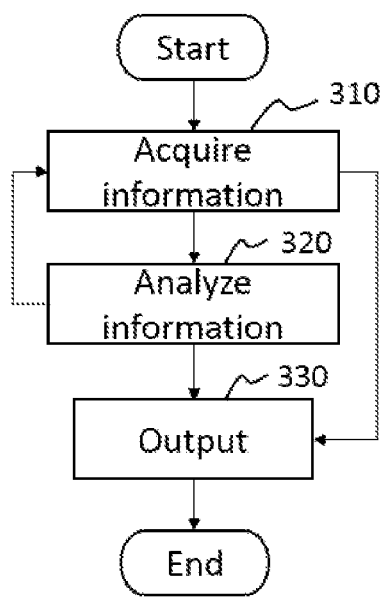
FIG. 3 is a flowchart of an exemplary process in which a method for estimating a physiological signal is deployed, according to some embodiments of the present disclosure.

FIG. 3 is a flowchart showing an exemplary process for estimating a physiological parameter of interest according to some embodiments of the present disclosure. Information regarding a subject may be acquired in step 310. The information acquisition may be performed by the information acquisition module 210. The acquired information may include physiological information of the subject, environmental information relating to the ambient surrounding the subject at or around the acquisition time, information provided by the subject or a user other than the subject. The acquired information may include a PPG signal, an ECG signal, a pulse rate, a heart rate, a heart rate variation, blood oxygen saturation, respiration, muscle state, skeleton state, a brainwave, a blood lipid level, a blood sugar level, the height, the weight, the age, gender, the body temperature, the arm length, an illness history, the room temperature, humidity, air pressure, an air flow rate, the ambient light intensity, or the like, or a combination thereof. At least some of the acquired information may be analyzed at 320. Via the analysis, various features of at least some of the acquired information may be identified. For example, the acquired information may include a PPG signal and an ECG signal; the identified features of these signals may include, for example, waveform, characteristic points, peak points, valley points, amplitude, time intervals, phase, frequencies, cycles, or the like, or a combination thereof. Analysis based on the identified features may be carried out in step 320. For example, the physiological parameter of interest may be calculated or estimated based on the identified features. The physiological parameter of interest estimated based on the acquired PPG signal and ECG signal may include, e.g., the BP, the SBP, the DBP, or the like, or a combination thereof. The physiological parameter of interest may be outputted in step 330. Some of the acquired information may be outputted in step 330. The output may be displayed to the subject or a user other than the subject, printed, stored in a storage device or the server 120, transmitted to a device further process, or the like, or a combination thereof. It should be noted that after analysis in step 320, a new acquisition step may be performed in step 310.

This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. For example, a pre-treatment step may be added between step 310 and step 320. In the pre-treatment step, the acquired signals may be pre-treated, in order to reduce or remove noise or interferences in the signals originally acquired. For example, a sophisticated, real-time digital filtering may be used to reduce or remove high-frequency noise from the PPG or ECG signal, allowing their features to be accurately identified. Exemplary pre-treatment methods may include low-pass filtering, band-pass filtering, wavelet transform, median filtering, morphological filtering, curve fitting, Hilbert-Huang transform, or the like, or a combination thereof. Descriptions regarding methods and systems for reducing or removing noise from a physiological signal, e.g., a PPG signal or an ECG signal, may be found in, e.g., International Patent Application Nos. PCT/CN2015/077026 filed Apr. 20, 2015, PCT/CN2015/077025 filed Apr. 20, 2015, and PCT/CN2015/079956 filed May 27, 2015, each of which is incorporated by reference. One or more other optional steps may be added between step 310 and step 320, or elsewhere in the exemplary process illustrated in FIG. 3. Examples of such steps may include storing or caching the acquired information.

Figure 4:
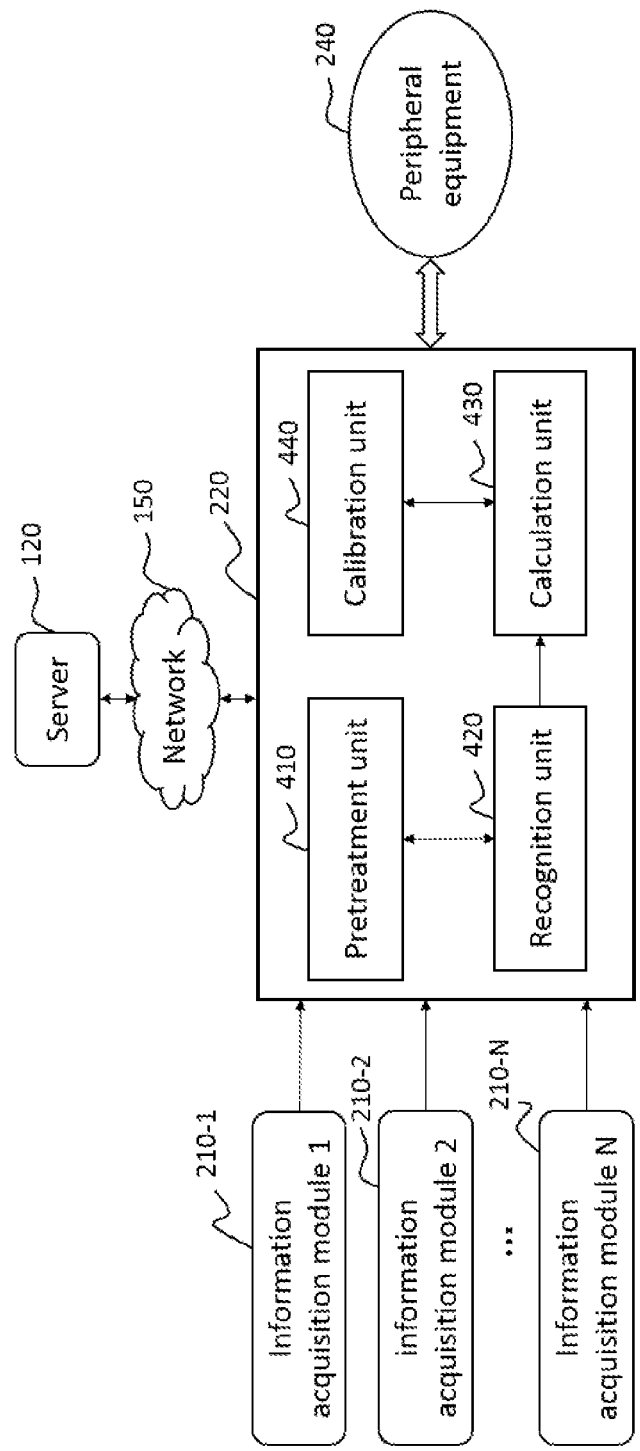
FIG. 4 is a block diagram illustrating an architecture of an analysis module according to some embodiments of the present disclosure.

FIG. 4 is a block diagram illustrating an architecture of an analysis module 220 according to some embodiments of the present disclosure. The analysis module 220 may be connected to or otherwise communicate with, e.g., the peripheral equipment 240, and the server 120 through the network 150. The analysis module 220 may be configured to estimate or calculate a physiological parameter of interest relating to a subject based on acquired information. The analysis module 220 may include a pre-treatment unit 410, a recognition unit 420, a calculation unit 430, and a calibration unit 440.

The pre-treatment unit 410 may be configured for pre-treating the acquired information. The pre-treatment may be performed to reduce and remove noise or interferences in the original signals. For example, a sophisticated, real-time digital filtering may reduce or remove high-frequency noise from the PPG or ECG waveforms. Exemplary methods for pre-treatment may include low-pass filtering, band-pass filtering, wavelet transform, median filtering, morphological filtering, curve fitting, Hilbert-Huang transform, or the like, or any combination thereof. Descriptions regarding methods and systems for reducing or removing noise from a physiological signal, e.g., a PPG signal or an ECG signal, may be found in, e.g., International Patent Application Nos. PCT/CN2015/077026 filed Apr. 20, 2015, PCT/CN2015/077025 filed Apr. 20, 2015, and PCT/CN2015/079956 filed May 27, 2015, each of which is incorporated by reference.

The pre-treatment unit 410 may include one or more pre-treatment sub-units (not shown in FIG. 4). The pre-treatment sub-units may (not shown in FIG. 4) may perform one or more pre-treatment steps for pre-treating the acquired signals in series (e.g., a pre-treatment step performed after another pre-treatment step has commenced or completed) or in parallel (e.g., some pre-treatment steps performed at or around the same time). The pre-treatment unit 410 may be configured to control or coordinate the operations of the pre-treatment sub-units (not shown in FIG. 4). The control or coordination may be performed by, e.g., a controller (not shown in FIG. 4). The pre-treatment sub-units may be arranged in series or in parallel.

This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. For example, the pre-treatment sub-units may be combined variously in order to achieve better pre-treatment effect. It should be noted that the pre-treatment sub-units are not necessary for the function of the system. Similar modifications should fall within the metes and bounds of the claims.

The recognition unit 420 is configured for analyzing the acquired information to recognize or identify a feature. In some embodiments, the acquired information may have been pre-treated before it is processed in the recognition unit 420. In the exemplary context of blood pressure monitoring, the acquired information may include a PPG signal, an ECG signal, a BCG signal, or the like, or a combination thereof; exemplary features of the acquired information may include waveform, characteristic points, peak points, valley points, amplitude, time intervals, phase, frequencies, cycles, or the like, or any combination thereof.

The recognition unit 420 may be configured for analyzing different types of information or different portions of information. The analysis may be performed by, e.g., one or more recognition sub-units (not shown in FIG. 4). For example, the acquired information includes various types of physiological signals (e.g., a PPG signal and an ECG signal) and may be analyzed by different recognition sub-units. Exemplary methods that may be employed in the recognition unit 420 may include a threshold method, a syntactic approach of pattern recognition, Gaussian function depression, wavelet transform, a QRS complex detection, a linear discriminant analysis, a quadratic discriminatory analysis, a decision tree, a decision table, a near neighbor classification, a wavelet neural networks algorithm, a support vector machine, gene expression programming, hierarchical clustering, a mean cluster analysis, a Bayesian network algorithm, a principal component analysis, a Kalman filter, Gaussian regression, linear regression, Hidden Markov Model, association rules, an inductive logic method, or the like, or any combination thereof. Various methods may be used in parallel or may be used in combination. Merely by way of example, the recognition unit may use two different methods when processing two types of signals. As another example, the recognition unit may use two different methods, e.g., one method after another, when processing one type of signal.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. Merely by way of example, the analyzed features may be uploaded to the public clouds or the personal clouds and may be used in subsequent calculation or calibration. As another example, the recognition sub-units (not shown in FIG. 4) are not necessary for the function of the system. Similar modifications should fall within the metes and bounds of the present disclosure.

The calculation unit 430 may be configured for performing various calculations to determine, e.g., coefficients of a model or function relating to a physiological parameter of interest, the physiological parameter of interest, or the like, or a combination thereof. For instance, the calculation unit 430 may be configured for calculating, e.g., different coefficients of a model or function relating to a physiological parameter of interest, different coefficients of different models or functions illustrating the correlation of a physiological parameter of interest and one or more measurable signals or other information. The calculation unit 430 may include one or more calculation sub-units (not shown in FIG. 4) to perform the calculations. A physiological parameter of interest may including, e.g., PTT, PTTV (pulse transit time variation), a BP, a SBP, a DBP, a pulse rate, a heart rate, a HRV, cardiac murmur, blood oxygen saturation, a blood density, or the like, or any combination thereof.

In the exemplary context of estimating BP of a subject (including SBP and DBP), based on PTT, the correlation between BP and PTT may be represented by a model 900-5 (see FIG. 9-E) including mathematical processing 900-4 (see FIG. 9-E), and a factored function 900-3 (see FIG. 9-E), while the factored function 900-3 may include a function (f) and coefficient (B) 900-2 (see FIG. 9-E). As used herein, calibration may include at least two aspects. A first aspect is that a model 900-5 is determined based on one or more sets of calibration data (or calibration values). Equations 9 and 10 (see Example 1) illustrate exemplary models 900-5 for SBP and DBP, respectively. The calibration may provide coefficients $a_1, a_2, a_3, \ldots a_m$, and $b_1, b_2, b_3, \ldots b_n$ for in and n. To use the calibrated model 900-5 illustrated in Equations 9 and 10 in a specific measurement, signals need to be acquired to provide PTT, and a set of calibration data including PTT0, SBP0, and DBP0. The value of in and the value of n may be specified for a calibration. If multiple calibrations are performed, the model may be optimized, including determining coefficients $a_1, a_2, a_3, \ldots a_m$, and $b_1, b_2, b_3, \ldots b_n$ and also optimizing the values of in and n. The correlation between BP and PTT may depend on other elements, in addition to PTT. Merely by way of example, t correlation between BP and PTT may depend on HRV, PTTV, in addition to PTT. Equations 11 and 12 (see Example 1) illustrate exemplary models 900-5 for SBP and DBP, respectively, in which HRV, PTTV, and PTT are considered in determining BP. To use the calibrated model 900-5 illustrated in Equations 11 and 12 in a specific measurement, signals need to be acquired to provide PTT, HRV, and PTTV, and a set of calibration data including PTT0, SBP0, DBP0, HRV0, and PTTV0.

The first aspect of calibration may be performed using personalized calibration data relating to the subject, or peer data, or empirical data. This aspect of calibration may be performed real time when a specific measurement is performed. A model 900-5 to be used to estimate BP based on the PTT in the specific measure may be derived based on one or more sets of calibration data. The selection of the one or more sets of calibration data may be based on the PTT in the specific measurement. See, for example, the localized analysis in FIG. 9-B and the description thereof in the present disclosure. This aspect of calibration may be perform offline, independent of a specific measurement. See, e.g., FIGS. 9-A through 9-D and the description thereof in the present disclosure.

A second aspect of the calibration includes acquiring a set of calibration data to be applied in a calibrated model 900-5 so that a blood pressure may be estimated based on PTT acquired in a specific measurement, according to the model 900-5 and the set of calibration data. In some embodiments, the set of calibration data to be used in the specific measurement may be selected from, e.g., a plurality of sets of calibration data. The plurality of sets of calibration data may include personalized data relating to the subject, peer data, or empirical data. The plurality of sets of calibration data may be saved in the system, e.g., in the library 1100 (see FIG. 11). The plurality of sets of calibration data may be saved in a server that is part of or accessible from the system. In some embodiments, the set of calibration data may be selected based on the PTT in the specific measurement. See, for example, the localized analysis in FIG. 9-A and the description thereof in the present disclosure.

Exemplary methods that may be employed in the calculation unit 430 may include a direct mathematical calculation, an indirect mathematical calculation, a compensated calculation, a vector operation, a function operation, a wave speed evaluation, an equation parameter evaluation, a tension evaluation, or the like, or any combination thereof. One or more calculation models may be integrated in the calculation sub-units, or the calculation models may be placed in the server 120, or the calculation models may be placed in public clouds. Different models may be loaded when different coefficients or physiological parameters are to be calculated. For example, a linear calculation model in a calculation sub-unit may be used for calculating the SBP, while another non-linear calculation model in another calculation sub-unit may be used for calculating the DBP. An initial data or intermediate result used for calculating a physiological parameter of interest may be retrieved or loaded from the information acquisition module 210, the analysis module 220, the server 120, the peripheral equipment 240, or the like, or any combination thereof. The initial data and the intermediate result may be combined in various ways in the calculation unit 430.

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. In one embodiment, calculated coefficients or calculated physiological parameters may be used as an intermediate result for further analysis. In another example, an individual physiological parameter of interest or one group of related physiological parameters of interest may be calculated by the calculation unit.

The calibration unit 440 may be configured for performing a calibration. The calibration (also referred to as calibration process or calibration procedure) may include one or more steps of retrieving calibration data (or calibration values) for a subject; acquiring a set of information of the subject using a device to be calibrated or used in a future process (e.g., a wearable or portable device); determining a calibrated model or aportion thereof for the calibrated device with respect to the subject, or the like, or a combination thereof. The acquired set of information may include information provided by the subject or a user other than the subject, or information acquired by using the device to be calibrated, or the like, or a combination thereof. A set of calibration data may include a specific physiological parameter of interest obtained in one calibration process, an acquired set of information relating to the specific physiological parameter of interest in the same calibration process.

Merely by way of example, the device to be calibrated is configured to estimate blood pressure (including the SBP and the DBP) based on PTT derived from an ECG waveform acquired using the device and a corresponding PPG waveform acquired using the same device. A set of calibration data may include a SBP and a DBP, both measured by a healthcare provider in a hospital setting, and a corresponding ECG waveform and a corresponding PPG waveform acquired using the device to be calibrated. The corresponding ECG waveform and the corresponding PPG waveform acquired using the device to be calibrated may correspond to the SBP and the DBP measured by a healthcare provider. The corresponding ECG waveform and the corresponding PPG waveform may be acquired using the device to be calibrated at or around the time the SBP and the DBP are measured by a healthcare provider.

One or more sets of calibration data may be used to determine coefficients of a calibrated model, or some other portion of the calibrated model. The calibrated model may be used in a future process for calculating the physiological parameter of interest based on another set of information that is acquired using the calibrated device. In a future process, the calibrated device may acquire a set of information that is the same or similar to the set of information acquired for the calibration. For instance, the other set of information may include information acquired using the same device as that used in the calibration (e.g., the device including one or more sensors), information of the same type as that acquired in the calibration (e.g., the age of the subject, the acquisition time during the day, the physiological or psychological condition of the subject, or the like, or a combination thereof), or the like, or a combination thereof. The calibrated model may be used to calculate or estimate the physiological parameter of interest accordingly. Exemplary methods that may be used in the calibration to obtain the calibrated model may include a regression analysis, a linear analysis, a functional operation, reconstitution, Fourier transform, Laplace transform, or the like, or a combination thereof.

In a calibration process, a set of calibration data may include a specific physiological parameter of interest obtained based on a measurement using one or more devices other than the device to be calibrated. Merely by way of example, the specific physiological parameter of interest may be obtained based on a measurement performed on the subject by a healthcare professional in a hospital or a doctor's office. As another example, the specific physiological parameter of interest may be obtained based on a measurement performed on the subject by the subject or someone else using a clinical device or a household device. For instance, the physiological parameter of interest may be measured using a device including, e.g., an auscultatory device, an oscillometric device, an ECG management device, a PPG management device, or the like, or any combination thereof.

In a calibration process, a set of calibration data may include a specific physiological parameter of interest previously calculated or estimated by the system or a portion of the system. Merely by way of example, the physiological parameter of interest calculated by the system based on a set of acquired information and a calibrated function in the system may be used in a next calibration to update or generate a calibrated model, and the updated calibrated model may be used in the future to calculate the physiological parameter of interest (the first aspect of the calibration process described above). As another example, the physiological parameter of interest calculated by the system based on a set of acquired information and a calibrated function in the system may be used in a next measurement for the physiological parameter of interest (the second aspect of the calibration process described above). The calculated physiological parameter of interest of the subject may be stored in, e.g., the library 1100 or in the server 120, for future use in connection with the subject or other subjects.

A calibrated model to be used for a specific subject may be based on the calibration data of the same subject. A calibrated model to be used for a specific subject may be based on a combination of the calibration data of the same subject and calibration data from a group of subjects (e.g., peer data discussed elsewhere in the present disclosure). A calibrated function to be used for a specific subject may be based on the calibration data from a group of subjects (e.g., peer data or empirical data discussed elsewhere in the present disclosure). The specific subject may be included in the group, or not included. The calibration data may be stored in, e.g., the library 1100, the server 120, or the like, or a combination thereof. Personalized calibration data of different subjects may be stored in corresponding personal accounts of respective subjects in the server 120 or a personal cloud. Calibration data from various subjects may be stored in a non-personalized database for future use. For instance, calibration data from various subjects may be divided based on one or more characteristics of the respective subjects. Exemplary characters may include, e.g., age, gender, stature, weight, a body fat percentage, color of skin, a family health history, a life style, an exercise habit or other habit, diet, a psychological condition, a health condition, an education history, occupation, or the like, or a combination thereof. In some embodiments, a portion of the calibration data (e.g., peer data discussed elsewhere in the present disclosure) so divided may be used for calibration purposes by a group of subjects that share the same or similar characteristic(s).

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. For example, a storage unit (not shown in FIG. 4) may be added to the calibration unit 440 or the calculation unit 430, or a combination thereof. The storage unit in the calibration unit 440 may be configured to store the calibration data or historical data relating to calibration process. The storage unit relating to calculation unit 430 may be configured to store calculation algorithms or data relating to calculation process. Additionally, peer data may be used as initial data or an intermediate result during calibrating.

The analysis module 220 may be implemented on one or more processors. The units of the analysis module 220 may be integrated in one or more processors. For example, the pre-treatment unit 410, the recognition unit 420, the calculation unit 430, and the calibration unit 440 may be implemented on one or more processors. The one or more processors may transmit signals or data with a storage device (not shown in FIG. 4), the information acquisition modules 1, 2, and 3, the peripheral equipment 240, and the server 120. The one or more processors may retrieve or load signals, information, or instructions from the storage device (not shown in FIG. 4), the information acquisition modules 1, 2, and 3, the peripheral equipment 240, or the server 120, and process the signals, information, data, or instructions, or a combination thereof, to perform pre-treatment, calculation of one or more physiological parameters of interest, calibration, or the like, or a combination thereof. The one or more processors may also be connected or communicate with other devices relating to the system 100, and transmit or share signals, information, instructions, the physiological parameters of interest, or the like with such other devices via, e.g., a mobile phone APP, a local or remote terminal, or the like, or a combination thereof.

Figure 5:
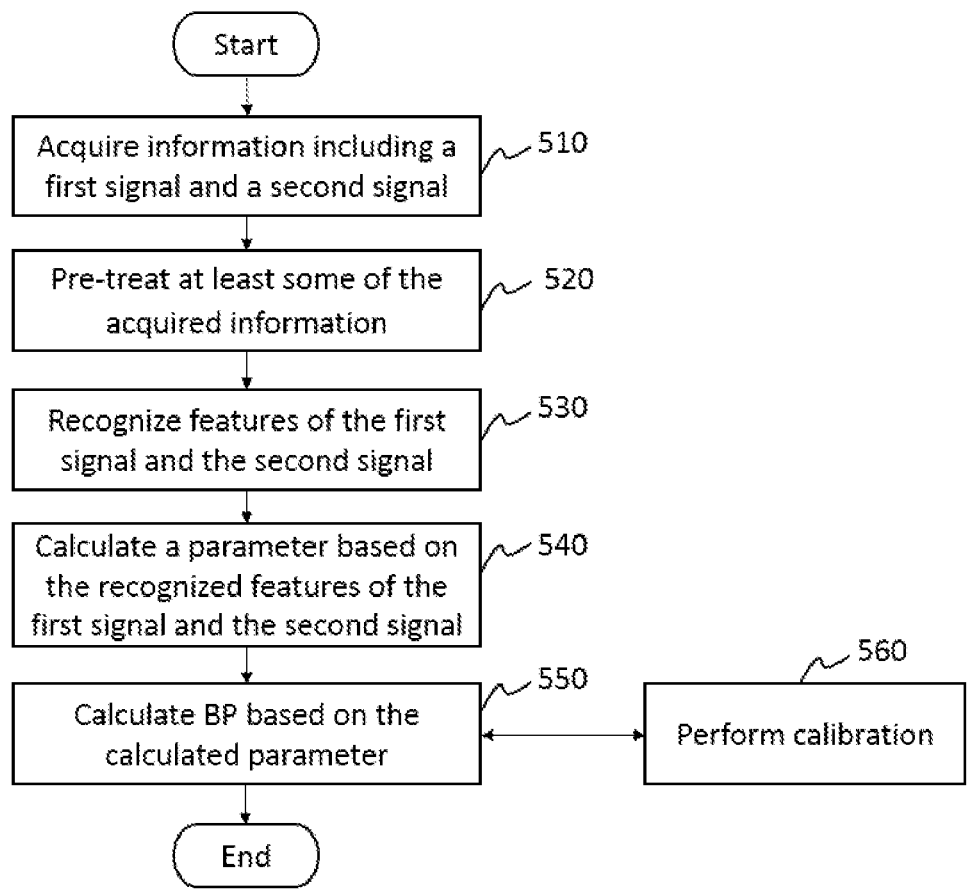
FIG. 5 is a flowchart diagram of an exemplary process for estimating blood pressure according to some embodiments of the present disclosure.

FIG. 5 is a flowchart diagram of an exemplary process for estimating blood pressure according to some embodiments of the present disclosure. Beginning in step 510, information including a first signal and a second signal may be acquired. The acquisition of the signals may be performed by information acquisition module 210. In some embodiments, the first and second signals may be acquired simultaneously, at or around the same time. In some embodiments, one signal may be acquired prior to the other signal. Merely by way of example, the first signal or the second signal may be physiological signals, e.g., an electrocardiogram (ECG) signal, a pulse-wave-related signal (such as photoplethysmogram (PPG)), a phonocardiogram (PCG) signal, an impedance cardiogram (ICG) signal, or the like, or any combination thereof. In some embodiments, the first signal and the second signal may be of different types. For example, the first and second signals may be the combination of an ECG signal and a PPG signal, the combination of an ECG signal and a PCG signal, the combination of an ECG signal and an ICG signal, or the like. In some embodiments, the first signal and the second signal may be of the same type. For example, the first and second signals may be two PPG signals that may be detected at different locations on the body of the subject. The exemplary locations on the body of the subject may include e.g., the finger, the radial artery, the ear, the wrist, the toe, or the locations that are more suitable for ambulatory monitoring in current sensor designs.

In step 520, at least some of the acquired information may be pre-treated. In some embodiments, the acquired first and second signals may be pre-treated. The pre-treatment may be performed to reduce or remove noise or interferences in the signals or signal related data. Exemplary methods that may be used in the pre-treatment may include low-pass filtering, band-pass filtering, wavelet transform, median filtering, morphological filtering, curve fitting, Hilbert-Huang transform, or the like, or any combination thereof. During the process of the pre-treatment, the methods mentioned herein may be used in parallel or may be used in combination. Descriptions regarding methods and systems for reducing or removing noise from a physiological signal, e.g., a PPG signal or an ECG signal, may be found in, e.g., International Patent Application Nos. PCT/CN2015/077026 filed Apr. 20, 2015, PCT/CN2015/077025 filed Apr. 20, 2015, and PCT/CN2015/079956 filed May 27, 2015, each of which is incorporated by reference. Additionally, real-time transformation of time domain or frequency domain may also be implemented in step 520, and the signals or related information may be used in time domain, frequency domain, or both.

In step 530, the features of the first and second signals may be recognized or identified. In the exemplary context of blood pressure monitoring, the first signal or the second signal may include a PPG signal, an ECG signal, a BCG signal, or the like; exemplary features of the first signal or the second signal may include waveform, characteristic points (or fiducial points), peak points, valley points, amplitude, phase, frequency, cycle, or the like, or any combination thereof. For example, one characteristic point may be a peak or a valley of the first signal and a peak or a valley of the second signal, e.g., the peak of R wave of an ECG signal, a peak or a valley of the PPG signal, a fastest rising point of a PPG signal, a higher order moment or a higher order derivative of the PPG signal, a pulse area of the PPG signal, a maximum positive peak of S2 of a PCG signal, or a peak of an ICG signal, or the like.

In step 540, a parameter based on the recognized features of the first and the second signals may be calculated. In some embodiments, the time interval between the characteristic points of the first and second signals may be calculated. In one example, the time interval between the ECG fiducial point (typically the R peak, but may also use the Q/S peak, or even the peak of a P/T wave) and a fiducial point marking the pulse arrival is referred to as the PTT. In another example, the time interval between two pulse wave signals detected at different locations, e.g., between the carotid and femoral arteries, may be used as the PTT. Further PTTV may be approximated based on a group of determined PTT. HRV may be determined based a group of A RR. As used herein, ΔRR refers to a time interval between two adjacent R waves (the maximum point of a QRS waveform). More description regarding the determination of the PTT may be found elsewhere in the present disclosure in, for example, FIGS. 7 and 8 and the corresponding description.

In step 550, BP (blood pressure) values may be calculated based on the calculated parameter, e.g., the determined PTT (pulse transit time), PTTV (pulse transit time variation) and HRV, or the like, or a combination thereof. The calculation may be based on a calibrated model. The calibrated model may include a linear function or model, a nonlinear function or model. The calibration may be performed at step 560. The calibration may be performed periodically, upon a subject's instruction, or the like. The calibration may take time-varying properties into account. The time-varying properties may include, e.g., the arterial propagation path of a specific subject, the heart movement of a specific subject, the real-time temperature or humidity, the updated fiducial BP of a specific subject, the updated database storing historical data (SBP/DBP values, BP calculating algorithms, etc.) of a specific subject, the updated database storing reference data of people sharing the same or similar characteristics (e.g., age, gender, stature, weight, a body fat percentage, color of skin, a family health history, a life style, an exercise habit, diet, a psychological condition, a health condition, an education history, occupation, or the like, or any combination thereof), or the like, or any combination thereof.

While the foregoing has described what are considered to constitute the present disclosure and/or other examples, it is understood that various modifications may be made thereto and that the subject matter disclosed herein may be implemented in various forms and examples, and that the disclosure may be applied in numerous applications, only some of which have been described herein. Those skilled in the art will recognize that present disclosure are amenable to a variety of modifications and/or enhancements. For example, the pre-treatment step 530 may not be necessary. Additionally, a third signal may be acquired if needed, and the third signal may be a signal with the same type with the first signal or the second signal, or may be a signal different with the first signal or the second signal.

Figure 6:
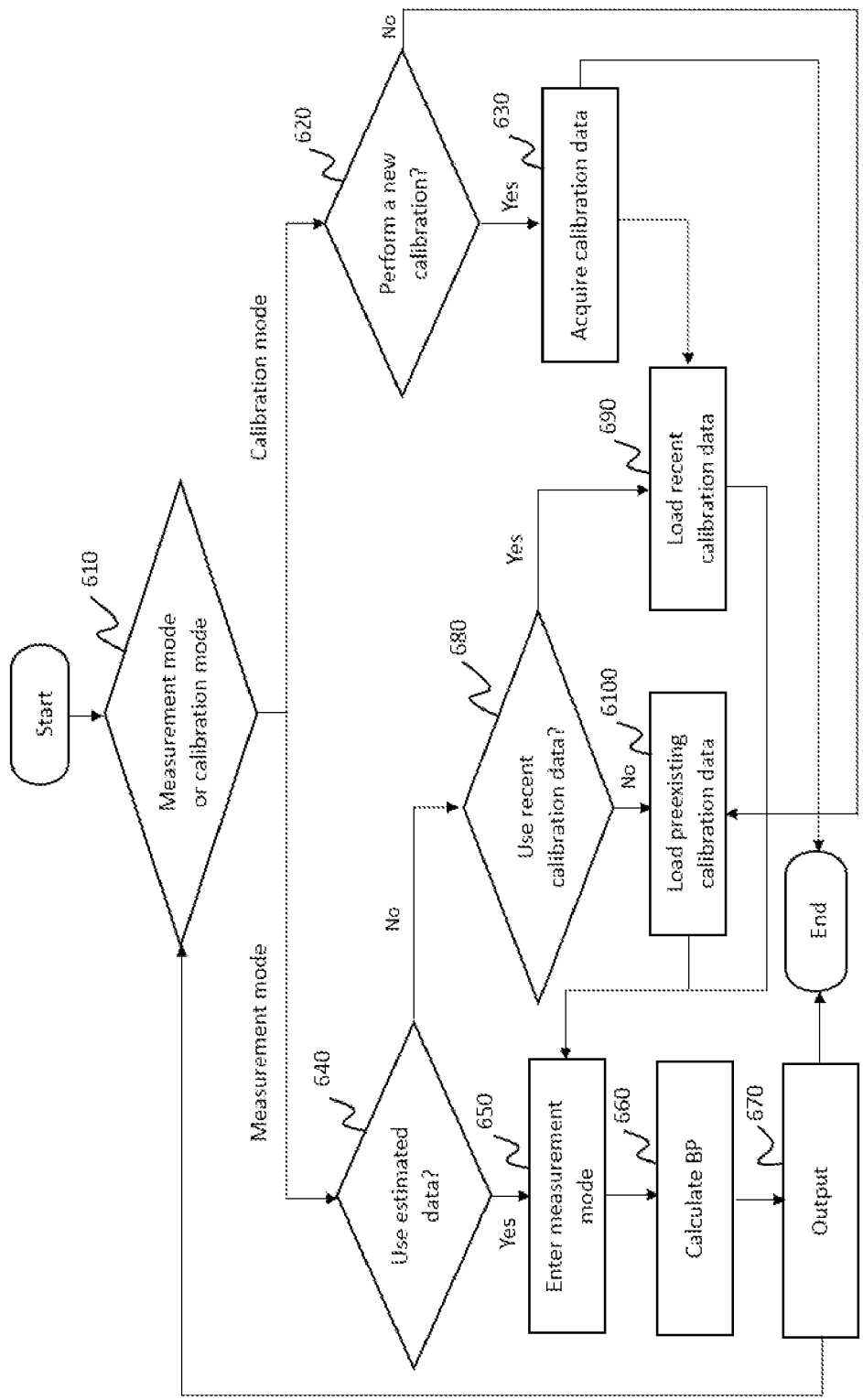
FIG. 6 is a flowchart showing a blood pressure estimation according to some embodiments of the present disclosure.

FIG. 6 is a flowchart showing an exemplary process for a blood pressure estimation according to some embodiments of the present disclosure. The process may be applicable to perform a measurement or a calibration. In some embodiments, a subject or a user other than the subject may determine whether a new calibration process is going to be carried out or preexisting calibration data or a calibrated function is going to be used. In step 610, a measurement mode or a calibration mode may be selected. If the calibration mode is selected, the process may proceed to step 620 to determine whether to perform a new calibration. If a new calibration is selected, calibration data may be acquired in step 630. The calibration data may include physiological parameters, information (e.g., environmental or personal information) relating to the physiological parameter, or the like, or a combination thereof. Exemplary physiological parameters may include PTT0, SBP0, DBP0, PTTV0, HRV0, or the like, or a combination thereof. Exemplary models may include different functions or same function with different coefficients. At least some of the functions may approximate or illustrate a correlation between a physiological parameter of interest and the acquired signals (or some features of the acquired signals). Exemplary functions may include different polynomials, e.g., polynomials of different degrees, polynomials of the same degree with different coefficients, or the like, or a combination thereof.

In some embodiments, the calibration data to be applied in a specific calibration or analysis may be selected based on input by a subject or a user other than the subject, acquired physiological information, acquired environmental information, historical data relating to the subject (e.g., historical data stored in a storage that may be accessed wirelessly or through wire transmission), or the like, or a combination thereof. For example, the calibration data associated with a physiological signal that is the same or similar to an acquired physiological signal may be selected to be applied in the calibration or the analysis. As another example, if some environmental information (e.g., a high room temperature, a low atmospheric pressure, or the like, or a combination thereof) is detected, calibration data relating to the same or similar conditions may be retrieved and applied in the calibration or the analysis. As a further example, a subject or a user other than the subject may specify which calibration data to apply in the calibration or the analysis. The collection of calibration data may be updated. The update may be based on, e.g., the physiological parameter of interest measured by way of one or more methods (e.g., direct measurements performed by a healthcare provider, or the like), historical data regarding one or more subjects, or the like, or a combination thereof.

If the measurement mode is selected, the process proceeds to step 640 in which the subject or a user other than the subject may be asked in step 640 whether estimated data is to be used. If the estimated data are selected to be used, then the requested estimated data may be retrieved from, e.g., a storage device or the server 120. As used herein, the estimated data may be empirical data. Exemplary estimated data may include empirical calibration data, e.g., user-set data or default system data. The empirical data may include one or more empirical functions or models that may be used to calculate or estimate a physiological parameter of interest. The empirical data may include statistical data based on data of a group of subjects. For example, the empirical data may be a function or model including determined coefficients for calculating parameters of interest. The function or model including the determined coefficients may be obtained based on one or more sets of calibration data from a group of subjects. In another example, the empirical data may be empirical calibration data, e.g., empirical parameters of interest.

Proceeding to entering the measurement mode in step 650, one or more physiological parameters including, for example, the BP, the SBP, the DBP or the like, or a combination thereof, may be calculated in step 660, and the results may be output in step 670. The output may be displayed or reported to the subject or a user other than the subject, printed, stored in a storage device or the server 120, transmitted to a device for further processing, or the like, or a combination thereof. Alternatively, the process may return from step 670 to one of the prior steps, e.g., the initial step 610, from which a new process may start.

If the estimated data are not selected in step 640, the process proceeds to step 680 to determine whether recent calibration data are selected to be used. If the recent calibration data are selected, then the recent calibration data may be loaded from, e.g., a storage device or from the server 120 in step 690. And the measurement mode based on the recent calibration data may be initiated in step 650. The BP may be calculated in step 660, and output in step 670. If the recent calibration data are not selected in step 680, preexisting calibration data may be loaded from, e.g., a storage device or from the server 120 in step 6100.

The preexisting calibration data may include historical data and peer data. The historical data may be personalized, acquired by prior calculations, measurements, or provided by a specific subject. The peer data may be acquired from the calculation or measurement results of a peer group or calibration data of a peer group. As used herein, the peer group is defined as a group of people sharing at least some same or similar characteristics, e.g., same gender, similar age, similar height, similar weight, similar arm length, similar illness history, or the like, or a combination thereof. It should be noted that, other than the peer data, the empirical data may be acquired by statistical analysis based on data of a group of subjects which is not limited to a peer group.

The measurement mode based on the preexisting calibration data may be initiated in step 650. The BP may be calculated in step 660, and output in step 670. Additionally, in the calibration mode, after the calibration data is acquired in step 630, the calibration data may be stored in a storage device or in the server 120 and then the process may be ended.

The selection of the calibration data may be achieved automatically, manually, or both. An automatic selection may be achieved according to instructions stored in, e.g., the system 100, the terminal 140, or the like, or a combination thereof. The instructions may include default instructions provided by, e.g., the system 100, instructions provided by a subject or a user other than the subject, or the like, or a combination thereof. In some embodiments, the default instructions may be relied on when there are no relevant instructions provided by a subject or a user other than the subject. A manual selection may be achieved according to, e.g., a selection made by a subject or a user other than the subject at or around the time of calibration or analysis. In some embodiments, the automatic selection may be performed when no manual selection is made. The default instructions regarding the selection of calibration data may be updated by, e.g., machine learning. The machine learning may be based on, e.g., prior manual selections made by the subject or a user other than the subject, acquired information and corresponding prior calculations or estimations of a physiological parameter of interest, or the like, or a combination thereof.

This description is intended to be illustrative, and not to limit the scope of the claims. Many alternatives, modifications, and variations will be apparent to those skilled in the art. The features, structures, methods, and other characteristics of the exemplary embodiments described herein may be combined in various ways to obtain additional and/or alternative exemplary embodiments. For example, one or more sets of calibration values may be acquired in step 630 from which at least one set of (e.g., optimum) coefficients may be loaded in step 690. The calibration/calculation may be conducted on a terminal connected to the device, wherein the terminal may be a mobile device with a processing unit.

Figure 7:
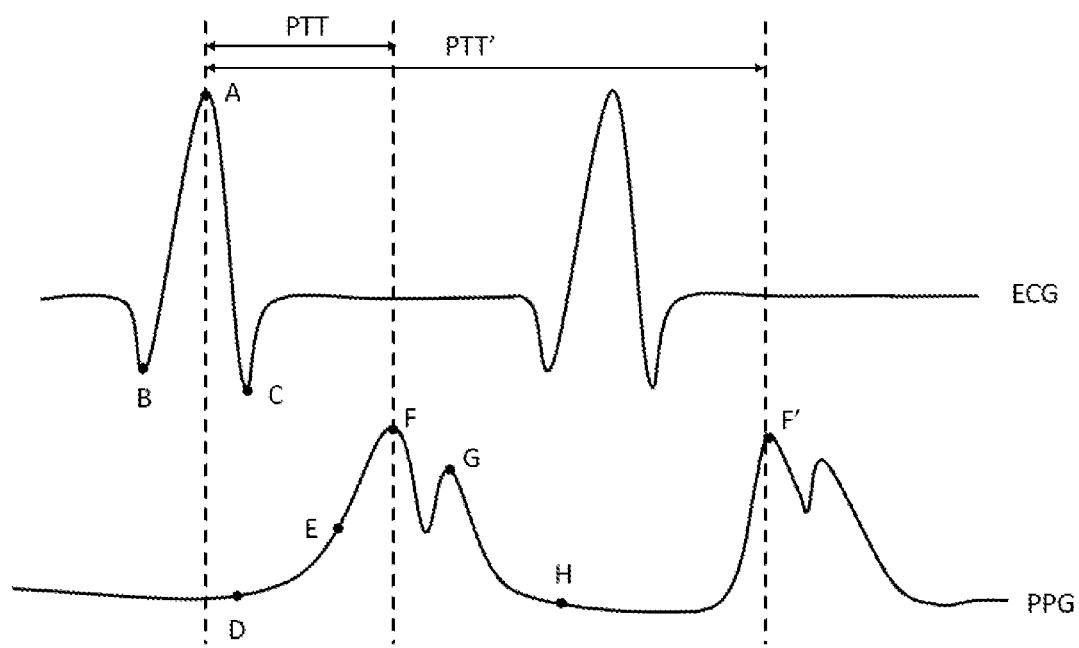
FIG. 7 is a schematic diagram showing the estimation of PTT according to some embodiments of the present disclosure.
Figure 8:
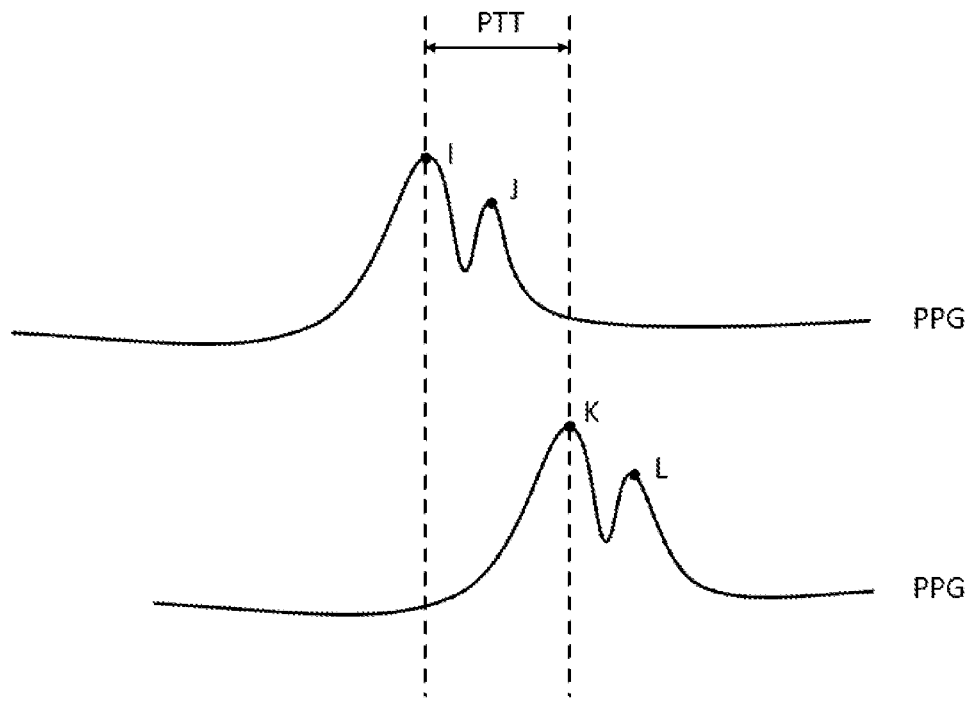
FIG. 8 is a schematic diagram showing the estimation of PTT according to some embodiments of the present disclosure.

FIG. 7 and FIG. 8 show schematic diagrams of measurement of PTT based on a PPG waveform or an ECG waveform. PTT (pulse transit time), defined as the time for a pulse pressure wave launched by a heartbeat to propagate through a length of the arterial tree, may be used to estimate or calculate a physiological parameter including, e.g., the BP, the SBP, the DBP, or the like, or a combination thereof. PTT may correlate with blood pressure, i.e. a variation in PTT indicates a variation in the blood pressure.

In one example, as shown in FIG. 7, PTT may be approximated by a time interval between a maximum point A on the QRS complex (indicating the peak of ventricular depolarization) on an ECG waveform and a peak point F on a PPG waveform (indicating the maximum value of pressure and volume of an artery). Alternatively, PTT may be approximated from other regions or points of the two waveforms (such as a point along a rising edge or a peak). PTT may be approximated by various combinations of the characteristic points of the two waveforms (also referred to as features of the two waveforms). For example, the characteristic points of interest may include the characteristic points A, B, and C on the QRS complex on the ECG waveform, the characteristic points D (indicating the beginning of the PPG waveform), E (indicating the maximum slope of the PPG waveform), G (the second peak point of the PPG waveform) and H (indicating the ending of the PPG waveform) on the PPG waveform.

In another example, PTT may be approximated by the time interval between the maximum point A on the QRS complex (indicating the peak of ventricular depolarization) on the ECG waveform and the point E on the PPG waveform (indicating the maximum slope of the PPG waveform). The point E indicating the maximum slope of the PPG waveform may be detected by a recognition method integrated in the recognition unit 420.

In a further example, PTT may be approximated by a time interval between the maximum point A on the QRS complex (indicating the peak of ventricular depolarization) on the ECG waveform and the onset point D on the PPG waveform (indicating the beginning of a volumetric increase in vasculature). It shall be understood to the person having ordinary skills in the art that the PTT value may be approximated by the time interval between any point of interest on ECG (e.g., point A, B or C) and any point of interest on PPG signal (e.g., point D, E, F, G, or H).

While the forgoing has described what are considered to constitute the present disclosure and/or other examples, it is understood that various modifications may be made thereto and that the subject matter disclosed herein may be implemented in various forms and examples, and that the disclosure may be applied in numerous applications, only some of which have been described herein. For example, the point of interest on the PPG waveform may be selected from a group of points located at any of the average portion. The average portion may be defined as an average position between any two points on the PPG waveform, e.g., D, E, F, G, H or any combination thereof.

In some embodiments, PTT may be approximated based on time-dependent waveforms other than the ECG and PPG waveforms. For example, PTT may be approximated by measuring a temporal separation between features in two or more time-dependent waveforms measured from the subject, such as a phonocardiogram (PCG) signal, an impedance cardiogram (ICG) signal, or any other physiological signal including the information of the heart or the vascular tone. As shown in FIG. 8, PTT may be approximated from two separate PPG waveforms measured by different sensors located at different parts or locations of the body of a subject. The sensors may be disposed on the subject body's fingers, wrist, arm, chest, or any other locations where a PPG signal may be measured. Measurements may be made using a sensor or a sensing unit based on, e.g., a transmission or reflection-mode optical electronic configuration. FIG. 8 illustrates that the points I, J, K and L may be used to approximate or calculate PTT.

PTT detected in a specific way may be used to estimate or calculate a physiological parameter including, e.g., the BP, the SBP, the DBP, or the like, or a combination thereof, based on a model or function and a set of calibration data (also referred to as calibration values). The set of calibration values may be retrieved in which the PTT in the calibration was detected in the same way. For example, in both the calibration and a real measurement, PTT values may be approximated by the time interval between a maximum point A on the QRS complex (indicating the peak of ventricular depolarization) on an ECG waveform and a peak point F on a PPG waveform (indicating the maximum value of pressure and volume of an artery) as illustrated in FIG. 7. As another example, in both the calibration and a real measurement, PTT values may be approximated by the time interval between a peak point I and a peak point K on a PPG waveform measured at two different locations on the body of the subject as illustrated in FIG. 8.

Returning to FIG. 7, the ECG waveform and the PPG waveform are cyclical signals, i.e. the characteristic points occur substantially cyclically or periodically. Thus it may be seen in FIG. 7 that PTT' is approximated by a time interval of the maximum point A on the QRS complex on the ECG waveform and a peak point F' on a subsequent (second) PPG waveform. Similarly, PTT" also may be approximated by a time interval between the peak point A on the QRS complex on the ECG waveform and a peak point F" (not shown in FIG. 7) on a further (third) PPG waveform. The value of PTT' and the value of PTT" are larger than that of PTT, and errors or deviations may occur while estimating blood pressure or other physiological parameters of interest based on such inaccurate PTT' and PTT" values. Such errors or deviations may be avoided by using a PPG waveform from the same cycle (driven by the same heart beat) as the ECG waveform. Thus during recognition of characteristic points of the PPG waveform, a threshold may be set regarding the time window or segment within which the characteristic points on the PPG waveform may be identified and used to determine PTT. In one example, the time window may be 2 seconds or less. Merely by way of example, an analysis to identify a fiduciary point on a PPG waveform is performed on a segment of the PPG waveform occurring within 2 seconds from the time point when point A on the ECG waveform is identified, in order to approximate the PTT. As another example, an analysis to identify a fiduciary point on a PPG waveform is performed on a segment of the PPG waveform occurring between two consecutive peak points A on the ECG waveform, in order to approximate the PTT.

The cycle of ECG or the cycle of PPG may vary. As an example, the cycle of ECG or the cycle of PPG of different subjects may be different. As another example, the cycle of ECG or PPG of the same subject may vary under different situations (e.g., when the subject is exercising or asleep, at different times of a day, at the same or similar time on different days), or the like, or a combination thereof. In one example, the time window threshold may be set based on the heart rate of a subject (for example, the cycle of average person is approximately 60-120 beats per minute). The heart rate may be an average value over a period of time (e.g., a week, a month, a year, or the like). The heart rate may be one measured at or around the acquisition time. The heart rate may be measured based on, e.g., the ECG signal, the PPG signal, or the like. The time window may be set or updated based on the measured heart rate. In another example, the time window may be set by, e.g., the system, the subject, or a user other than the subject, based on the physiological information of the subject. For example, the physiological information may include motion or not, taking medicine or not, good or bad mood, emotional stress or not, or the like, or a combination thereof. In another example, the time window may be a fixed value defined by the system, the subject, or a user other than the subject (e.g., his doctor, health care provider, or the like).

This description is intended to be illustrative, and not to limit the scope of the present disclosure. Many alternatives, modifications, and variations will be apparent to those skilled in the art. The features, structures, methods, and other characteristics of the exemplary embodiments described herein may be combined in various ways to obtain additional and/or alternative exemplary embodiments. It should be appreciated for those skilled in the art that the determination of PTT (pulse transit time) is not limited to the methods described above. For example, other pulse-wave-related signals may be used in replace of the PPG signal, such as a pressure wave signal, a blood flow signal and a phonocardiogram. In that case, PTT may be approximated by a time interval from a characteristic point on the ECG waveform to a characteristic point on any of the selected pulse-wave-related signals. In general, PTT may be approximated from various combinations of these signals, e. g., between any two pulse-wave-related signals acquired by the acquisition module 210. In other words, PTT may be approximated based on any two signals indicating a time interval between the beginning of the pulse in the aorta of the subject and the arrival of the pulse in the peripheral of the subject.

After PTT is approximated, PTTV may be further determined based on the approximated PTT. For example, PTTV may be determined by equation 1 based on a group of PTT. As used herein, $\Delta PTT_i$ refers to the difference between two PTTs determined based on characteristic points of two consecutive waveforms (e.g., two consecutive ECG waveforms, and two corresponding consecutive PPG waveforms).

$$PTTV = \sqrt{\frac{\sum_{i=2}^{N}(\Delta PTT_i - \overline{\Delta PTT})^2}{N-1}}, \qquad \text{Equation 1}$$

Further, HRV may be determined. For example, HRV may be evaluated at time domain, such as Equation 2 based on a group of $\Delta RR$. As used herein, in one example, $\Delta RR$ refers to a time interval between two adjacent R waves (the maximum point of a QRS waveform). In another example, $\Delta RR$ may refer to a time interval between any two adjacent characteristic points on different QRS waveforms.

$$HRV = \sqrt{\frac{\sum_{i=2}^{N}(\Delta RR_i - \overline{\Delta RR})^2}{N-1}}, \qquad \text{Equation 2}$$

It should be appreciated for those skilled in the art that the determination of HRV (heart rate variation) is not limited to the methods described above. For example, other time domain variables may be used to evaluate HRV. The time domain variables may include mean RR interval, mean heart rate, the difference between the longest and short RR interval, the difference between a nighttime heart rate and a daytime heart rate, or the like, or a combination thereof. Additionally, HRV may be evaluated in a frequency domain.

FIGS. 9-A through 9-D provide an exemplary process according to some embodiments of the present disclosure. FIG. 9-E provides a schematic showing the relationships among different analysis levels, and each level is provided with one specific example. Measured data (M) (e.g., acquired information) and calibration values (C) may be received in step 901, and then whether to perform optimization may be chosen in step 902. If a model optimization is to be performed, it may follow at least some steps starting from node A 903 as illustrated in FIG. 9-B. Otherwise, at least some steps in a process that may estimate the value of blood pressure based on measured data may be performed.

In step 904, one or more favorite models may be retrieved based on the subject's personal data 1110, universal data 1120, additional information in a history 1112, or the like, or a combination thereof. As used herein, a favorite model may refer to a model 900-5 that may provide a more accurate estimate of a physiological parameter of interest from acquired information than one or more other models 900-5. The information may be acquired from the library 1100 as described in FIG. 11, or may be measured by a variety of sensors. The sensors may be part of the system 100, or communicate with the system 100. Exemplary sensors may include an accelerometer configured to measure the movement conditions of a subject during a measurement, a heart rate sensor configured to measure a subject's heart rate during a measurement, a GPS receiver or location sensor configured to measure the geographic location where a measurement occurs or the subject is located, a temperature sensor configured to measure the environment temperature and/or the body temperature of a subject at or around an acquisition time, a humidity sensor configured to measure the environment humidity at or around an acquisition time, or the like, or a combination thereof. The retrieved favorite model(s) may be used to estimate blood pressure based on the acquired signals or information.

As shown in FIG. 9-E, a model 900-5 may include but is not limited to a factored function 900-3, and a mathematical processing 900-4. Moreover, a factored function 900-3 may include but is not limited to a function (ƒ) 900-1, and a coefficient (or a set of coefficients) (B) 900-2. The coefficient (B) 900-2 may have more than one dimensions. A mathematical processing 900-4 may represent one or more types of mathematical processing 900-4, no mathematical processing 900-4, or the like, or a combination thereof. Examples of a function (ƒ) 900-1, a factored function 900-3, and a model 900-5 are provided in parts 900-1.1, 900-3.1, and 900-5.1, respectively, as illustrated in FIG. 9-E. In the exemplary context of estimating blood pressure based on PTT, any function (ƒ) 900-1 may be tested for fitting a blood pressure-PTT function. Functions (ƒ) 900-1 may include, for example, a linear function, a quadratic function, a cubic function, a 4th degree polynomial, an nth degree polynomial, an exponential function, a logarithmic function, a trigonometric function, an anti-trigonometric function, a hyperbolic function, or the like, or a combination thereof. The above mentioned examples of functions are provided for illustration purposes and not intended to limit the scope of the present disclosure. A function may be of another type, such as a spline function.

Two different models 900-5 may have different factored functions 900-3, or different types of mathematical processing 900-4, or a combination thereof. For example, two different models 900-5 may include two completely different factored functions 900-3, two same factored functions 900-3 that are subject to different mathematical processing 900-4, two same factored functions 900-3 in which one is subject to mathematical processing 900-4 and the other is not, or the like, or a combination thereof. Two different factored functions 900-3 may have different functions (ƒ) 900-1, or different sets coefficient (B) 900-2, or a combination thereof. For example, two different factored functions 900-3 may include two different functions (ƒ) 900-1 that have different sets coefficient (B) 900-2, two same functions (ƒ) 900-1 that have two different sets coefficient (B) 900-2. As used herein, if two factored functions 900-3 are the same except for one or more coefficients (B) 900-2 of the corresponding segment(s) including the variable of the same degree or order (e.g., $x^{-3}$, $x^{-2}$, $x^{-3}$, or the like, in which x is the variable), they are considered to fall in the scope of the same function (ƒ) 900-1. If two models 900-5 are the same except that they are subject to different mathematical processing 900-4 (e.g., log(x), $e^{(x-1)}$, or the like, in which x stands for M and/or C), the two models 900-5 are considered to fall in the scope of a same factored function 900-3. Merely by way of example, a first factored function 900-3 illustrated in Equation 3.1 and a second factored function 900-3 illustrated in Equation 3.2 are as follows:

$$g_1(x)=x^2-x+2, \qquad \text{Equation 3.1}$$

$$g_2(x)=3x^2-5, \qquad \text{Equation 3.2}$$

$$g_3(x)=x^3-2, \qquad \text{Equation 3.3}$$

Equation 3.1 and Equation 3.2 are considered to represent different factored function 900-3 but fall within the scope of the same function 900-1. Equation 3.1 and Equation 3.3 are considered to represent different factored functions 900-3 and fall within the scope of different functions (ƒ) 900-1. As another example, a fourth factored function 900-3 illustrated in Equation 3.4 and a fifth factored function 900-3 illustrated in Equation 3.5 are as follows:

$$g_4(x)=2e^x+6e^{x-1}-3e^{x-2} \qquad \text{Equation 3.4}$$

$$g_5(x)=2e^N+3e^{x-1} \qquad \text{Equation 3.5}$$

Equation 3.4 and Equation 3.5 are considered to represent different factored function 900-3 but fall within the scope of the same function (ƒ) 900-1. Equation 3.1 and Equation 3.4 are considered to represent different factored function 900-3 and fall within the scope of different functions (ƒ) 900-1.

In step 905, measured data (M) and/or calibration values (C) may be processed mathematically according to a favorite model retrieved in step 904. For example, some of the retrieved favorite models may include the mathematical processing 900-4 including transformation, segmentation, differentiation, integration of the data and/or values, or the like, or a combination thereof. Transformation may be, for example, Fourier transform, wavelet transform, orthogonal polynomial transform, discrete orthogonal polynomial transform, Hilbert-Huang transform, or the like, or a combination thereof. Differentiation and/or integration may be used to construct differential equations in order to provide a more suitable model 900-5. The above mentioned examples of mathematical processing 900-4 are provided for illustration purposes and not intended to limit the scope of the present disclosure. Other types of mathematical processing 900-4 may also be used in step 905. For example, algebraic operations may be used in step 905 according to a model 900-5.

Some of the models 900-5 may include mathematical processing 900-4. Some of the models 900-5 may include mathematical processing 900-4 in some cases (e.g., calculating one parameter of interest) and may include no mathematical processing 900-4 in some other cases (e.g., calculating another parameter of interest); some of the models 900-5 may have different versions that include different types of mathematical processing 900-4, and one of the versions may include no mathematical processing 900-4; some of the models 900-5 may include no mathematical processing 900-4 at all. Some examples regarding the relationship of mathematical processing 900-4, factored functions 900-3, and models 900-5 are listed below:

Model 1: ƒ(x)=4x²+3x+2, always subject to Fourier transform,

Model 2: ƒ(x)=4x²+3x+2, subject to wavelet transform only for DBP estimations, but no mathematical processing needed for SBP estimations, and Model 3: ƒ(x)=ln x+e$^n$, subject to no mathematical processing.

Model 1 and Models 2 represent two different models 900-5, but fall in the scope of the same factored function 900-3; whereas, Model 1 and Model 3 represent two different models 900-5, and fall in the scope of two different factored functions 900-3.

In step 906, a determination may be made as to whether different models 900-5 are to be used for calculating the SBP and the DBP. The determination may be made by the system or a portion thereof (e.g., based on an instruction provided by a subject, a user other than the subject, or an instruction or a rule derived by machine learning of prior data, prior behaviors of the subject, or of a user other than the subject), or by the subject, or by a user other than the subject. Different or same favorite model(s) may be appropriate for different subjects. Different or same favorite model(s) may be appropriate for a same subject. The physiological parameters of interest (i.e., SBP, DBP, and etc.) may be fitted with different models 900-5. The fitting models 900-5 for different physiological parameters of interest may be same or may be different based on acquired information or input.

For a same subject, different models 900-5 may be used to calculate or estimate SBP and DBP. For some different subjects, a same model 900-5 may be used to calculate or estimate SBP or DBP. For instance, a same model 900-5 may be used to calculate or estimate SBP for at least two different subjects. As another example, a same model 900-5 may be used to calculate or estimate DBP for at least two different subjects. In a further example, a same model 900-5 may be used to calculate or estimate SBP for at least two different subjects, and two different models may be used to calculate or estimate DBP for at least two different subjects, or vise versa. In a still further example, for at least two different subjects, two different models may be used to calculate or estimate SBP, and two different models may be used to calculate or estimate DBP. As described elsewhere in the present disclosure, in some embodiments, the different models 900-5 may include different functions 900-1. In some embodiments, the different models 900-5 may include a same function 900-1 but different factored functions 900-3. In some embodiments, the different models 900-5 may include a same factored function 900-3 but different mathematical processing 900-4. Examples of using different models 900-5 for estimating blood pressure values under different conditions for a same subject or for different subjects may be found in the description of FIGS. 15-A to 15-D.

In step 907, a determination may be made as to whether to use a localized analysis. The determination may be made by the system or a portion thereof (e.g., based on an instruction provided by a subject, a user other than the subject, or an instruction or a rule derived by machine learning of prior data, prior behaviors of the subject, or of a user other than the subject), or by the subject, or by a user other than the subject. As used herein, a localized analysis may refer to a calculation that only considers the set(s) of calibration values (C) that occurred in time close to the measured data (M) for a specific occasion, or that are close in value to the current measure data (M) for a specific occasion. Accordingly, one or more sets of calibration values are selected in step 909. For example, under on specific condition of the localized analysis, only the calibration values (C) occurred within an interval may be considered as suggested in Equation 4:

$$\{C=(PTT_0, Blood\ Pressure_0)|PTT-a<PTT_0<PTT+b\} \quad \text{Equation 4}$$

In some embodiments, constants a and b in Equation 4 may be pre-defined independently of a specific measurement. In some embodiments, constants a and b in Equation 4 may be determined for a specific measurement. The constants may be determined based on, e.g., the acquired information and the physiological parameter of interest (e.g., the blood pressure), from the subject, or from other subjects (e.g., a sub-group of a general population). The sub-group may share a same or similar characteristic including, for example, age, gender, nation, stature, weight, a body fat percentage, color of skin, a family health history, a life style, an exercise habit or other habit, diet, occupation, illness history, education background, marital status, religious belief, or the like, or any combination thereof. The value of a and the value of b may be specified by a subject, a user other than the subject, the system 100, or the like.

In one example, the measured PTT is 1 second, and only one or more sets of calibration values (C) with a PTT0 value falling within the range from 1−a second and 1+b second may be considered. The value of a and the value of b may be the same or different. Merely by a way of example, the value of a is factor1*PTT, the value of b is factor2*PTT. The factor1 and factor2 may be any number in the range of (0, 1). In some embodiments, factor1 or factor2 may be 2%, or 5%, or 8%, or 10%, or 12%, or 15%, or 20%, or 25%, or larger than 25%. In some embodiments, factor1 or factor2 may be lower than 50%, or lower than 40%, or lower than 30%, or lower than 25%, or lower than 20%, or lower than 15%, or lower than 12%, or lower than 10%, or lower than 8%, or lower than 5%. Factor1 and factor2 may be the same or different.

In some embodiments, under the localized analysis, only one or more sets of calibration values (C) based on one or more calibration procedures occurred within a certain time frame may be used. The time frame may be, e.g., within a day, within a week, within 10 days, within 2 weeks, within three weeks, within a month, within two months, within three months, within four months, within five months, within six months, within one year, or the like. In some embodiments, one set of calibration values satisfies the criteria according to Equation 4 or within a specified time frame, and may be selected to be used in further steps of the process.

In some embodiments, the process is semi-personalized where only the calibration values based on a calibration procedure performed on the subject may be used in the process for estimating the physiological parameter of interest according to a model 900-5 for the subject; other parts of the model 900-5 (e.g., one or more coefficients (B) 900-2 of the model 900-5) may be based on data from other subjects. In some embodiments, the process is personalized where only the calibration values based on a calibration procedure performed on the subject may be used in the process for estimating the physiological parameter of interest according to a model for the subject; other parts of the model (e.g., one or more coefficients (B) 900-2 of the model 900-5) may also be based on data from the subject. In some embodiments, the process is not personalized where the calibration values based on a calibration procedure performed on any subject may be used in the process for estimating the physiological parameter of interest according to a model 900-5 for the subject; other parts of the model 900-5 (e.g., one or more coefficients (B) 900-2 of the model 900-5) may be based on data from any subjects. Such a subject may be the subject whose physiological parameter is assessed, or one sharing a same or similar characteristic with the subject.

In step 908 or step 910, the DBP and the SBP are estimated based on the PTT, and the selected one or more sets of calibration values (C) (also referred to calibration data), and favorite model(s. As used herein, one set of calibration data or values may refer to those acquired in one calibration process or procedure. If two different favorite models for SBP and DBP are selected, the SBP and DBP values may be generated from the different favorite models.

FIG. 9-B illustrates the process starting from node A 903 regarding a model optimization according to some embodiments of the present disclosure. In step 912, when a determination is made to perform optimization, multiple (n) models 900-5 may be selected from the library 1100. The favorite models may be more likely to generate better results in the specific assessment of the subject, as compared to other models 900-5 in the library 1100.

The process may proceed to steps 905 and 906 in a manner similar to that described above in connection with FIG. 9-A. If a determination is made not to use separate models 900-5 for estimating the SBP and the DBP, the remaining steps shown in FIG. 9-B may be skipped to proceed to node B 913. When a determination is made to use different models 900-5 for estimating the SBP and the DBP in step 906, a determination is made whether a localized analysis is performed in step 907. The determination may be made by the system or a portion thereof (e.g., based on an instruction provided by a subject, a user other than the subject, or an instruction or a rule derived by machine learning of prior data, prior behaviors of the subject, or of a user other than the subject), or by the subject, or by a user other than the subject. If a localized analysis is to be performed, one or more sets of calibration values are selected in step 909, as that described in connection with step 909 in FIG. 9-A.

In step 914, a regression analysis may be performed based on one or more sets of calibration values (C) in connection with each one of the retrieved favorite models. As used herein, a regression analysis may be performed to generate functions (ƒ) 900-1, factored functions 900-3 or models 900-5 (or segments of functions (ƒ) 900-1, factored functions 900-3 or models 900-5). The generated functions (ƒ) 900-1, factored functions 900-3 or models 900-5 may be configured to calculate parameters of interest. The one or more sets of calibration values (C) may affect coefficients B (according to, e.g., Equation 6.1B), B' (according to, e.g., Equation 6.2B), and B" (according to, e.g., Equation 8.2B) used in a model 900-5. Coefficients B, B', and B" and measured data (M) may be used to calculate blood pressure according to a model 900-5.

Equations 5.1, 5.2, and 5.3 provide examples of such an analysis. β, β', and β" (see below) represent coefficients (B) 900-2 in models 900-5, and these coefficients (B) 900-2 may be determined by conducting a regression analysis based on n sets of calibration values (C). Coefficients β, β', and β" 900-2 may have various dimensions. Coefficients (B) 900-2 may be applied to functions (ƒ) 900-1 by different mathematical operations to generate factored functions 900-3. Mathematical operations may include addition, subtraction, multiplication, subtraction, exponent, power, logarithm, and the like, and any of the combinations. Functions (ƒ) 900-1 may be different for each set of SBP and DBP calculation as described herein in connection with step 910, but otherwise, functions (ƒ) 900-1 may be the same or different from each other. For example, function ƒ1 may be different from function ƒ1', but may be the same as function ƒ2. Function ƒ1 may be the same as function ƒ2'.

$$sbp_1 \approx f_1(PTT, \beta_1), dbp_1 \approx f'_1(PTT, \beta'_1) \quad \text{Equation 5.1}$$

$$sbp_2 \approx f_2(PTT, \beta_2), dbp_2 \approx f'_2(PTT, \beta'_2) \quad \text{Equation 5.2}$$

$$\ldots$$

$$sbp_n \approx f_n(PTT, \beta_n), dbp_n \approx f'_n(PTT, \beta'_n) \quad \text{Equation 5.3}$$

In step 915, blood pressure results, coefficients, and errors related to the analysis in step 914 are calculated. Equations 6.1A, 6.1B, 6.1C, 6.2A, 6.2B, and 6.2C are examples of the results, coefficients, and errors generated in step 915. In Equations 6.1A, 6.1B, 6.1C, 6.2A, 6.2B, and 6.2C, sbp1|ptt represents the SBP value calculated using f1, when PTT value equals to ptt from the measured data (M), and the rest of such expressions may be interpreted in the same manner. E, E', and E" (see below) represents the errors, or sometimes referred to as residuals, of the regression analysis. In Equations 6.1A-6.1C, and 6.2A-6.2C, SBP, DBP, B, B', E, and E' are expressed in the form of a matrix, but the generated results, coefficients, and errors may also be in other forms, such as sequences.

$$SBP = \begin{bmatrix} sbp_1 \mid ptt \\ sbp_2 \mid ptt \\ \vdots \\ sbp_n \mid ptt \end{bmatrix} \quad \text{Equation 6.1A}$$

$$B = \begin{bmatrix} \beta_1 \\ \beta_2 \\ \vdots \\ \beta_n \end{bmatrix} \quad \text{Equation 6.1B}$$

$$E = \begin{bmatrix} e_1 \\ e_2 \\ \vdots \\ e_n \end{bmatrix} \quad \text{Equation 6.1C}$$

$$DBP = \begin{bmatrix} dbp_1 \mid ptt \\ dbp_2 \mid ptt \\ \vdots \\ dbp_n \mid ptt \end{bmatrix} \quad \text{Equation 6.2A}$$

$$B = \begin{bmatrix} \beta'_1 \\ \beta'_2 \\ \vdots \\ \beta'_n \end{bmatrix} \quad \text{Equation 6.2B}$$

$$E' = \begin{bmatrix} e'_1 \\ e'_2 \\ \vdots \\ e'_n \end{bmatrix} \quad \text{Equation 6.2C}$$

After the blood pressure results, coefficients, and errors are generated in step 915, the process may proceed to node B 913 and continue to use measured data (M) and calibration values (C) to calculate in the case where SBP and DBP are analyzed using separate models 900-5.

As shown in FIG. 9-C, the above mentioned process may start from node B 913, steps 907 and 909 are performed as already described. In step 916 a regression analysis with retrieved favorite models may be performed in a manner similar to that in step 914. In step 917, regression results, coefficients, and errors are calculated. Specific examples illustrating step 916 and step 917 are provided in Equations 7.1, 7.2, 7.3, and 8A-8C. BP (bp$_1$, bp$_2$, and bpn) may include SBP and DBP (sbp and dbp) values.

$$bp_1 \approx f''_1(PTT, \beta''_1) \quad \text{Equation 7.1}$$

$$bp_2 \approx f''_2(PTT, \beta''_2) \quad \text{Equation 7.2}$$

$$\ldots$$

-continued $$bp_n \approx f_n''(PTT, \beta_n'') \qquad \text{Equation 7.3}$$

$$BP = \begin{bmatrix} bp_1 \mid ptt \\ bp_2 \mid ptt \\ \vdots \\ bp_n \mid ptt \end{bmatrix} \qquad \text{Equation 8A}$$

$$B'' = \begin{bmatrix} \beta_1'' \\ \beta_2'' \\ \vdots \\ \beta_n'' \end{bmatrix} \qquad \text{Equation 8B}$$

$$E'' = \begin{bmatrix} e_1'' \\ e_2'' \\ \vdots \\ e_n'' \end{bmatrix} \qquad \text{Equation 8C}$$

From node C 918, models 900-5 may be further refined, and related results, coefficients, and errors be calculated. As shown in FIG. 9-D, in step 919 the mathematical processing 900-4 used in step 905 may be inversely performed (if applicable according to models 900-5). In step 920, a determination may be made as to whether to compare the blood pressure results and errors generated in steps 909 and 917 with historical and peer data. If a determination is made to compare the blood pressure results and errors, historical data and peer data may be retrieved from, e.g., the library 1100, in step 921, and comparison between the current blood pressure results and errors with those stored in, e.g., the library 1100, are made in step 922. Historical data may be stored in, e.g., history 1112 in the subject's personal data 1110, and peer data may be the data gathered from, e.g., personal data 1110, according to one or more logical judgements 1122. Details regarding historical data and peer data will be explained later in the description of FIG. 11.

Generally, less errors (E, E', E") correspond to better regression performances and therefore better models 900-5. Comparing results and errors generated by different models 900-5 (obtained in the regression analysis) may assist assessing different models 900-5 in order for the system 100 to determine the appropriate blood pressure results to output and the favorite model(s) for a next measurement. If a determination is made not to make the comparison, steps 921 and 922 may be skipped, and the process proceeds to step 923.

In some embodiments, measured data (M) and calibration values (C) with historical data or peer data retrieved in steps 923 or 925 may be compiled. When historical data is to be compiled and analyzed with measured data (M) and calibration values (C), step 924 may be performed and the compiled data may then be sent to node A 903 and the steps starting from node A 903 may be repeated. When peer data is to be compiled and analyzed with measured data (M) and calibration values (C), step 926 may be performed and the compiled data may then be sent to node A 903 and the steps starting from node A 903 may be repeated. After the analysis with historical data and/or peer data is completed, or skipped, functions (f, f', f"), results (SBP, DBP, BP), coefficients (B, B', B") and errors (E, E', E") may be updated and stored in the library 1100 in step 927.

FIGS. 9-A, 9-B, 9-C, and 9-D only demonstrate examples of the model calculation and optimization processes. Some steps shown in FIGS. 9-A to 9-D may be omitted or performed in a different order. For example, step 920 may also be performed after step 925.

FIGS. 10-A and 10-B provide an example illustrating the calibration process of the system. Calibration values (C) as described herein, above, and below, may have a variety of sources, may be in two or more dimensions, and may have a regular or irregular pattern. Furthermore, sources of calibration values (C) may include, without limitations to, clinic or home measurements using any one or any combination of an auscultatory device, an oscillometric device, an ECG management device, a PPG management device, and a wearable device. Calibration values (C) may have multiple dimensions including, without limitations to, any two or more of PPG values, ECG values, BCG values, BP values, SBP values, DBP values, PR values, HR values, HRV values, cardiac murmur, blood oxygen saturation values, blood density values, pH values of the blood, bowel sound, brainwave, fat contents, and blood flow rates. Calibration values (C) may also have one or more periodical or non-periodical patterns. For example, calibration values (C) may have cyclic patterns, with at least part of its values changes cyclically every day, every week, every month, every year, or between any lengths of time. In another example, calibration values (C) may be acquired from previous blood pressure estimated by the system as described elsewhere in the present disclosure.

When the system is started for the first time, it may receive initialization data in step 1001. Initialization data may be received from various means, such as, user input, data detected by sensors, information extracted from connected sources, etc., and such data may include, but not limited to, subject's age, gender, race, occupation, health condition, medical history, life style, marital status, and other personal information. The above mentioned examples of initialization data are only to provide a better understanding, initialization data may also be other types of data and may be accessed from other sources, for example, mental health conditions that are related to the subject's social information. Initialization data may also be uploaded to a header 1111 in the library 1100. Initialization data may be used to find the subject's peer data if a determination is made not to use default calibration values (C) in step 1002. The determination may be made by the system or a portion thereof (e.g., based on an instruction provided by a subject, a user other than the subject, or an instruction or a rule derived by machine learning of prior data, prior behaviors of the subject, or of a user other than the subject), or by the subject, or by a user other than the subject.

On the other hand, the determination may be made to use default values according to the subject's suggestion or due to insufficient input in step 1001. The determination may be made by the system or a portion thereof (e.g., based on an instruction provided by a subject, a user other than the subject, or an instruction or a rule derived by machine learning of prior data, prior behaviors of the subject, or of a user other than the subject), or by the subject, or by a user other than the subject. Default calibration values (C) may include calibration values (C) that are appropriate for multiple subjects (e.g., multiple average healthy subjects). When it is determined not to use default values, the system may then proceed to step 1004 to retrieve peer data from, e.g., library 1100. In step 1005 the system may then compare initialization data with peer data to estimate initial calibration values (C) in step 1006. Furthermore, in a specific example, this process may be explained as: when one subject has insufficient calibration values (C) of his own, the system may gather calibration values (C) from other subjects, who closely fit the subject's initialization data, and then generate estimated calibration values (C) for the subject to use in his next measurement.

The system may then proceed to node D 1007 and continue the calibration process. After updating calibration values (C) stored in the system, e.g., in the library 1100 in step 1008, the system may detect whether new calibration values (C) are inputted (step 1009); calibration values (C) are updated in library 1100 (step 1011); or the subject has started a new blood pressure measurement (step 1012). If either new calibration values (C) input or calibration values (C) update occurred, the system may go to node E 1010 and start the refinement and analysis of calibration values (C). If a new measurement has been requested, the system may use the latest updated calibration values (C) with the acquired measured data (M) in step 1013 as well as upload the measured data (M) to library 1100 in step 1014. It is noticed that step 1014 may be skipped, and the system may access the measured data (M) and calibration values (C) in step 1013 and then start the process described in FIGS. 9-A, 9-B, 9-C, and 9-D to perform model optimization and/or to generate blood pressure results. The calibration values (C) used in Step 1013 may be selected from the calibration values (C) in or accessible from the system. Such selection may be based on, for example, measured data (M), additional information in history 1112, and reference 1113. In a specific example, calibration values (C) may be selected according to the cycle length. During a measurement, the calibration values (C) achieved within a time period or in a preceding measurement may be used.

As shown in FIG. 10-B, at least some steps starting from node E 1010 may be used to refine calibration values (C) when calibration values (C) are newly inputted or updated in library 1100. In step 1015 and step 1017, a determination is made whether to include other data or to conduct statistical analysis on calibration values (C), respectively. The determination may be made by the system or a portion thereof (e.g., based on an instruction provided by a subject, a user other than the subject, or an instruction or a rule derived by machine learning of prior data, prior behaviors of the subject, or of a user other than the subject), or by the subject, or by a user other than the subject. By choosing "no" in steps 1015 or 1017, steps 1016 or 1018 may be skipped. In step 1016 when data other than the newly inputted or updated calibration values (C) are to be used, the system may compile calibration values (C) in historical data and/or peer data with new calibration values (C). When to reduce data size is preferred in step 1017, the system may use statistical analysis and select candidate calibration values (C) in step 1018. In a specific example, statistical analysis may eliminate some outliers in calibration values (C), reduce data size, or elect more reliable calibration values (C) for further calculations.

The system may again start from node A 903 to test candidate calibration values (C) in different models 900-5 with the steps shown in FIGS. 9-B, 9-C, and 9-D. When the process in FIGS. 9-B, 9-C, and 9-D is completed, blood pressure results and errors related to each set of candidate calibration values (C) may be compared in step 1019. In step 1019, different variables (e.g., functions (f) 900-1, coefficients (B) 900-2, models 900-5, and calibration values) are controlled by running a first model 900-5 with different sets of candidate calibration values (C), and compare first sets of generated results and errors. A second model 900-5 with different sets of candidate calibration values (C) may then be run, and second sets of generated results and errors may be compared. The results from step 1019 may be send to node D 1007 for further possible events.

FIGS. 10-A and 10-B only provide an example of the calibration process, and some of the steps shown in FIGS. 10-A and 10-B may be omitted or changed in orders. For example, step 1001 receive initialization data may be skipped when the system chooses to use default calibration values (C).

FIG. 11 is an example of the composition and organization of library 1100. Library 1100 may be stored locally on a measuring device 110, or a terminal 140. Library 1100 may have different sections with different access control levels. Personal data 1110 may record data and information associated with each individual users, but a subject may have different access permits to different parts of personal data 1110. For example, Subject 1's personal data 1110-1, Subject 2's personal data 1110-2, and Subject N's personal data 1110-N may be stored in library 1100, but Subject 1 may only have full access to his/her personal data 1110-1 and limited access to other user's personal data 1110-2 and 1110-N.

Personal data 1110 may further include, but not limited to, headers 1111, histories 1112, and preferences 1113. Additionally, a header 1111 may have a subject's basic information and medical records. A header 1111 may include, but not limited to, subject's age, gender, race, occupation, health condition, medical history, life style, marital status, and other personal information. A history 1112 may record measured data (M), calibration values (C), results (SBP, DBP, BP) and additional information associated with every measurement and/or calibration. Furthermore, additional information may be any internal or external variables occurred when a subject is conducting a measurement and/or calibration. External variables may include, room temperature, humidity, air pressure, weather, climate, time, and date, etc. Internal variables such as, body temperature, metabolism rate, mood, level of activity, type of activity, diet, and health condition, etc. The above mentioned examples of additional information are only to provide a better illustration, additional information associated with each measurement and/or calibration may be other types of information, such as viscosity and other rheological data of a subject's blood. In some embodiments, the concepts of additional information and information recorded in a header 1111 are interchangeable. When some information originally recorded in a header 1111 changes with each measurements, it may also be considered as additional information.

Preference 1113 may have information associated with models 900-5, for example, a subject's favorite models and coefficients, and favorite models applicability, indicating which favorite model(s) are used under what kind of conditions or with what additional information. A subject's historical data may refer to all the information stored under a history 1112. Preference 1113 may also include a rating of a subject, which rates the reliability of the subject's personal data and may be considered as a weight factor when sorting the subject's personal data into peer data. For example, a subject who uploads calibration values (C) every week may have a better rating as compared to another subject who only calibrates once every year. The above mentioned examples of information recorded in a preference 1113, and a preference 1113 may include other information, such as which part of personal data 1110 a subject is willing to share with other users or organizations.

Universal data 1120 may include some non-private or non-personalized data, which may be accessed by other users or subjects. Universal data 1120 may include the records of the database of all the models 900-5, logics, and public data, for example, models and coefficients 1121, logical judgments to sort peer data from personal data 1122, and statistical results related to calibration values 1123. Peer data may be sorted from multiple subjects' personal data 1110, and logical judgments to sort peer data from personal data 1122 serve to find most closely related data according the subjects' headers 1111, and additional information in histories 1112. Logical judgments to sort peer data from personal data 1122 may also consider ratings in preferences 1113 to weigh the data acquired from different subjects. The above mentioned examples of information recorded in universal data 1120 are only to provide a better illustration, and universal data 1120 may also include other information such as errors (E, E', E") associated with each regression analysis.

Figure 12:
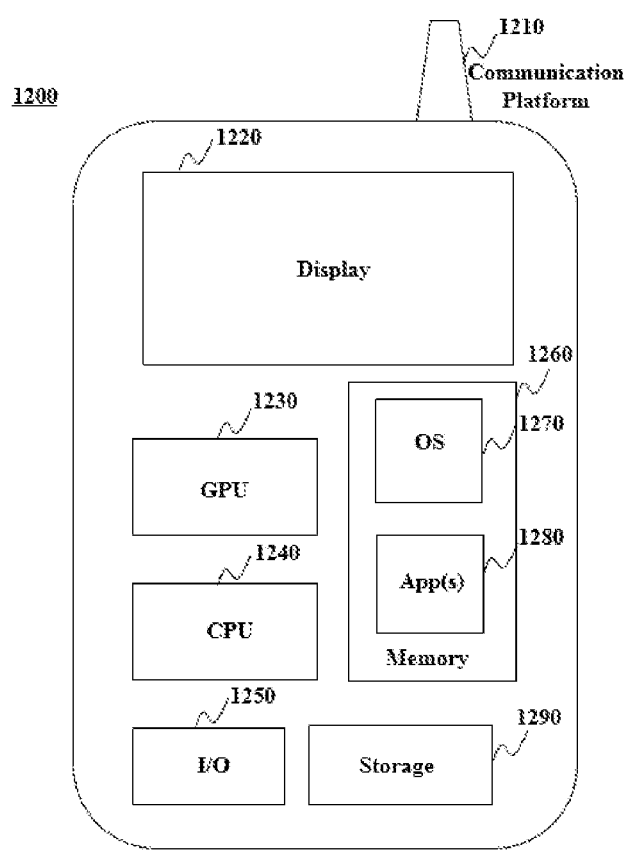
FIG. 12 depicts the architecture of a mobile device that may be used to implement a specialized system or a part thereof incorporating the present disclosure.

FIG. 12 depicts the architecture of a mobile device that may be used to realize a specialized system implementing the present disclosure. In this example, the device (e.g., the terminal 140) on which information relating to blood pressure monitoring is presented and interacted-with is a mobile device 1200, including, but is not limited to, a smart phone, a tablet, a music player, a handled gaining console, a global positioning system (GPS) receiver, and a wearable computing device (e.g., eyeglasses, wrist watch, etc.), or in any other form factor. The mobile device 1200 in this example includes one or more central processing units (CPUs) 1240, one or more graphic processing units (GPUs) 1230, a display 1220, a memory 1260, a communication platform 1210, such as a wireless communication module, storage 1290, and one or more input/output (I/O) devices 1250. Any other suitable component, including but not limited to a system bus or a controller (not shown), may also be included in the mobile device 1200. As shown in FIG. 12, a mobile operating system 1270, e.g., iOS, Android, Windows Phone, etc., and one or more applications 1280 may be loaded into the memory 1260 from the storage 1290 in order to be executed by the CPU 1240. The applications 1280 may include a browser or any other suitable mobile apps for receiving and rendering information relating to blood pressure monitoring or other information from the engine 200 on the mobile device 1200. User interactions with the information stream may be achieved via the I/O devices 1250 and provided to the engine 200 and/or other components of system 100, e.g., via the network 150.

To implement various modules, units, and their functionalities described in the present disclosure, computer hardware platforms may be used as the hardware platform(s) for one or more of the elements described herein (e.g., the engine 200, and/or other components of the system 100 described with respect to FIGS. 1-11 and 14). The hardware elements, operating systems and programming languages of such computers are conventional in nature, and it is presumed that those skilled in the art are adequately familiar therewith to adapt those technologies to the blood pressure monitoring as described herein. A computer with user interface elements may be used to implement a personal computer (PC) or other type of work station or terminal device, although a computer may also act as a server if appropriately programmed. It is believed that those skilled in the art are familiar with the structure, programming and general operation of such computer equipment and as a result the drawings should be self-explanatory.

Figure 13:
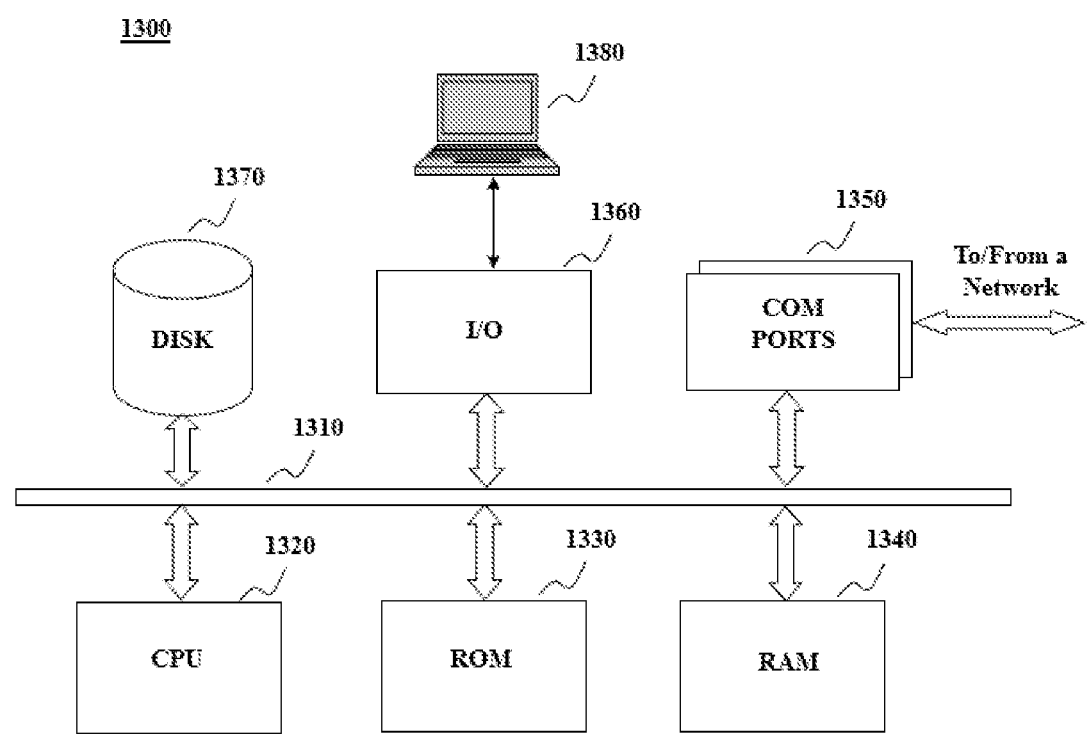
FIG. 13 depicts the architecture of a computer that may be used to implement a specialized system or a part thereof incorporating the present disclosure.

FIG. 13 depicts the architecture of a computing device that may be used to realize a specialized system implementing the present disclosure. Such a specialized system incorporating the present teaching has a functional block diagram illustration of a hardware platform that includes user interface elements. The computer may be a general purpose computer or a special purpose computer. Both may be used to implement a specialized system for the present disclosure. This computer 1300 may be used to implement any component of the blood pressure monitoring as described herein. For example, the engine 200, etc., may be implemented on a computer such as computer 1300, via its hardware, software program, firmware, or a combination thereof. Although only one such computer is shown, for convenience, the computer functions relating to the blood pressure monitoring as described herein may be implemented in a distributed fashion on a number of similar platforms, to distribute the processing load.

The computer 1300, for example, includes COM ports 1350 connected to and from a network connected thereto to facilitate data communications. The computer 1300 also includes a central processing unit (CPU) 1320, in the form of one or more processors, for executing program instructions. The exemplary computer platform includes an internal communication bus 1310, program storage and data storage of different forms, e.g., disk 1370, read only memory (ROM) 1330, or random access memory (RAM) 1340, for various data files to be processed and/or transmitted by the computer, as well as possibly program instructions to be executed by the CPU. The computer 1300 also includes an I/O component 1360, supporting input/output between the computer and other components therein such as user interface elements 1380. The computer 1300 may also receive programming and data via network communications.

Hence, aspects of the methods of the blood pressure monitoring and/or other processes, as outlined above, may be embodied in programming. Program aspects of the technology may be thought of as "products" or "articles of manufacture" typically in the form of executable code and/or associated data that is carried on or embodied in a type of machine readable medium. Tangible non-transitory "storage" type media include any or all of the memory or other storage for the computers, processors, or the like, or associated modules thereof, such as various semiconductor memories, tape drives, disk drives and the like, which may provide storage at any time for the software programming.

All or portions of the software may at times be communicated through a network such as the Internet or various other telecommunication networks. Such communications, for example, may enable loading of the software from one computer or processor into another, for example, from a management server or host computer of the engine 200 into the hardware platform(s) of a computing environment or other system implementing a computing environment or similar functionalities in connection with the blood pressure monitoring. Thus, another type of media that may bear the software elements includes optical, electrical and electromagnetic waves, such as used across physical interfaces between local devices, through wired and optical landline networks and over various air-links. The physical elements that carry such waves, such as wired or wireless links, optical links or the like, also may be considered as media bearing the software. As used herein, unless restricted to tangible "storage" media, terms such as computer or machine "readable medium" refer to any medium that participates in providing instructions to a processor for execution.

Hence, a machine-readable medium may take many forms, including but not limited to, a tangible storage medium, a carrier wave medium or physical transmission medium. Non-volatile storage media include, for example, optical or magnetic disks, such as any of the storage devices in any computer(s) or the like, which may be used to implement the system or any of its components as shown in the drawings. Volatile storage media include dynamic memory, such as a main memory of such a computer platform. Tangible transmission media include coaxial cables; copper wire and fiber optics, including the wires that form a bus within a computer system. Carrier-wave transmission media may take the form of electric or electromagnetic signals, or acoustic or light waves such as those generated during radio frequency (RF) and infrared (IR) data communications.

Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a PROM and EPROM, a FLASH-EPROM, any other memory chip or cartridge, a carrier wave transporting data or instructions, cables or links transporting such a carrier wave, or any other medium from which a computer may read programming code and/or data. Many of these forms of computer readable media may be involved in carrying one or more sequences of one or more instructions to a physical processor for execution.

Those skilled in the art will recognize that the present disclosure are amenable to a variety of modifications and/or enhancements. For example, although the implementation of various components described above may be embodied in a hardware device, it may also be implemented as a software only solution—e.g., an installation on an existing server. In addition, the blood pressure monitoring system as disclosed herein may be implemented as a firmware, firmware/software combination, firmware/hardware combination, or a hardware/firmware/software combination.

EXAMPLES

The following examples are provided for illustration purposes, and not intended to limit the scope of the present disclosure.

Example 1

A system used for measuring blood pressure may include a testing device 1400, a peripheral equipment 240 and a server 120. FIG. 14-A illustrates an exemplary testing device according to some embodiments of the embodiment. The testing device 1400 may include an information acquisition module 1410, an analysis module 220', a display module 1420 and a storage device 1470. According to the embodiment, the information acquisition module 1410 is configured for acquiring information, e.g., an ECG signal, a PPG signal, or the like, or a combination thereof. The analysis module 220' is configured for analyzing the acquired information, or determining or estimating a physiological parameter (e.g., the physiological parameter of interest), or both. The display module 1420 is configured for displaying at least some of the acquired information, the physiological parameter, or the like, or a combination thereof. The storage device 1470 is configured for storing the detected or acquired signal, the physiological parameter, or the like, or a combination thereof.

According to the embodiment, the information acquisition module 1410 includes two sensors, an electrode sensor and a photoelectric sensor. The electrode sensor is configured for detecting an ECG signal. The photoelectric sensor is configured for detecting a PPG signal. As shown in FIG. 14-A, the electrode sensor may include three electrodes, two electrodes placed on two opposite sides of the watch (illustrated as 1410), one electrode placed on the back of the watch (not shown). An electrode may include a metal or an alloy thereof. An electrode may include a coating over a metal, a coating over an alloy of a metal, or the like. The coating may be conductive. The coating may include a metal, or an alloy thereof. Merely by way of example, an electrode may include gold, platinum, copper, nickel, silver, lead, stainless steel, or the like, or an alloy thereof. An electrode may include silver chloride. An electrode may include a gold coated copper. An electrode may include a metal film. Such a metal film may be mounted onto a personal, wearble, or portable device including, e.g., a mobile device (e.g., a mobile phone), a watch, a pair of eyeglasses, or the like, or a combination thereof. An electrode may include an eletro-textile. The electro-textile may be integrated into a wearable item including, e.g., clothing, a shoe, a hat, a glove, or the like, or a combination thereof. A subject may put his two fingers on the surface of the two electrodes placed on the two opposite sides of the watch to form a closed circuit, and an ECG signal is detected. A PPG signal is detected by a photoelectric sensor placed on the backside of the testing device 1400. More detailed description of the arrangement of the electrodes may be found in a Chinese Patent Application No. 201520188152.9 filed Mar. 31, 2015, which is incorporated by reference. The ECG signal and the PPG signal may be stored in the storage device 1470, or in the server 120, or in a mobile device connected to or communicating with the testing device 1400, or the like, or a combination thereof.

The testing device may be a wearable or portable device. The testing device may be a smart watch. A top view and a bottom view of such a smart watch are shown in FIG. 14-B. The top view illustrates a schematic diagram of the watch (portions of the display interface have been elided for brevity). It may be seen from the top view that two electrodes are placed on the two sides of the watch and are configured for detecting an ECG signal. The bottom view illustrates an exemplary arrangement of a photoelectric sensor. It may be seen that the sensor includes a light source used for emitting lights and a receiving end used for receiving reflected signals (such as a PPG signal). It should be noted that more than one light sources and more than one receiving ends may be placed on the bottom of the watch, i.e. more than one reflected signals may be detected. The light sources may include a light source of any suitable wavelength, e.g., red, green, blue, infrared, purple, yellow, orange, or the like, or a combination thereof. The spectrum of the light sources may include visible spectrum, infrared spectrum, far-infrared spectrum, or the like, or a combination thereof. The watch may be worn by a subject on the top of the subject's wrist and two fingers of the subject may be placed on the electrodes, such that an ECG signal and a PPG signal may be detected.

The watch may include additional elements or components. For instance, the watch may include a GPS receiver or location sensor. The GPS receiver or location sensor may allow the subject to find his own position, or to navigate, or the like, or a combination thereof. The GPS or location sensor may allow the subject to be located by a user other than the subject.

For instance, the watch may communicate with a healthcare provider located in a location remote from the subject. The communication may be achieved directly by the watch, or indirectly via, e.g., a mobile phone carried by the subject. The physiological parameter, as well as location information, of the subject may be transmitted to the healthcare provider in real-time, periodically, or when a triggering event occurs. Exemplary trigger events are described elsewhere in the present disclosure. When an emergency occurs, e.g., the physiological parameter exceeding a threshold, the healthcare provider may be notified, the subject may be located based on the positioning information from the GPS or location sensor, and medical services may be provided accordingly.

The analysis module 220' is configured for analyzing a detected or acquired signal or information. As shown in FIG. 14-A, the analysis module 220' includes a pre-treatment unit 1430, a recognition unit 1440, a calculation unit 1450 and a calibration unit 1460.

According to the embodiment, the pre-treatment unit 1430 is configured for pre-treating the detected ECG signal and PPG signal. The recognition unit 1440 is configured for identifying a characteristic point or feature of the pre-treated ECG signal and PPG signal. The characteristic point or feature may include waveform, characteristic points, peak points, valley points, amplitude, time interval, phase, frequency, cycle, or the like, or a combination thereof. The calculation unit 1450 is configured for calculating an intermediate result, e.g., PTT based on the identified characteristic point or feature and estimating a physiological parameter of interest, e.g., SBP, DBP, heart rate, HRV, or the like, or a combination thereof. The calibration unit 1460 is configured for calibrating the estimated SBP, DBP, heart rate, HRV, or the like, or a combination thereof.

According to the embodiment, the PTT may be identified based on the maximum point A on the ECG signal and the peak point F on the PPG signal. It should be noted that during recognition of characteristic points of the PPG signal, a time window is set within which the characteristic points may be identified and used to determine PTT, i.e. the segment of the PPG waveform within the time window is analyzed to identify characteristic points and used to determine PTT. In this embodiment, the time window is set to be 2 seconds or less.

Then SBP and DBP may be estimated by a calibrated function based on the identified PTT. During the estimation of the SBP and DBP, different mathematical functions or models may be selected for use. In this embodiment, a high degree polynomial algorithm model including Equation 9 and Equation 10 are chosen to calculate SBP and DBP as described below.

$$SEP = a_1*(PTT-PTT0)^m + a_2*(PTT-PTT0)^{(m-1)} + a_3*(PTT-PTT0)^{(m-2)} + \ldots + a_m*(PTT-PTT0) + SEP0, \quad \text{Equation 9}$$

$$DBP = b_1*(PTT-PTT0)^n + b_2*(PTT-PTT0)^{(n-1)} + b_3*(PTT-PTT0)^{(n-2)} + \ldots + b_n*(PTT-PTT0) + DBP0, \quad \text{Equation 10}$$

In the equations above, the function or models coefficients m and n may be identical or different, i.e. the functions or models used to estimate the SBP and DBP may be the same or may be different. The coefficients of the functions or models $a_1, a_2, a_3, \ldots a_m$, and $b_1, b_2, b_3, \ldots b_n$ may be obtained based on one or more sets of calibration data and regression or polynomial fitting. A set of calibration data may include PTT0, SBP0 and DBP0. The calibration process of the functions are described in, e.g., Example 2 and elsewhere in the present disclosure.

A calibration process may be set during the estimation of the SBP and DBP based on a calibration data. The calibration data including PTT0, SBP0 and DBP0 may be obtained from a healthcare professional in a hospital or a doctor's office, a clinical device or a household device. The calibration data may include historical data previously calculated by the system. The calibration data may include peer data that may be obtained from peer group. As used herein, the peer group is defined as a group of people with same sex, similar age, similar height or similar weight. The calibration data may be obtained from prior calibration processes performed for the subject. The calibration data may include empirical data that may be obtained by empirical equations. The calibration data may be obtained from prior calibration processes performed on a group of subjects. See the description elsewhere in the present disclosure.

In this embodiment, a set of calibration data including a specific PTT0 that is closest to the calculated PTT may be applied in the calibrated functions. Alternatively, the average value of the PPT0's of the multiple sets of calibration data may be applied. The average value of the SBP0's and the average value of the DBP0's may be generated similarly, and applied in the calibrated functions. Then SBP and DBP values are estimated by the calibrated functions, and other physiological parameters of interest may be obtained based on the acquired information or the estimated SBP and DBP. Examples of the physiological parameters of interest may include the PR (pulse rate), heart rate, HRV (heart rate variation), cardiac murmur, blood oxygen saturation, a blood density, a pH value of the blood, a bowel sound, a brainwave, a fat content, a blood flow rate, blood vessel stiffness, blood vessel elasticity, blood vessel thickness, surface tension of blood vessel, or the like, or a combination thereof. The HRV that may be used to indicate the subject's fatigue level, psychological pressure, pressure level, anti-pressure, or the like, or a combination thereof.

Further some other physiological parameters may be taken into account in the mathematical equations to improve accuracy, e.g., PTTV0, HRV0, or the like, or a combination thereof. The exemplary equations are described below.

$$SBP = a_1*(PTT-PTT0)^m + a_2*(PTT-PTT0)^{(m-2)} + a_2*(PTT-PTT0)^{(m-2)} + \ldots + a_m*(PTT-PTT0) + b_1*(PTTV-PTTV0)^n + b_2*(PTTV-PTTV0)^{(n-2)} + b_2*(PTTV-PTTV0)^{(n-2)} + \ldots + b_n*(PTTV-PTTV0) + c_1*(HRV-HRV0)^t + c_2*(HRV-HRV0)^{(t-2)} + c_3*(HRV-HRV0)^{(t-2)} + \ldots + c_t*(HRV-HRV0) + SBP0 \quad \text{Equation 11}$$

$$DBP = d_1*(PTT-PTT0)^x + d_2*(PTT-PTT0)^{(x-2)} + d_2*(PTT-PTT0)^{(x-2)} + \ldots + d_x*(PTT-PTT0) + e_1*(PTTV-PTTV0)^y + e_2*(PTTV-PTTV0)^{(y-2)} + e_2*(PTTV-PTTV0)^{(y-2)} + \ldots + e_y*(PTTV-PTTV0) + f_1*(HRV-HRV0)^f + f_2*(HRV-HRV0)^{(f-2)} + f_3*(HRV-HRV0)^{(f-2)} + \ldots + f_j*(HRV-HRV0) + DBP0 \quad \text{Equation 12}$$

Similarly, in the equations above, the function or model coefficients n, i and x, y, j may be identical or non-identical, i.e. the functions or models used to estimate the SBP and DBP may be the same or may be different. The coefficients of the functions or models $a_1, a_2, a_3, \ldots a_m, b_1, b_2, b_3, \ldots b_n, c_1, c_2, c_3, \ldots c_i, d_1, d_2, d_3, \ldots, d_x, e_1, e_2, e_3, \ldots e_y$, and $f_1, f_2, f_3, \ldots, f_j$, may be obtained based on multiple sets of calibration data including, e.g., PTT0, SBP0, DBP0, PTTV0 and HRV0 by, e.g., regression or polynomial fitting.

The estimated SBP, DBP and the physiological parameters of interest may be outputted to a terminal such as a smartphone. The display interface is shown in FIG. 14-C. It may be seen that the physiological parameters of interest such as heart rate, BP, HRV and ECG may be displayed intuitively. Also it may be seen that HRV (heart rate variation) may reflect or influence some physiological parameters of interest. The physiological parameters of interest may include fatigue level, psychological pressure, pressure level and anti-pressure ability. And the subject may click the icons for more detailed information.

Example 2

Refer back to Example 1, a system used for measuring blood pressure is shown in FIGS. 14-A through 14-C. SBP and DBP may be estimated by a calibrated model based on an identified PTT and calibration data including PTT0, SBP0, DBP0, PTTV0 and HRV0. The coefficients of the calibrated function may be determined by a calibration process. In some embodiments, a set of calibration data relating to a subject may be acquired and stored in a storage device or the server 120. A set of calibration data may include PTT0, SBP0, DBP0, PTTV0, HRV0, or the like, or a combination thereof. A set of calibration data may be acquired by a healthcare professional in a hospital or a doctor's office, a subject himself or a nonprofessional helper. A set of calibration data may be acquired using a clinical device or a household device. A set of calibration data may be acquired based on a previous measurement using the system. One or more sets of calibration data may be used to determine the coefficients of a function or model to be calibrated by, e.g., regression. In another embodiment, one or more sets of calibration data of other subjects may be used as calibration data. In some embodiments, the coefficients of the functions or models may be set by default, i.e., empirical data may be used. In some embodiments, the coefficients of the functions or models may be calibrated by multi-point fitting.

Referring to Example 1, the calibrated functions or models may be used to estimate SBP, DBP and other physiological parameters of interest. And the estimated SBP, DBP and the physiological parameters of interest may be outputted to a terminal such as a smartphone. The display interface is shown in FIG. 14-C. It may be seen that the physiological parameters of interest such as heart rate, BP, HRV and ECG may be displayed intuitively. Also it may be seen that HRV (heart rate variation) may reflect or influence some physiological parameters of interest. The physiological parameters of interest may include fatigue level, psychological pressure, pressure level and anti-pressure ability. The subject may click the icons for more detailed information.

Example 3

FIGS. 15-A through 15-D are some examples of original data measured on two subjects, subject 1 and subject 2, under different conditions, and fitting curves with different functions, different models, or both. FIG. 15-A(a) shows the original SBP-PTT data measured on subject 1 (indicated by the diamonds connected by the dashed line), and the data was fitted with a cubic polynomial function (indicated by the solid curve). FIG. 15-A(b) shows the original DBP-PTT data measured on subject 1 (indicated by the diamonds connected by the dashed line), and the data was fitted with a quartic polynomial function (indicated by the solid curve). FIG. 15-B(a) shows the original SBP-PTT data measured on subject 2 (indicated by the diamonds connected by the dashed line), and the data was fitted with a 7th degree polynomial function (indicated by the solid curve). FIG. 15-B(b) shows the original DBP-PTT data measured on subject 2 (indicated by the diamonds connected by the dashed line), and the data was fitted with a 8th degree polynomial function (indicated by the solid curve). FIG. 15-C(a) shows the original SBP-PTT data measured on subject 2 (indicated by the diamonds connected by the dashed line), when subject 2 is in motion, and the data is fitted with a 4th degree polynomial function (indicated by the solid curve). FIG. 15-C(b) shows the original DBP-PTT data measured on subject 2 (indicated by the diamonds connected by the dashed line), when subject 2 was not in motion, and the data was fitted with a 4th degree polynomial function (indicated by the solid curve). FIG. 15-D(a) shows the original SBP-PTT data measured on subject 2 (indicated by the diamonds connected by the dashed line), when subject 2 was in motion, and the data was fitted with a 4th degree polynomial function (indicated by the solid curve). FIG. 15-D(b) shows the original DBP-PTT data measured on subject 2 (indicated by the diamonds connected by the dashed line), when subject 2 was not in motion, and the data was fitted with a 6th degree polynomial function (indicated by the solid curve).

FIGS. 15-A and 15-B provide an example of different models used for different subjects. For a same subject, different favorite model(s) may be suitable for calculating a physiological parameter of interest based on information acquired under different conditions of the subject. Examples of such conditions may include different physiological conditions of the subject chronically or at or around the acquisition time, psychological conditions of the subject chronically or at or around the acquisition time, environmental information at or around the acquisition time (e.g., room temperature, humidity, air pressure, level of activity, weather, climate, time of a day, or day of a year, etc., or the like, or a combination thereof). FIGS. 15-C(a) and 15-C(b), as well as FIGS. 15-D(a) and 15-D(b), illustrate different models used for the same subject under different conditions. For a same subject, different favorite models may generally be appropriate for SBP and DBP calculations. FIGS. 15-A(a) and 15-A(b), FIGS. 15-B(a) and 15-B(b) as well as, FIGS. 15-C(a) and 15-C(b) illustrates that different models may be used for the same subject in calculating SBP and DBP.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure. In addition, the term "logic" is representative of hardware, firmware, software (or any combination thereof)

to perform one or more functions. For instance, examples of "hardware" include, but are not limited to, an integrated circuit, a finite state machine, or even combinatorial logic. The integrated circuit may take the form of a processor such as a microprocessor, an application specific integrated circuit, a digital signal processor, a micro-controller, or the like.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "circuit," "unit," "module," "component," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including but not limited to wireless, wireline, optical fiber cable, RF, etc., or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB.NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution—e.g., an installation on an existing server or mobile device. In addition, the financial management system disclosed herein may be implemented as a firmware, firmware/software combination, firmware/hardware combination, or a hardware/firmware/software combination.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

The invention claimed is:

1. A device comprising
memory storing instructions; and
at least one processor that executes the instructions to perform operations comprising:
receiving a first signal representing heart activity of a subject;
receiving a second signal representing time-varying information on at least one pulse wave of the subject;
identifying, using the at least one processor, a first feature in the first signal;
identifying, using the at least one processor, a second feature in the second signal;
computing, using the at least one processor, a pulse transit time based on a difference between the first feature and the second feature;
receiving a first set of calibration values relating to the subject, wherein the first set of calibration values include a first calibration pulse transit time, a first variation between the first calibration pulse transit time and the computed pulse transit time; and determining if the first variation is equal to or lower than a first threshold; and
calculating, using the at least one processor, a blood pressure of the subject according to a first model based on the computed pulse transit time and the first set of calibration values.

2. The device of claim 1, the receiving the first signal comprising communicating with a first sensor configured to acquire the first signal at a first location on the body of the subject.

3. The device of claim 2, the receiving the second signal comprising communicating with a second sensor configured to acquire the second signal at a second location on the body of the subject.

4. The device of claim 3, the first location and the second location being the same part of the body.

5. The device of claim 1, the first signal or the second signal comprising an optical signal.

6. The device of claim 1, the first signal or the second signal comprising an electrical signal.

7. The device of claim 1, wherein
the first feature of the first signal corresponds to a first time point;
the identifying the second feature comprises:
selecting a segment of the second signal, the segment occurring within a time window from the first time point; and
locating the second feature corresponding to a second time point in the segment; and
the computing the pulse transit time comprises determining a time interval between the first time point and the second time point.

8. The device of claim 1, the at least one processor further
retrieving, from a plurality of sets of calibration values, a second set of calibration values comprising a second calibration pulse transit time; and
deriving the first model based on the first set of calibration values and the second set of calibration values.

9. The device of claim 1, wherein the first model is specific to the subject.

10. The device of claim 1, wherein the first signal or the second signal comprises a PPG waveform, an ECG waveform, or a BCG waveform.

11. A method comprising:
receiving a first signal representing heart activity of a subject;
receiving a second signal representing time-varying information on at least one pulse wave of the subject;
identifying a first feature in the first signal;
identifying a second feature in the second signal;
computing a pulse transit time based on a difference between the first feature and the second feature;
receiving a first set of calibration values relating to the subject, wherein the first set of calibration values include a first calibration pulse transit time, a first variation between the first calibration pulse transit time and the computed pulse transit time; and determining if the first variation is equal to or lower than a first threshold; and
calculating a blood pressure of the subject according to a first model based on the computed pulse transit time and the first set of calibration values.

12. The method of claim 11 further comprising acquiring the first signal at a first location on the body of the subject.

13. The method of claim 12 further comprising acquiring the second signal at a second location on the body of the subject.

14. The method of claim 13, the first location and the second location being the same part of the body.

15. The method of claim 11, the first signal or the second signal comprising an optical signal.

16. The method of claim 11, the first signal or the second signal comprising an electrical signal.

17. The method of claim 11, wherein
the first feature of the first signal corresponds to a first time point;
the identifying the second feature comprises:
selecting a segment of the second signal, the segment occurring within a time window from the first time point; and
locating the second feature corresponding to a second time point in the segment; and
the computing the pulse transit time comprises determining a time interval between the first time point and the second time point.

18. The method of claim 11 further comprising receiving information relating to the subject or a condition when the first signal or the second signal is acquired.

19. The method of claim 18, the calculating the blood pressure of the subject comprising applying the received information relating to the subject.

20. A system comprising:
an acquisition module configured to receive a first signal representing heart activity of a subject, and a second signal representing time-varying information on at least one pulse wave of the subject; and
an analysis module configured to
identify a first feature in the first signal;
identify a second feature in the second signal;
compute a pulse transit time based on a difference between the first feature and the second feature;
receive a first set of calibration values relating to the subject, wherein the first set of calibration values include a first calibration pulse transit time, a first variation between the first calibration pulse transit time and the computed pulse transit time; and determine if the first variation is equal to or lower than a first threshold; and
calculate a blood pressure of the subject according to a model based on the computed pulse transit time and a first set of calibration values.

* * * * *